(12) United States Patent
Bishop

(10) Patent No.: US 10,231,958 B2
(45) Date of Patent: Mar. 19, 2019

(54) METHODS AND COMPOSITIONS FOR ENHANCING CHEMOTHERAPY

(71) Applicant: Alexander James Roy Bishop, San Antonio, TX (US)

(72) Inventor: Alexander James Roy Bishop, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/520,011

(22) PCT Filed: Oct. 23, 2015

(86) PCT No.: PCT/US2015/057155
§ 371 (c)(1),
(2) Date: Apr. 18, 2017

(87) PCT Pub. No.: WO2016/065283
PCT Pub. Date: Apr. 28, 2016

(65) Prior Publication Data
US 2017/0326120 A1    Nov. 16, 2017

(51) Int. Cl.
| A61K 31/44 | (2006.01) |
| A61K 33/24 | (2006.01) |
| A61K 45/06 | (2006.01) |
| A61K 31/675 | (2006.01) |

(52) U.S. Cl.
CPC ............ *A61K 31/44* (2013.01); *A61K 31/675* (2013.01); *A61K 33/24* (2013.01); *A61K 45/06* (2013.01)

(58) Field of Classification Search
CPC ...... A61K 31/44; A61K 45/06; A61K 31/675; A61K 33/24
See application file for complete search history.

(56) References Cited

U.S. PATENT DOCUMENTS

| 2008/0063724 A1* | 3/2008 | Desai ................... A61K 9/0019 424/491 |
| 2011/0178076 A1 | 7/2011 | Huber ........................ 514/229.8 |
| 2012/0010230 A1 | 1/2012 | MacDougall ................. 514/278 |
| 2013/0005645 A1 | 1/2013 | Vitek ............................ 514/1.4 |
| 2013/0029909 A1 | 1/2013 | Ryan ............................. 514/8.1 |
| 2013/0195884 A1 | 8/2013 | Boutros ...................... 424/158.1 |
| 2014/0243239 A1 | 8/2014 | Johnson ............................ 506/9 |
| 2014/0302030 A1* | 10/2014 | Kim ................. A61K 39/39558 424/135.1 |

FOREIGN PATENT DOCUMENTS

| WO | WO/14/120995 | 8/2014 |
| WO | WO/15/126903 | 8/2015 |

OTHER PUBLICATIONS

Schwartzberg et al. (Clinical Cancer research 19(10); 2745-2754).*
Recchia( Cancer Medicine 2012; 1(1): 89-95).*
Silver (J. Clinical Oncology 28(7); 2010; 1145-1153.*
Yang et al. Oncology Reports 33: 2537-2544, 2015.*
Abdelrahman et al., "N-Acetylcysteine Improves Renal Hemodynamics in Rats With Cisplatin-Induced Nephrotoxicity," *J Appl Toxicol* 2010, vol. 30, pp. 15-21.
Anderson et al., "Buthionine Sulphoximine Alone and in Combination with Melphalan (L-PAM) is Highly Cytotoxic for Human Neuroblastoma Cell Lines," *Eur J Cancer* 1997, vol. 33, pp. 2016-2019.
Bandyopadhyay et al., "Doxorubicin in Combination With a Small TGFβ Inhibitor: A Potential Novel Therapy for Metastatic Breast Cancer in Mouse Models," *PLoS One* 5 2010, e10365.
Bass et al., "Concordance Between the Chang and the International Society of Pediatric Oncology (SIOP) Ototoxicity Grading Scales in Patients Treated With Cisplatin for Medulloblastoma," *Pediatr Blood Cancer* 2004, vol. 61, pp. 601-605.
Baud, et al., "Is NF-kappaB a good target for cancer therapy? Hopes and pitfalls," *Nat Rev Drug Discov* 2009, vol. 8, pp. 33-40.
Bayomi et al., "Evaluation of renal protective effects of inhibiting TGF-β type I receptor in a cisplatin-induced nephrotoxicity model," *Eur Cytokine Netw* 2013, vol. 24, No. 4, pp. 139-147.
Bostrom et al., "MMP-1 expression has an independent prognostic value in breast cancer," *BMC Cancer* 2011, 11:348.
Caporali et al., "NF-κB is Activated in Response to Temozolomide in an AKT-dependent Manner and Confers Protection Against the Growth Suppressive Effect of the Drug," *J Transl Med* 2012, 10:252.
Carter, et al., "Sorafenib is efficacious and tolerated in combination with cytotoxic or cytostatic agents in preclinical models of human non-small cell lung carcinoma" *Cancer Chemother Pharmacol.* 2007, 59:188.
Cassidy et al., "Cyclooxygenase-2 Induction by Paclitaxel, Docetaxel, and Taxane Analogues in Human Monocytes and Murine Macrophages," *Clin Cancer Res* 2002, vol. 8, No. 3, pp. 846-855.
Castro et al., "ViaComplex: software for landscape analysis of gene expression networks in genomic context," *Bioinformatics* 2009, vol. 25, No. 11, pp. 1468-1469.
Chan et al., "Chemotherapy advances in small-cell lung cancer," *J Thorac Dis*. 2013, vol. 5, Suppl 5, S565-S578.
Chang et al., "Role of prostaglandin E2-dependent angiogenic switch in cyclooxygenase 2-induced breast cancer progression," *Proc Natl Acad Sci USA* 2004, vol. 101, pp. 591-596.
Chen et al., "N-Acetylcysteine prevents ifosfamide-induced nephrotoxicity in rats," *Br J Pharmacol* 2008, vol. 153, pp. 1364-1372.
Chen, Kuo, "Role of glutathione in the regulation of Cisplatin resistance in cancer chemotherapy," *Met Based Drugs* 2010, 430939.
Cheng et al., "High MMP-1 mRNA expression is a risk factor for disease-free and overall survivals in patients with invasive breast carcinoma," *J Surg Res* 2008, vol. 146, No. 1, pp. 104-109.
Cullinan et al., "Nrf2 is a direct PERK substrate and effector of PERK-dependent cell survival," *Mol Cell Biol* 2003, vol. 23, No. 20, pp. 7198-7209.

(Continued)

*Primary Examiner* — Shirley V Gembeh
(74) *Attorney, Agent, or Firm* — Norton Rose Fulbright US LLP

(57) ABSTRACT

Embodiments of the invention are directed to methods and compositions using low dose sorafenib to enhance a cancer therapy.

8 Claims, 34 Drawing Sheets

(56) References Cited

OTHER PUBLICATIONS

Deng, "Multiple roles of Nrf2-Keap1 signaling: regulation of development and xenobiotic response using distinct mechanisms," *Fly (Austin)* 2014, vol. 8, No. 1, pp. 7-12.
Drablos et al., "Alkylation damage in DNA and RNA-repair mechanisms and medical significance," *DNA Repair (Amst)* 2004, vol. 3, pp. 1389-1407.
Friedman et al., "Cyclophosphamide resistance in medulloblastoma," *Cancer Res* 1992, vol. 52, No. 19, pp. 5373-5378.
Friedman et al., "Temozolomide and treatment of malignant glioma," *Clin Cancer Res* 2000, vol. 6, No. 7, pp. 2585-2597.
Frolov et. al., "Inhibition of Ion Channels and Heart Beat in *Drosophila* by Selective COX-2 Inhibitor SC-791," *PLoS One* 2012, vol. 7, No. 6, e38759.
Fry et al., "Genome-wide responses to DNA-damaging agents," *Annu Rev Microbiol* 2005, vol. 59, pp. 357-377.
Gatenby et al., "Suppression of wound healing in tumor bearing animals as a model for tumor-host interaction: mechanism of suppression," *Cancer Res* 1990, vol. 50, No. 24, pp. 7997-8001.
Hanly et al., "The Effects of N-acetylcysteine on Ifosfamide Efficacy in a Mouse Xenograft Model," *Anticancer Res* 2012, vol. 32, No. 9, pp. 3791-3798.
Heiser et al., "Subtype and pathway specific responses to anticancer compounds in breast cancer," *Proc Natl Acad Sci USA* 2012, vol. 109, No. 8, pp. 2724-2729.
Hernandez-Aya et al., "Adjuvant systemic therapies in breast cancer," *Surg Clin North Am* 2013, vol. 93, No. 2, pp. 473-491.
Heusinkveld et al., "M2 macrophages induced by prostaglandin E2 and IL-6 from cervical carcinoma are switched to activated M1 macrophages by CD4+ Th1 cells," *J Immunol* 2011, vol. 187, No. 3, pp. 1157-1165.
Hoeflich et al., "In vivo antitumor activity of MEK and phosphatidylinositol 3-kinase inhibitors in basal-like breast cancer models," *Clin Cancer Res* 2009, vol. 15, No. 14, pp. 4649-4664.
Hoffmann et al., "Multiple control of interleukin-8 gene expression," *J Leukoc Biol* 2002, vol. 72, pp. 847-855.
Hooper et al., "Medusa: a simple tool for interaction graph analysis," *Bioinforinatics* 2005, vol. 21, No. 24, pp. 4432-4433.
Hotamisligil, "Endoplasmic reticulum stress and the inflammatory basis of metabolic disease," *Cell* 2010, vol. 140, No. 6, pp. 900-917.
International Preliminary Report on Patentability in International Application No. PCT/US2015/057155 dated May 4, 2017.
International Search Report and Written Opinion in International Application No. PCT/US2015/057155 dated Jan. 21, 2016.
Jaramillo, et al., "The emerging role of the Nrf2-Keap1 signaling pathway in cancer," *Genes Dev* 2013, vol. 27, No. 20, pp. 2179-2191.
Jones et al., "Pharmacokinetic/pharmacodynamic interactions of intensive cyclophosphamide, cisplatin, and BCNU in patients with breast cancer," *Breast Cancer Res Treat* 1993, vol. 26, pp. S11-S17.
Kerkar et al., "Cellular constituents of immune escape within the tumor microenvironment," *Cancer Res* 2012, vol. 72, No. 13, pp. 3125-3130.
Kitanovic et al., "Metabolic response to MMS-mediated DNA damage in *Saccharomyces cerevisiae* is dependent on the glucose concentration in the medium," *FEMS Yeast Res* 2009, vol. 9, No. 4, pp. 535-551.
Kusumoto et al., "Cyclophosphamide-induced cardiotoxicity with a prolonged clinical course diagnosed on an endomyocardial biopsy," *Intern Med* 2013, vol. 52, No. 20, pp. 2311-2315.
Lee et al., "Adaptive Response to GSH Depletion and Resistance to L-Buthionine-(S,r)-Sulfoximine: Involvement of Nrf2 Activation," *Mol Cell Biochem* 2008, vol. 318, Nos. 1-2, pp. 23-31.
Li et al., "Mechanism of Chemical Activation of Nrf2," *PLoS One* 2012, vol. 7, e35122.
Lin et al., "IRE1 signaling affects cell fate during the unfolded protein response," Science 2007, vol. 318, No. 5852, pp. 944-949.

Lin et al., "Resveratrol enhances the therapeutic effect of temozolomide against malignant glioma in vitro and in vivo by inhibiting autophagy," *Free Radic Biol Med* 2012, vol. 52, No. 2, pp. 377-391.
Ling et al., "Crosstalk between NFκB and glucocorticoid signaling: a potential target of breast cancer therapy," *Cancer Lett* 2012, vol. 322, No. 2, pp. 119-126.
Liu et al., "The role of MMP-1 in breast cancer growth and metastasis to the brain in a xenograft model." *BMC Cancer* 2012, 12:583.
Lopez-Bergami et al., "Emerging roles of ATF2 and the dynamic AP1 network in cancer," *Nat Rev Cancer* 2010, vol. 10, No. 1, pp. 65-76.
Ma et al., "Delineation of a negative feedback regulatory loop that controls protein translation during endoplasmic reticulum stress," *J Biol Chem* 2003, vol. 278, pp. 34864-34873.
Minn et al., "Genes that mediate breast cancer metastasis to lung," *Nature* 2005, vol. 436, No. 7050, pp. 518-524.
Mitsuishi et al., "Nrf2 redirects glucose and glutamine into anabolic pathways in metabolic reprogramming," *Cancer Cell* 2012, vol. 22, No. 1, pp. 66-79.
Novoa et al., *J Cell Biol* 2001, vol. 153, No. 5, pp. 1011-1022.
Omuro et al., "Glioblastoma and other malignant gliomas: a clinical review," *JAMA* 2013, vol. 310, No. 17, pp. 1842-1850.
Ravi et al., "A Network of Conserved Damage Survival Pathways Revealed by a Genomic RNAi Screen," *PLoS Genet* 2009, vol. 5, No. 6, e1000527.
Rowe et al., "DNA damage-induced reactive oxygen species (ROS) stress response in *Saccharomyces cerevisiae*," *Free Radic Biol Med* 2008, vol. 45, No. 8, pp. 1167-1177.
Saleem et al., "Metabolic activation of temozolomide measured in vivo using positron emission tomography," *Cancer Res* 2003, vol. 63, No. 10, pp. 2409-2415.
Subbaramaiah et al., "Cyclooxygenase-2-derived prostaglandin E2 stimulates Id-1 transcription," *J Biol Chem* 2008, 283, 33955-33968.
Sykiotis et al., "Keap1/Nrf2 Signaling Regulates Oxidative Stress Tolerance and Lifespan in *Drosophila*," *Dev Cell* 2008, vol. 14, No. 1, pp. 76-85.
Varvas et al., "Direct evidence of the cyclooxygenase pathway of prostaglandin synthesis in arthropods: genetic and biochemical characterization of two crustacean cyclooxygenases," *Insect Biochem Mol Biol* 2009, vol. 39, No. 12, pp. 851-860.
Walhout et al., "Integrating interactome, phenome, and transcriptome mapping data for the C. elegans germline," *Curr Biol* 2002, vol. 12, No. 22, pp. 1952-1958.
Wang et al., "Nrf2 enhances resistance of cancer cells to chemotherapeutic drugs, the dark side of Nrf2," *Carcinogenesis* 2008, vol. 29, No. 6, pp. 1235-1243.
Wilhelm et al., "BAY 43-9006 exhibits broad spectrum oral antitumor activity and targets the RAF/MEK/ERK pathway and receptor tyrosine kinases involved in tumor progression and angiogenesis," *Cancer Res* 2004, vol. 64, No. 19, pp. 7099-7109.
Workman et al., "A systems approach to mapping DNA damage response pathways," *Science* 2006, vol. 312, No. 5776, pp. 1054-1059.
Wu et al., "The chemoprotective agent N-acetylcysteine blocks cisplatin-induced apoptosis through caspase signaling pathway," *J Pharmacol Exp Ther* 2005, vol. 312, No. 2, pp. 424-431.
Wu, "Heat shock transcription factors: structure and regulation," *Annu Rev Cell Dev Biol* 1995, vol. 11, pp. 441-469.
Xia et al., "MetaboAnalyst: a web server for metabolomic data analysis and interpretation," *Nucleic Acids Res* 2009, vol. 37, pp. W652-W660.
Xia et al., "MetaboAnalyst 2.0—a comprehensive sewer for metabolomic data analysis," *Nucleic Acids Res* 2012, vol. 40, pp. W127-W133.
Zanotto-Filho et al., "The Pharmacological NFkappaB Inhibitors BAY117082 and MG132 Induce Cell Arrest and Apoptosis in Leukemia Cells Through ROS-mitochondria Pathway Activation," *Cancer Lett* 2010, vol. 288, No. 2, pp. 192-203.

\* cited by examiner

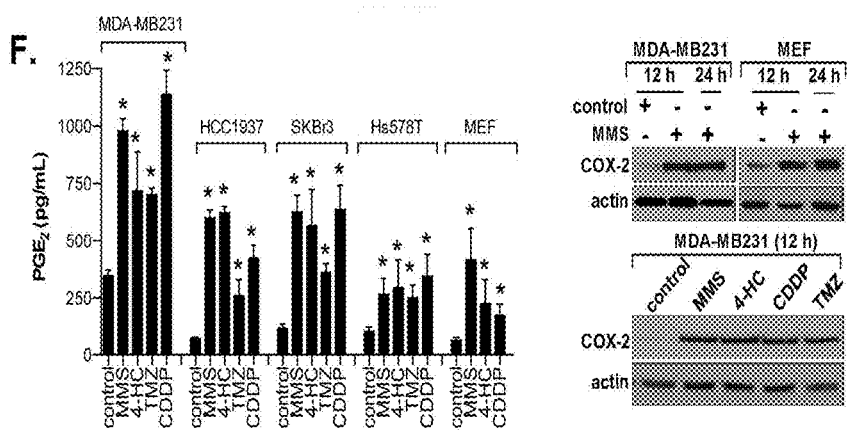
FIG. 5F
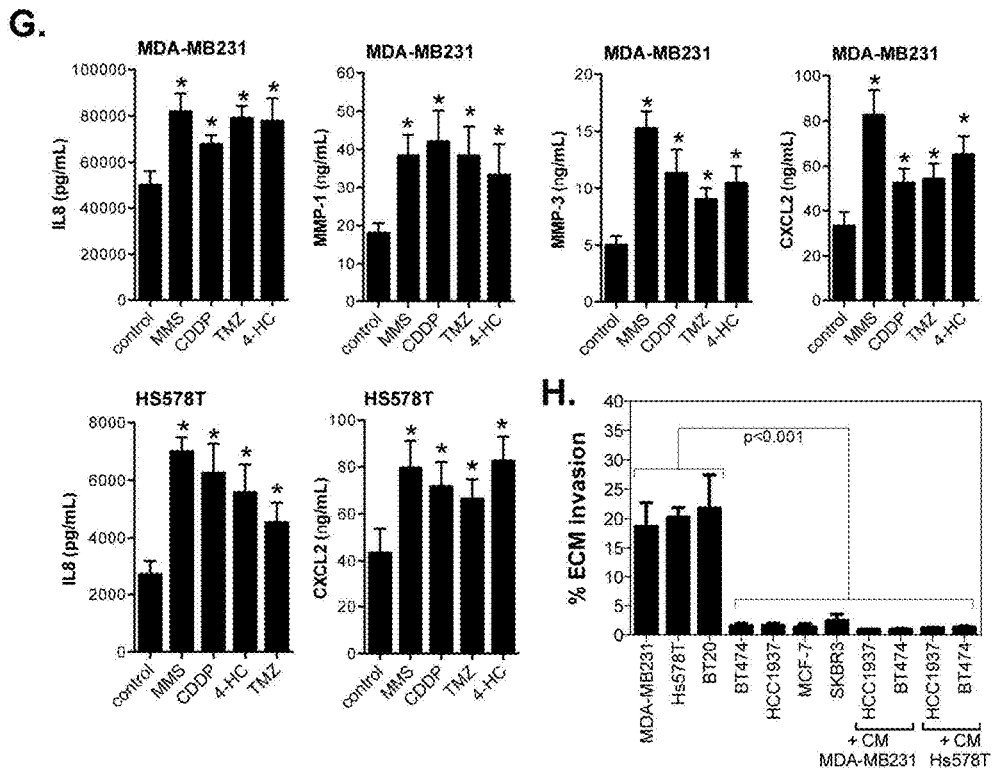
FIG. 5G
FIG. 5H

| TF | Target Gene Symbol | p-value | Evalue | FDR (%) |
|---|---|---|---|---|
| MDA-MB231 | | | | |
| NFKB1/RELA | IL6, MMP3, IL8, TFPI2, CXCL3, CXCL2, CXCL1 | 1.0E-05 | 3.5 | 1.8E-03 |
| JUN/AP-1 | MMP1, PTGS2, IL6, IL8, TFPI2 | 6.0E-05 | 2.8 | 3.6E-03 |
| CTNNB1 | PTGS2, ID3, IL6, IL8, MMP1, CTGF, IKBKG | 4.6E-04 | 1.9 | 5.4E-03 |
| MEFs | | | | |
| NFKB1 | Il15, Tlr2, Cxcl2, Icam1, Areg, Ptgs2, Col10a1 | 1.0E-05 | 5.0 | 8.8E-04 |
| RUNX2 | Mmp13, Col10a1, Ptgs2 | 2.0E-05 | 2.9 | 1.8E-03 |
| CTNNB1 | Fgf18, Ikbkg, Vegfc, Id3, Ptgs2, Cd14 | 3.1E-04 | 1.8 | 3.5E-03 |
| GLI2 | Igfbp3, Mmp10, Efna1, Mmp13 | 3.4E-04 | 1.7 | 4.4E-03 |

| Groups | A | B | C | D |
|---|---|---|---|---|
| Histopathology (H&E) | | | | |
| Vessels | ++ | +++ | + | + |
| Apoptosis | Present | Increased | Increased | Present |
| Mitoses | Prominent | Yes | Abnormal | Yes |
| Capsule | Thin | Thin | Thick | Thin |
| PCNA IHC | +++ | ++ | ++ | +++ |
| Massom's staining | | | | |
| Fibrosis | Yes | Mild | Marked | Mild |
| Keratin | + | + | +++ | + |
| Collagen | + | ++ | +++ | ++ |

C.

| Pathway Enrichment Analysis output (DAViD bioinformatics) | | | | | | | | |
|---|---|---|---|---|---|---|---|---|
| Input: D. melanogaster screen hits | | Microarray | | RNAi screening hits | | FUSION | | |
| Category | Term | Count | PValue | Count | PValue | Count | PValue | GENES ADDED BY FUSION |
| KEGG_PATHWAY | dme00230:Purine metabolism | ND | ND | 15 | 9.4E-02 | 23 | 1.1E-02 | 8 |
| KEGG_PATHWAY | dme00240:Pyrimidine metabolism | ND | ND | 12 | 4.6E-02 | 15 | 6.5E-02 | 3 |
| KEGG_PATHWAY | dme00980:Metabolism of xenobiotics by cytochrome P | 21 | 1.3E-14 | ND | ND | 24 | 1.6E-07 | 3 |
| KEGG_PATHWAY | dme00982:Drug metabolism | 21 | 2.6E-14 | ND | ND | 24 | 3.0E-07 | 3 |
| KEGG_PATHWAY | dme04480:Glutathione metabolism | 15 | 2.8E-08 | ND | ND | 18 | 4.4E-04 | 3 |
| KEGG_PATHWAY | dme00983:Drug metabolism | 11 | 5.0E-05 | ND | ND | 14 | 1.8E-02 | 3 |
| KEGG_PATHWAY | dme03040:Spliceosome | ND | ND | 19 | 2.0E-03 | 20 | 4.3E-02 | 1 |
| KEGG_PATHWAY | dme03420:Nucleotide excision repair | ND | ND | 7 | 5.2E-02 | 8 | 9.6E-02 | 1 |
| KEGG_PATHWAY | dme03022:Basal transcription factors | ND | ND | 13 | 2.4E-01 | 13 | 2.2E-05 | 0 |
| KEGG_PATHWAY | dme03020:RNA polymerase | ND | ND | 8 | 3.8E-03 | 8 | 2.8E-02 | 0 |
| KEGG_PATHWAY | dme03050:Proteasome | ND | ND | 8 | 8.6E-02 | 8 | 7.6E-02 | 0 |

| Input: Human pathologies of Fly genes | | Microarray | | RNAi screening hits | | FUSION | | |
|---|---|---|---|---|---|---|---|---|
| Category | Term | Count | PValue | Count | PValue | Count | PValue | GENES ADDED BY FUSION |
| KEGG_PATHWAY | hsa00230:Purine metabolism | 5 | 9.1E-02 | 12 | 1.5E-02 | 17 | 1.0E-03 | 5 |
| KEGG_PATHWAY | hsa00240:Pyrimidine metabolism | ND | ND | 9 | 1.5E-02 | 12 | 2.8E-03 | 3 |
| KEGG_PATHWAY | hsa04480:Glutathione metabolism | ND | ND | ND | ND | 6 | 6.7E-02 | 6 |
| REACTOME_PATHWAY | REACT_216:DNA Repair | ND | ND | 11 | 5.8E-03 | 15 | 4.0E-04 | 4 |
| PANTHER_PATHWAY | P00059:p53 pathway | ND | ND | 8 | 8.1E-02 | 11 | 2.1E-02 | 3 |
| KEGG_PATHWAY | hsa04110:Cell cycle | ND | ND | ND | ND | 10 | 9.9E-02 | 10 |
| KEGG_PATHWAY | hsa04150:mTOR signaling pathway | ND | ND | ND | ND | 6 | 7.7E-02 | 6 |
| KEGG_PATHWAY | hsa03022:Basal transcription factors | ND | ND | 13 | 7.4E-10 | 13 | 1.4E-08 | 0 |
| KEGG_PATHWAY | hsa04114:Oocyte meiosis | ND | ND | 13 | 3.3E-04 | 16 | 9.0E-05 | 3 |
| REACTOME_PATHWAY | REACT_13:Metabolism of amino acids | ND | ND | ND | ND | 14 | 5.7E-02 | 14 |
| BIOCARTA | h_eif4Pathway:Regulation of eIF4e and p70 S6 Kinase | ND | ND | ND | ND | 6 | 8.2E-02 | 6 |
| REACTOME_PATHWAY | REACT_17015:Metabolism of proteins | ND | ND | 21 | 2.2E-04 | 25 | 1.2E-04 | 4 |
| KEGG_PATHWAY | hsa03010:Ribosome | ND | ND | 11 | 6.9E-04 | 14 | 9.3E-05 | 3 |
| KEGG_PATHWAY | hsa03420:Nucleotide excision repair | ND | ND | 8 | 6.4E-04 | 9 | 5.6E-04 | 1 |
| KEGG_PATHWAY | hsa03040:Spliceosome | ND | ND | 12 | 3.7E-03 | 13 | 9.1E-03 | 1 |
| REACTOME_PATHWAY | REACT_152:Cell Cycle, Mitotic | ND | ND | 22 | 6.5E-03 | 23 | 4.2E-02 | 1 |
| KEGG_PATHWAY | hsa03310:Lysine degradation | ND | ND | 5 | 6.2E-02 | 6 | 4.3E-02 | 1 |
| KEGG_PATHWAY | hsa03050:Proteasome | ND | ND | 5 | 9.6E-04 | 5 | 4.1E-03 | 0 |
| KEGG_PATHWAY | hsa03020:RNA polymerase | ND | ND | 6 | 1.4E-02 | 6 | 3.3E-02 | 0 |
| KEGG_PATHWAY | hsa04340:Hedgehog signaling pathway | ND | ND | 6 | 4.1E-02 | 6 | 9.9E-02 | 0 |
| PANTHER_PATHWAY | P00045:Notch signaling pathway | ND | ND | 8 | 8.1E-03 | 8 | 3.4E-03 | 0 |
| PANTHER_PATHWAY | P00060:Ubiquitin proteasome pathway | ND | ND | 10 | 9.9E-04 | 10 | 5.4E-03 | 0 |
| REACTOME_PATHWAY | REACT_1675:mRNA Processing | ND | ND | 13 | 9.1E-10 | 13 | 1.4E-08 | 0 |
| REACTOME_PATHWAY | REACT_11045:Signaling by Wnt | ND | ND | 9 | 2.3E-03 | 9 | 9.4E-03 | 0 |
| REACTOME_PATHWAY | REACT_383:DNA Replication | ND | ND | 11 | 4.1E-03 | 11 | 2.0E-02 | 0 |
| REACTOME_PATHWAY | REACT_12472:Regulatory RNA pathways | ND | ND | 4 | 3.1E-02 | 4 | 5.6E-02 | 0 |
| REACTOME_PATHWAY | REACT_1538:Cell Cycle Checkpoints | ND | ND | 11 | 1.1E-02 | 11 | 4.8E-02 | 0 |

FIG. 9C

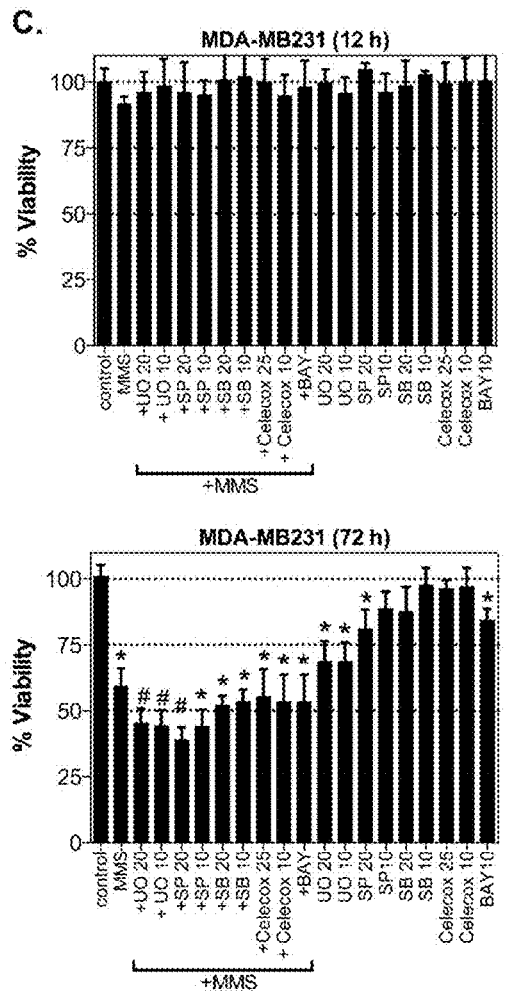 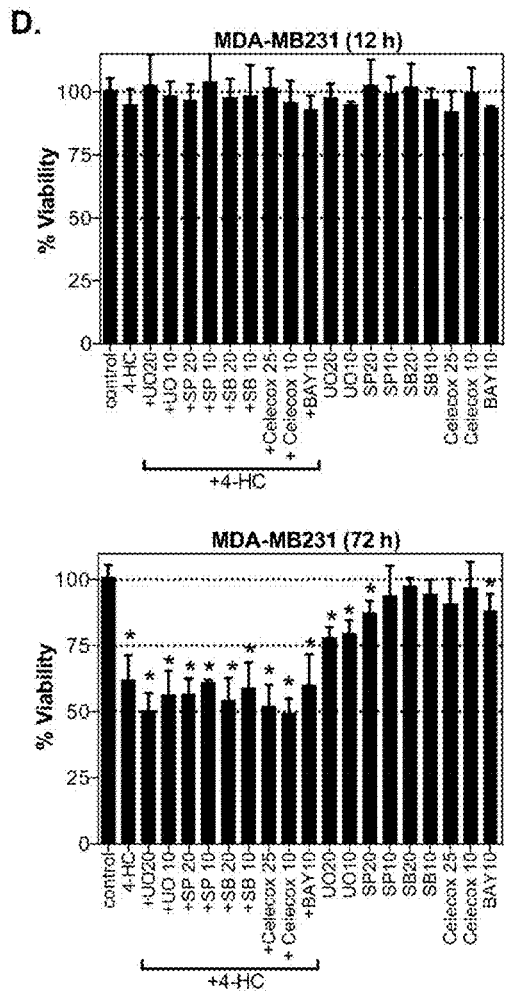
FIG. 11C  FIG. 11D

METHODS AND COMPOSITIONS FOR ENHANCING CHEMOTHERAPY

This Application is a national phase application under 35 U.S.C. § 371 of International Application No. PCT/US2015/057155, filed Oct. 23, 2015, which claims priority to U.S. Provisional Patent Applications Ser. No. 62/068,068 filed Oct. 24, 2014. Both of which are incorporate herein in their entirety.

BACKGROUND

DNA damaging agents have long been understood to drive mutagenesis while also being useful as cytotoxic agents to chemotherapeutically treat cancers. The appropriate response to such insults—mitigating cellular toxicity and inducing repair or initiating cell death—is critical, particularly in multicellular organisms. In response to genomic damage, DNA damage response (DDR) proteins, including ATM, ATR, CHK1/2 and p53-regulated pathways, instigate many of the responses, particularly DNA repair. However, some of the pleiotropic responses to damage appear to involve processes other than the central DDR; for example activation of antioxidant systems, switches in metabolic flow, drug efflux, and phase I/II drug detoxification pathways also seem to take part in this intricate response network in a thus far not fully understood pattern (Ravi et al., 2009, *PLoS Genet* 5, e1000527; Altieri et al., 2008, *Antioxid Redox Signal* 10, 891-937; Workman et al., 2006, *Science* 312, 1054-9).

Even though alkylating agents are assigned as one of the most powerful carcinogenic DNA damaging agents, compounds such as cyclophosphamide, carmustine, melphalan, temozolomide, and alkylation-like platinum compounds such as cisplatin are still at the forefront of many chemotherapy regimens used to treat breast (Hernandez-Aya, Gonzalez-Angulo, 2013, *Surg Clin North Am* 93, 473-91; Jones et al., 1993, *Breast Cancer Res Treat* 26 Suppl, S11-7), gliomas (Omuro, DeAngelis, 2013, *JAMA* 310, 1842-50; Friedman et al., 2000, *Clin Cancer Res* 6, 2585-97) and lung cancer (Chan et al., 2013, *J Thorac Dis.* 5 Suppl 5, S565-78) as well as some autoimmune diseases (Kallenberg, 2013, *Ann Rheum Dis* 72 Suppl 2, ii62-5). Chemically, alkylation is the transfer of an alkyl group from one molecule to another, which biologically could be DNA, RNA, or protein. The primary mechanism of action of alkylating chemotherapies is thought to be through induction of nucleotide modification, which leads to base adducts, DNA crosslinks and strand breaks as well as reactive oxygen species (ROS) and the indirect damages this will cause (Lin et al., 2012, *Free Radic Biol Med* 52, 377-91; Drablos et al., 2004, *DNA Repair (Amst)* 3, 1389-407; Malet-Martino et al., 1999, *Curr Pharm Des* 5, 561-86). This implies impairment of the replication machinery, repair system activation, cell cycle arrest, altered transcription and/or activation of death mechanisms.

Besides cytotoxicity to cancer cells, off-target damage to healthy tissues is a frequently observed component leading to alkylating therapy failure and poor prognosis. Alkylating agents are known to cause severe damage to proliferating cells, mainly those of the immune system leading to immune suppression. However, such toxicity is not exclusive of proliferating cells since low/non-proliferating counterparts, including renal, hepatic, and cardiac tissues, are also severely affected by some alkylating agents (Abdelrahman et al., 2010, *J Appl Toxicol* 30, 15-21; Chen et al., 2008, *Br J Pharmacol* 153, 1364-72; Chen et al., 2007, *Can J Clin Pharmacol* 14, e246-50). For example, cyclophosphamide may cause severe renal failure and severe cardiotoxicity even in the first cycles of chemotherapy (Chen et al., 2007, *Can J Clin Pharmacol* 14, e246-50; Kusumoto et al., 2013, *Intern Med* 52, 2311-5), cisplatin (CDDP) may induce nephrotoxicity (Bayomi et al., 2013, *Eur Cytokine Netw* 24(4):139-47) and ototoxicity (Bass et al., 2014, *Pediatr Blood Cancer* 61, 601-5). Consequently, the harmful side effects of some alkylating agents can delay a chemotherapy protocol completion, which could favor the emergence of infections and resistant cancer phenotypes. Much of these undesirable effects are believed to be associated with production of ROS and oxidative damage to cellular structures but the mechanism is still not fully depicted (Chen et al., 2007, *Can J Clin Pharmacol* 14, e246-50).

While some preclinical studies have addressed the effect of antioxidants in minimizing off-target damages from alkylation, others have sought to identify targets that would potentiate chemotherapy toxicity or circumvent tumor cells resistance. However, there is still a key deficiency in understanding how normal cells survive alkylation and how the efficacy of alkylation in treating cancer without potentiating even more off-target toxicity to normal tissues can be improved.

SUMMARY

The discovery that alkylation, instead of decreasing, exacerbates poor prognosis-associated genes provided a basis for developing a strategy for improving alkylating therapy. A damage induced inflammatory response was traced to MAPKs. The inflammatory response can be blocked with MAPK inhibitors. Sorafenib was the most effective and broad inhibitor of this response, blocking ERK1/2 and JNK1/2 and their downstream targets NFκB and AP-1/ATF2. Sorafenib consequently inhibited downstream inflammatory mediators PTGS2, IL8, IL1B, MMP1 and MMP3 among others. Sorafenib was also able to block damage-induced angiogenesis and invasion in vitro without affecting cell viability at the doses used to achieve specific MAPKs inhibition.

Certain embodiments are directed to methods of enhancing chemotherapy by administering low-dose Sorafenib in conjunction with chemotherapy. Certain aspects are directed to methods of using and compositions comprising Sorafenib, including all polymorphs, hydrates, solvates or combinations thereof. Sorafenib (4-[4-[[4-chloro-3-(trifluoromethyl)phenyl]carbamoylamino]phenoxy]-N-methyl-pyridine-2-carboxamide) is a drug approved for the treatment of primary kidney cancer (advanced renal cell carcinoma), advanced primary liver cancer (hepatocellular carcinoma), and radioactive iodine resistant advanced thyroid carcinoma. Sorafenib inhibits several tyrosine protein kinases (VEGFR and PDGFR) (tyrosine kinase inhibitor or TKI) and Raf kinases (more avidly C-Raf than B-Raf). It also inhibits some intracellular serine/threonine kinases (e.g. C-Raf, wild-type B-Raf and mutant B-Raf). As used herein "low-dose Sorafenib" refers to a dose of Sorafenib, or compound with similar activity, that when administered alone does not result in cytotoxic or autophagic response of cancer cells. In certain aspects Sorafenib is administered at a dose of less than 0.001, 0.005, 0.01, 0.05, 0.1, 0.05, 0.1, 0.5, or 1 milligram per kilogram (mg/kg).

In certain aspects Sorafenib is administered 0.5, 1, 2, 3, 4, 5, 6, 7, 8, 9, 10, 11, or 12 minutes, hours, or days prior to, after, or prior to and after administration of a chemotherapy. Chemotherapy is a category of cancer treatment that uses chemical substances, especially one or more anti-cancer drugs (chemotherapeutic agents) that are given as part of a standardized chemotherapy regimen. Chemotherapy may be given with a curative intent, or it may aim to prolong life or to reduce symptoms. Chemotherapies include alkylating agent chemotherapy, anti-metabolite chemotherapy, anti-microtubule chemotherapy, topoisomerase inhibitor chemotherapy, and cytotoxic antibiotic chemotherapy. In certain aspects the chemotherapy is an alkylating chemotherapy. Alkylating chemotherapy includes, but is not limited to nitrogen mustards, nitrosoureas, tetrazines, aziridines, and cisplatins. Certain aspects are directed to co-administration of sorafenib with cyclophosphamide, ifosimide, carmustine, melphalan, temozolomide, cisplatin, or combinations thereof. In certain aspects two or more kinase inhibitors can be administered to mimic Sorafenib, e.g., kinase inhibitors that block ERK1/2 and JNK1/2 pathways.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1A:
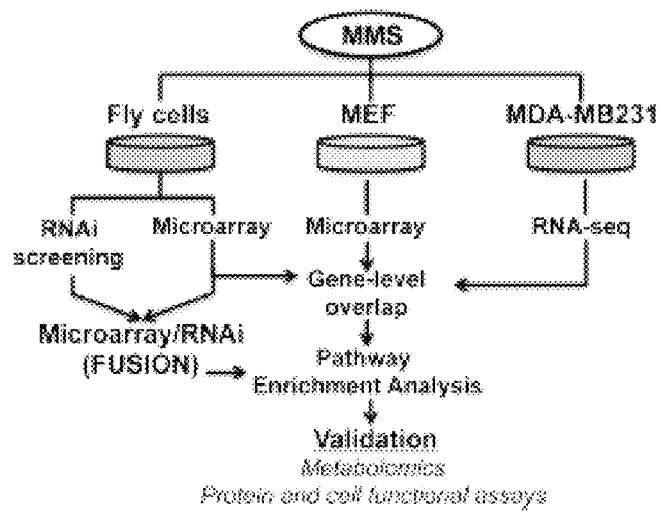
FIG. 1. Gene level overlap and System Biology Analysis of MMS-induced pathways in fly, mouse and human cell lines. (A) Venn diagrams and descriptive table showing the lack of overlap and loss of orthologs during conversion across species for MMS-induced (regular font) or repressed (underlined font) genes using Human gene symbol or Fly gene symbol-converted orthologs. Genes altered at 8 and 24 h treatments were gathered to minimize the effect of the different time of responses across species. Fisher-exact test was used to access overlap significance. (B) List of canonical pathways potentially activated by MMS in the different cell types. MMS-induced genes (MDA-MB231: RNA sequencing; MEF: microarray; Kc167 fly cells: Fused microarray+RNAi screening hits) were analyzed using DAVID, Ingenuity and Rock Pathway Enrichment tools. Pathways consistently represented across different tools ($p<0.05$) were selected and terms were grouped agreeing with the biological processes with which they are associated; (C) Metabolic pathways altered by MMS in fly and MEF. Metabolic Pathway Enrichment was performed by analyzing metabolites altered by MMS after 8 and 24 h treatment using MetaboAnalyst package. (D) GO Annotation Clustering analysis for MMS-induced genes (fold>2) using DAVID bioinformatics. Antilog of p-value ($-\log (p)$) is presented for the most relevant biological processes/functions found in each specie/cell type.

Certain embodiments are based on studies designed to understand the mechanisms of alkylation response and survival, and application of this knowledge to improve the efficacy of alkylation-based chemotherapy.

I. Methods of Treatment and Formulations

Certain embodiments are directed to administering an effective amount of Sorafenib in combination with a cancer therapy. The phrase "effective amount" indicates the amount of sorafenib that is effective in reducing inflammation, angiogenesis, and/or cancer cell migration, without inducing cytotoxicity or autophagy in a cancer cell if administered as the sole agent. Effective amounts can be determined routinely. Further guidance on dosages and administration regimens is provided below.

The term "treating" is used conventionally, e.g., the management or care of a subject for the purpose of combating, alleviating, reducing, relieving, improving, etc., one or more of the symptoms associated with a specific cancer. Administering effective amounts of sorafenib can treat one or more aspects of the cancer disease, including, but not limited to, ameliorating inflammation, reducing vascularization, and inhibiting cell migration. Sorafenib in combination with a cancer therapy results in enhancing the effectiveness of the cancer therapy. The combination therapy described herein can cause tumor regression; cause cell death; cause apoptosis; cause necrosis; inhibit cell proliferation; inhibit tumor growth; inhibit tumor metastasis; inhibit tumor migration; inhibit tumor invasion; reduce disease progression; stabilize the disease; reduce or inhibit angiogenesis; prolong patient survival; enhance patient's quality of life; reduce adverse symptoms associated with cancer; and reduce the frequency, severity, intensity, and/or duration of any of the aforementioned aspects.

Any cancer can be treated in accordance of the present invention, irrespective of the cause of the cancer, and irrespective of the genetic lesions associated with it (see, e.g., Atlas of Genetics and Cytogenetics in Oncology and Haematology on the worldwide web at infobiogen.fr/services/chromcancer/ for an atlas of genes involved in cancer). Cancers which can be treated include, e.g., cancers which are primary; which arise from a primary tumor at a secondary metastatic site; which have been treated by surgery (e.g., entirely removed, surgical resection, etc); which have been treated by chemotherapy, radiation, radiofrequency ablation, and/or any other adjunct to drug therapy; which have acquired drug-resistance; which are refractory to a chemotherapeutic agent.

Any subject can be in treated, including, mammals, such as rats, mice, dogs, cats, horses, cows, goats, sheep, monkeys, and in particular humans.

The specific dose level and frequency of dosage may vary, depending upon a variety of factors, including the activity of the active agent, its metabolic stability and length of action, rate of excretion, mode and time of administration, the age, body weight, health condition, gender, diet, baseline hematologic and biologic parameters (e.g., WBCs, granulocytes, platelets, hemoglobin, creatinine, bilirubin, albumin, etc.), etc., of the subject, and the severity, intensity, stage of the cancer, primary site of cancer, size of cancer lesion, presence or extent of metastases, surgical status, disease progression (i.e., aggressive), etc. of the disease. In the case of Sorafenib it is provided at a low-dose, non-cytotoxic dose. Given that Sorafenib at low doses enhances the effectiveness of a second therapy, the dose of a second therapy can be adjusted appropriately to (i) to supply a higher dose of the second therapy since detrimental effects of the agent can be ameliorated by the presence of low dose sorafenib or (ii) a lower dose of the second therapy is given in the cases where Sorafenib enhances the therapy and allows a less toxic dose to be administered yet still achieve the therapeutic effect sought.

The compound(s) of the present invention can be administered in any form by any effective route, including, e.g., oral, parenteral, enteral, intraperitoneal, topical, transdermal, nasally, aerosol, spray, inhalation, subcutaneous, intravenous, intramuscular, intra-arterial, intrathecal, intratumoral, etc. Sorafenib can be administered directly to the site of a tumor, either pre- or post-operatively. It can be administered in combination with any ingredient(s), active or inactive.

Sorafenib can be administered by the oral route using the pharmaceutical composition of the present invention will generally range, based on body weight, from about or less than 0.001 mg/kg to about or less than 1 mg/kg.

Any suitable dosing interval can be used in accordance with the present invention. For example, the compound can be administered once, twice (BID), three, four, etc., times a day. For example, about 1 to 10 mg, can be administered one, twice, or three times daily.

Sorafenib can be administered at any suitable time. For example, it can be administered prior to, concurrently with, and/or after chemotherapeutic agents; prior to or after radiation, radiofrequency ablation and other energy treatments; etc.

Sorafenib can be further combined with any other suitable additive or pharmaceutically acceptable carrier. Such additives include any of those used conventionally, such as those described in Remington: The Science and Practice of Pharmacy (Gennaro and Gennaro, eds, 20th edition, Lippincott Williams & Wilkins, 2000); Theory and Practice of Industrial Pharmacy (Lachman et al., eds., 3rd edition, Lippincott Williams & Wilkins, 1986); Encyclopedia of Pharmaceutical Technology (Swarbrick and Boylan, eds., 2nd edition, Marcel Dekker, 2002).

The compounds can be in any suitable form, without limitation. Forms suitable for oral use, include, but are not limited to, tablets, troches, lozenges, aqueous or oily suspensions, dispersible powders or granules, emulsions, hard or soft capsules, solutions, syrups and elixirs. Compositions intended for oral use may be prepared according to any method known to the art for the manufacture of pharmaceutical compositions.

Compounds can be formulated with other ingredients, e.g., "pharmaceutically acceptable carriers" or "excipients" to indicate they are combined with the active drug and can be administered safely to a subject for therapeutic purposes. These include, but are not limited to, antioxidants, preservatives, dyes, tablet-coating compositions, plasticizers, inert carriers, excipients, polymers, coating materials, osmotic barriers, devices and agents which slow or retard solubility, etc.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations.

Non-toxic pharmaceutically acceptable excipients that are suitable for the manufacture of tablets. These excipients may be, for example, inert diluents, such as calcium carbonate, sodium carbonate, lactose, calcium phosphate or sodium phosphate; granulating and disintegrating agents, for example, cornstarch, or alginic acid; and binding agents, for example magnesium stearate, stearic acid or talc.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

II. Chemotherapy

Alkylating agents are the oldest group of chemotherapeutics in use today. Originally derived from mustard gas used in World War I, there are now many types of alkylating agents in use. They are so named because of their ability to alkylate many molecules, including proteins, RNA and DNA. This ability to bind covalently to DNA via their alkyl group is the primary cause for their anti-cancer effects. DNA is made of two strands and the molecules may either bind twice to one strand of DNA (intrastrand crosslink) or may bind once to both strands (interstrand crosslink). If the cell tries to replicate crosslinked DNA during cell division, or tries to repair it, the DNA strands can break. This leads to a form of programmed cell death called apoptosis. Alkylating agents will work at any point in the cell cycle and thus are known as cell cycle-independent drugs. For this reason the effect on the cell is dose dependent; the fraction of cells that die is directly proportional to the dose of drug.

The subtypes of alkylating agents are the nitrogen mustards, nitrosoureas, tetrazines, aziridines, cisplatins and derivatives, and non-classical alkylating agents. Nitrogen mustards include mechlorethamine, cyclophosphamide, melphalan, chlorambucil, ifosfamide and busulfan. Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide. Aziridines include thiotepa, mytomycin and diaziquone (AZQ). Cisplatin and derivatives include cisplatin, carboplatin and oxaliplatin. They impair cell function by forming covalent bonds with the amino, carboxyl, sulfhydryl, and phosphate groups in biologically important molecules. Non-classical alkylating agents include procarbazine and hexamethylmelamine.

Anti-metabolites are a group of molecules that impede DNA and RNA synthesis. Many of them have a similar structure to the building blocks of DNA and RNA. The building blocks are nucleotides; a molecule comprising a nucleobase, a sugar and a phosphate group. The nucleobases are divided into purines (guanine and adenine) and pyrimidines (cytosine, thymine and uracil). Anti-metabolites resemble either nucleobases or nucleosides (a nucleotide without the phosphate group), but have altered chemical groups. These drugs exert their effect by either blocking the enzymes required for DNA synthesis or becoming incorporated into DNA or RNA. By inhibiting the enzymes involved in DNA synthesis, they prevent mitosis because the DNA cannot duplicate itself. Also, after misincorporation of the molecules into DNA, DNA damage can occur and programmed cell death (apoptosis) is induced. Unlike alkylating agents, anti-metabolites are cell cycle dependent. This means that they only work during a specific part of the cell cycle, in this case S-phase (the DNA synthesis phase). For this reason, at a certain dose, the effect plateaus and proportionally no more cell death occurs with increased doses. Subtypes of the anti-metabolites are the anti-folates, fluoropyrimidines, deoxynucleoside analogues and thiopurines.

The anti-folates include methotrexate and pemetrexed. Methotrexate inhibits dihydrofolate reductase (DHFR), an enzyme that regenerates tetrahydrofolate from dihydrofolate. When the enzyme is inhibited by methotrexate, the cellular levels of folate coenzymes diminish. These are required for thymidylate and purine production, which are both essential for DNA synthesis and cell division. Pemetrexed is another anti-metabolite that affects purine and pyrimidine production, and therefore also inhibits DNA synthesis. It primarily inhibits the enzyme thymidylate synthase, but also has effects on DHFR, aminoimidazole carboxamide ribonucleotide formyltransferase and glycinamide ribonucleotide formyltransferase. The fluoropyrimidines include fluorouracil and capecitabine. Fluorouracil is a nucleobase analogue that is metabolised in cells to form at least two active products; 5-fluourouridine monophosphate (FUMP) and 5-fluoro-2'-deoxyuridine 5'-phosphate (fdUMP). FUMP becomes incorporated into RNA and fdUMP inhibits the enzyme thymidylate synthase; both of which lead to cell death. Capecitabine is a prodrug of 5-fluorouracil that is broken down in cells to produce the active drug. The deoxynucleoside analogues include cytarabine, gemcitabine, decitabine, Vidaza, fludarabine, nelarabine, cladribine, clofarabine and pentostatin. The thiopurines include thioguanine and mercaptopurine.

Anti-microtubule agents are plant-derived chemicals that block cell division by preventing microtubule function. Microtubules are an important cellular structure composed of two proteins; α-tubulin and β-tubulin. They are hollow rod shaped structures that are required for cell division, among other cellular functions. Microtubules are dynamic structures, which means that they are permanently in a state of assembly and disassembly. Vinca alkaloids and taxanes are the two main groups of anti-microtubule agents, and although both of these groups of drugs cause microtubule disfunction, their mechanisms of action are completely opposite. The vinca alkaloids prevent the formation of the microtubules, whereas the taxanes prevent the microtubule disassembly. By doing so, they prevent the cancer cells from completing mitosis. Following this, cell cycle arrest occurs, which induces programmed cell death (apoptosis). Also, these drugs can affect blood vessel growth; an essential process that tumors utilize in order to grow and metastasize.

Vinca alkaloids are derived from the Madagascar periwinkle, Catharanthus roseus (formerly known as Vinca rosea). They bind to specific sites on tubulin, inhibiting the assembly of tubulin into microtubules. The original vinca alkaloids are completely natural chemicals that include vincristine and vinblastine. Following the success of these drugs, semi-synthetic vinca alkaloids were produced: vinorelbine, vindesine, and vinflunine. These drugs are cell cycle-specific. They bind to the tubulin molecules in S-phase and prevent proper microtubule formation required for M-phase.

Taxanes are natural and semi-synthetic drugs. The first drug of their class, paclitaxel, was originally extracted from the Pacific Yew tree, *Taxus brevifolia*. Now this drug and another in this class, docetaxel, are produced semi-synthetically from a chemical found in the bark of another Yew tree; *Taxus baccata*. These drugs promote microtubule stability, preventing their disassembly. Paclitaxel prevents the cell cycle at the boundary of G2-M, whereas docetaxel exerts its effect during S-phase. Taxanes present difficulties in formulation as medicines because they are poorly soluble in water.

Podophyllotoxin is an anti-neoplastic lignan obtained primarily from the American Mayapple (*Podophyllum peltatum*) and Himalayan Mayapple (*Podophyllum hexandrum* or *Podophyllum emodi*). It has anti-microtubule activity, and its mechanism is similar to that of vinca alkaloids in that they bind to tubulin, inhibiting microtubule formation. Podophyllotoxin is used to produce two other drugs with different mechanisms of action: etoposide and teniposide.

Topoisomerase inhibitors are drugs that affect the activity of two enzymes: topoisomerase I and topoisomerase II. When the DNA double-strand helix is unwound, during DNA replication or transcription, for example, the adjacent unopened DNA winds tighter (supercoils), like opening the middle of a twisted rope. The stress caused by this effect is in part aided by the topoisomerase enzymes. They produce single- or double-strand breaks into DNA, reducing the tension in the DNA strand. This allows the normal unwinding of DNA to occur during replication or transcription. Inhibition of topoisomerase I or II interferes with both of these processes.

Two topoisomerase I inhibitors, irinotecan and topotecan, are semi-synthetically derived from camptothecin, which is obtained from the Chinese ornamental tree *Camptotheca acuminata*. Drugs that target topoisomerase II can be divided into two groups. The topoisomerase II poisons cause increased levels enzymes bound to DNA. This prevents DNA replication and transcription, causes DNA strand breaks, and leads to programmed cell death (apoptosis). These agents include etoposide, doxorubicin, mitoxantrone and teniposide. The second group, catalytic inhibitors, are drugs that block the activity of topoisomerase II, and therefore prevent DNA synthesis and translation because the DNA cannot unwind properly. This group includes novobiocin, merbarone, and aclarubicin, which also have other significant mechanisms of action.

The cytotoxic antibiotics are a varied group of drugs that have various mechanisms of action. The group includes the anthracyclines and other drugs including actinomycin, bleomycin, plicamycin, and mitomycin. Doxorubicin and daunorubicin were the first two anthracyclines, and were obtained from the bacterium *Streptomyces peucetius*. Derivatives of these compounds include epirubicin and idarubicin. Other clinically used drugs in the anthracyline group are pirarubicin, aclarubicin, and mitoxantrone. The mechanisms of anthracyclines include DNA intercalation (molecules insert between the two strands of DNA), generation of highly reactive free radicals that damage intercellular molecules and topoisomerase inhibition.[33] Actinomycin is a complex molecule that intercalates DNA and prevents RNA synthesis. [34] Bleomycin, a glycopeptide isolated from *Streptomyces verticillus*, also intercalates DNA, but produces free radicals that damage DNA. This occurs when bleomycin binds to a metal ion, becomes chemically reduced and reacts with oxygen. Mitomycin is a cytotoxic antibiotic with the ability to alkylate DNA.

III. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

To identify either common/conserved or differential/non-conserved responses to alkylation damage in an unbiased manner, and place them in a functional context, the gene expression profiles in three different cell types from different species was determined: primary non-transformed mouse embryonic fibroblasts (MEF); human breast cancer cells (MDA-MB231); and the evolutionary distant fly Kc167 cells (D. melanogaster). Cells were exposed to methyl-methane-sulfonate (MMS), which is a prototypical mono-functional alkylating agent that attacks mainly purinic sites in DNA by adding methyl groups. In contrast to other alkylating agents, such as cyclophosphamide, carmustine and temozolomide—which require hepatic metabolism to produce fully active intermediates (Jones et al., 1993, Breast Cancer Res Treat 26 Suppl, S11-7; Saleem et al., 2003, Cancer Res 63, 2409-15)—MMS is reactive itself thus being useful for in vitro studies. The commonalities of survival pathways across species, which was obscured by direct ortholog comparison, was determined by investigating canonical signaling pathways. Gene and pathway changes necessary for survival were validated at a protein level with functional experiments and metabolomics. In fly cells, results from transcriptional responses were fused with previously described RNAi genomic screen to reveal pathway components involved in MMS survival (Ravi et al., 2009, PLoS Genet 5, e1000527). The findings from MMS were extended to other alkylating agents as 4-hydroperoxycyclophosphamide (4-HC), temozolomide (TMZ) and the alkylation-like cisplatin (CDDP) to address the class effect.

Cross-species, cross-platform alkylating damage responses do not overlap at the gene level but are conserved at a pathway level. RNAi screening was used in Drosophila cells to identify genes and pathways involved in surviving alkylation damage (Ravi et al., 2009, PLoS Genet 5, e1000527). It was demonstrated that survival factors were conserved from yeast to fly and mouse at a pathway level, if not at an individual gene level.

Gene expression changes were utilized to provide further insight into mammalian alkylation survival mechanisms. By analyzing gene expression profiles of normal MEFs, Drosophila, and breast cancer cells exposed to MMS, the first confounding factor was that there was no consistent number of DEG (differentially expressed genes) that overlap across species (by comparing orthologs of fly, mouse and human) (FIG. 1A). MMS altered expression of approximately 4 to 11% of genes, across the platforms, and a low enrichment for overlapping genes (0.6 to 9.9%) was observed independently on comparison of up- and down-regulated DEGs (FIG. 1A). For instance, among more than 1800 up-regulated gene entities across the three species only the orthologs of glutamate-cysteine ligase catalytic subunit (GCLC), glutamine synthetase (GLUL), and the cell growth inhibitor GADD45B overlapped. Obviously one issue with this type of cross-species analysis is the loss of gene numbers due to lack of ortholog conservation when converting a gene from human/mouse to fly orthologs and vice versa. For example, when converting MMS up-regulated genes in human/mouse to fly orthologs, almost 70% of genes did not possess orthologs in fly (FIG. 1A, left table).

In a second approach, published RNAi screening for MMS survival genes in fly cells was used (Ravi et al., 2009, PLoS Genet 5, e1000527), and the overlap between RNAi hits with DEGs in fly microarrays were tested. Noteworthy, the ability to fuse gene expression and RNAi screen data has been a longstanding challenge in the field; various studies have observed that there is no significant overlap between the genes that confer a phenotype when knocked out or knockdown and the genes that are transcriptionally regulated in the same context (Fry et al., 2005, Annu Rev Microbiol 59, 357-77; Walhout et al., 2002, Curr Biol 12, 1952-8). The same lack of overlap (overlap ~2%) was observed when comparing with previously published RNAi screen hits and the gene expression changes induced 8 and 24 h after MMS exposure in Kc167 cells.

Since gene level overlap was not a good strategy to analyze this type of data, a systems biology approach to look for commonalities and differences of the cellular processes/pathways modulated by MMS was used. First, understanding that genes with many potentially relevant survival pathways (for example DDR and metabolic pathways) are regulated mostly at a post-translational level instead of gene expression—which would not be detected by microarrays/RNAseq—the RNAi screen hits and DEGs lists were independently analyzed. Then, RNAi screening hits were fused with MMS-induced genes and pathway enrichment was studied. This herein named "Fusion approach" permitted detection of not only previously validated alkylation survival pathways (Ravi et al., 2009, PLoS Genet 5, e1000527) in Drosophila cells such as proteasome, NER, Notch and p53 (whose genes were mostly not regulated at mRNA expression), but also allowed higher gene enrichment for pathways as glutathione, p53, DNA repair, and mTOR signaling as well as to detect some previously unidentified pathways as "nucleotide metabolism" among others. Thus, fusion of RNAi hits and gene expression changes were used to analyze MMS responses in fly.

Figure 1B:
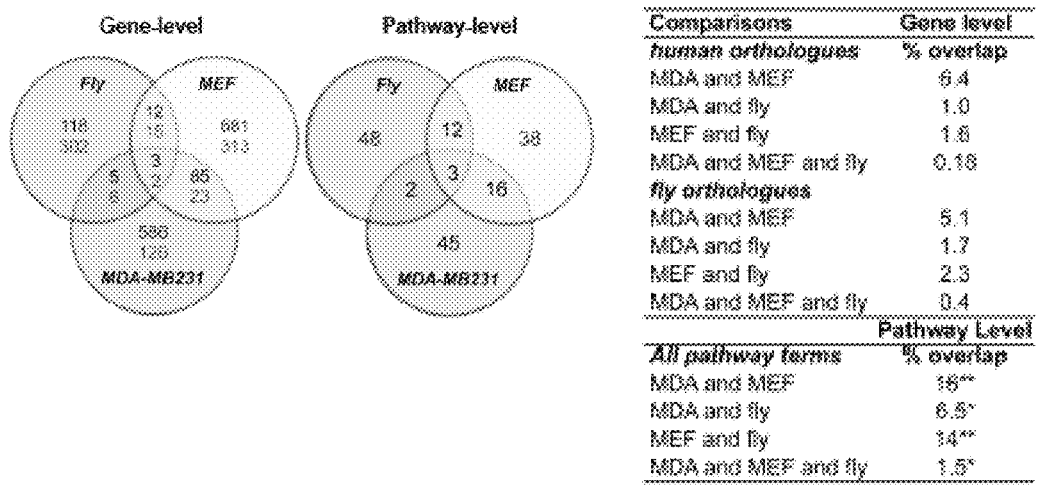
Figure 1C:
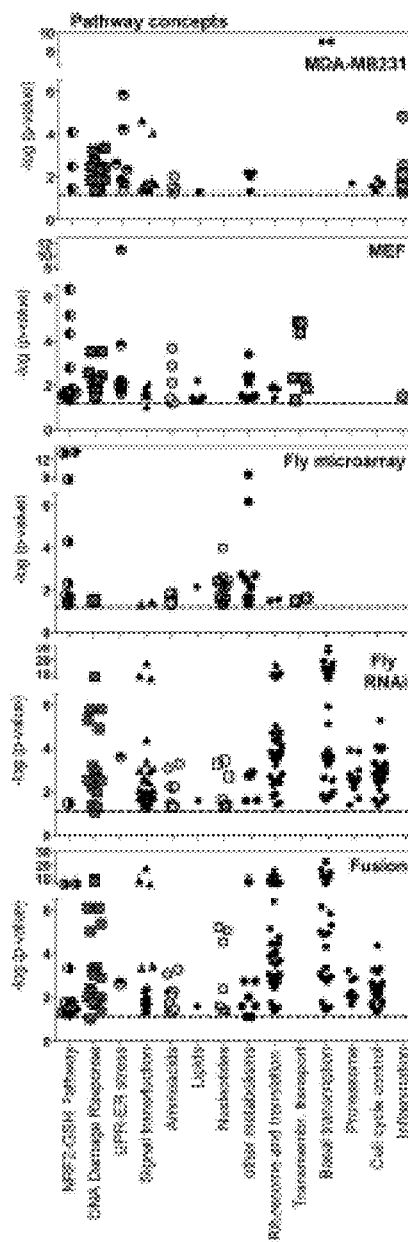
Figure 1D:
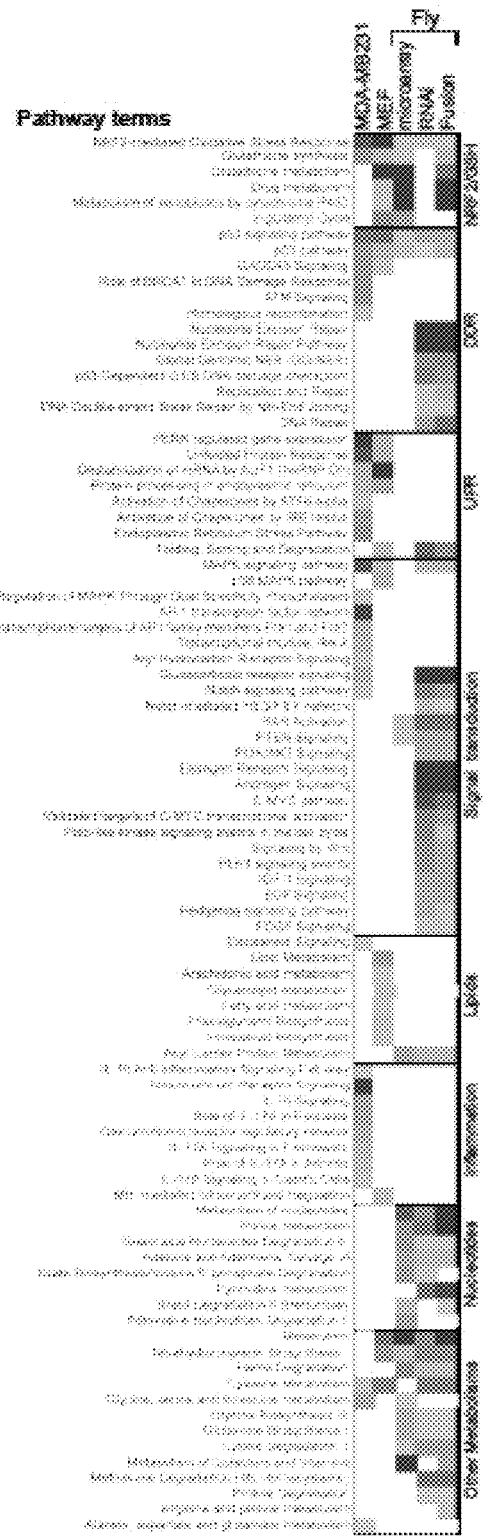
Figure 1E:
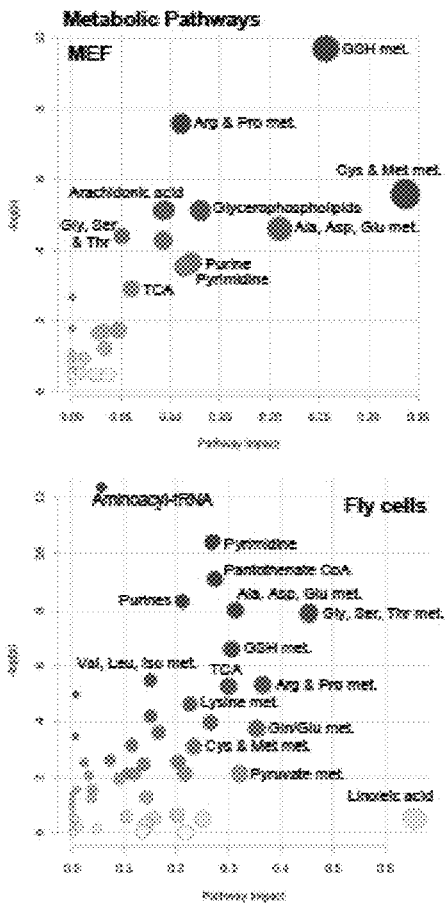
Figure 1F:
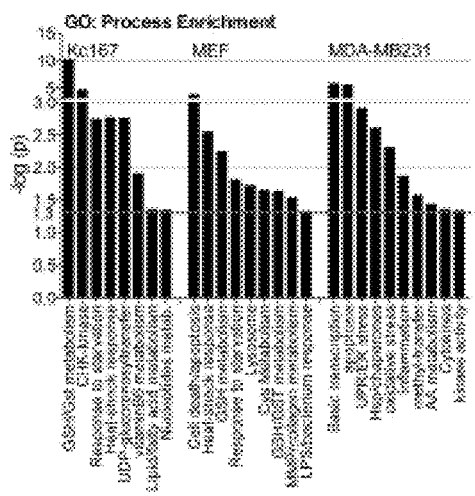

Although gene level comparisons were fruitless, gene Ontology Clustering and Pathway Enrichment Analyses revealed common and differentially activated biological pathways in response to MMS across species (FIGS. 1B and 1D). Besides the expected DNA damage pathways (such as p53 related terms), a significant enrichment in NRF2, glutathione synthesis and GSH-dependent detoxification, Unfolded Protein Responses (UPR) and Endoplasmic reticulum (ER) stress pathways were identified as common responses across the three cell types independent on their tumoral status (FIG. 1B).

Figure 2A:
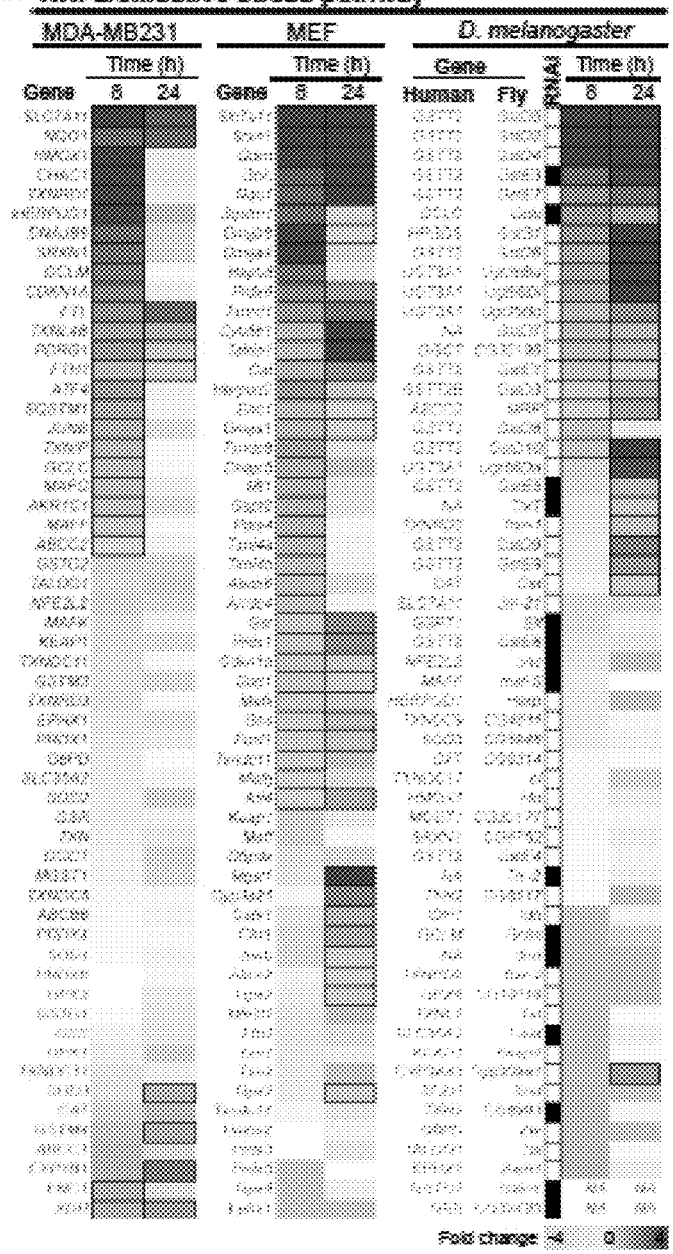
FIG. 2. NRF2 controls GSH production required for alkylation survival. (A) Heatmap representation of MMS effect on expression of genes associated with NRF2 and oxidative stress biological pathways in microarray/RNAseq experiments. Significantly up/downregulated genes are black squared (T-test, $p<0.05$). Survival hits with the RNAi screening in Kc167 fly cells are highlighted (full-black boxes). NA: Not accessed gene/absent orthologue. (B) DCF assays showing the ROS production in alkylating agents-treated cells treatments (12 h incubation). (C) Cell viability in Kc167, MEF and MDA-MD231 cells after 48 h treatment. (D) Effect of modulators of ROS and GSH precursors on glutathione content after 12 h MMS treatment. (E) Metabolomics assays showing the effect of MMS on content of metabolites involved in GSH de novo biosynthesis and GSH-dependent detoxification in MEF and Kc167 cells. (F) Western blots showing the effect of MMS and other alkylating agents on total and nuclear NRF2 and GCLC protein contents in breast cancer cell lines (MDA-MB231, MCF-7) and MEF; siRNA-mediated NRF2 knockdown validation. (G) Effect of NRF2 knockdown on glutathione production in breast cancer cell lines. F and G experiments were performed after 8-12 h treatment. (H) Alkylating agents decrease the content of protein sulfhydryl (protein-SH) groups. Cells were treated for 12 h with different concentrations of MMS, TMZ, 4-HC and CDDP and protein-SH groups were detected through derivatization with dibromobimane as described in Materials and methods. (I) NRF2 knockdown enhanced the sensitivity of cancer cells to alkylating agents. Legends: T (200 µM Trolox); NAC (N-acetyl-cysteine 7.5 mM), GSH-E (GSH-ethyl-ester, 10 mM); BSO (2.5 mM); $H_2O_2$ (1 mM); CHX (Cycloheximide, 1 µg/mL) Actino (Actinomycin D, 5 µg/mL); ctrl si (scrambled siRNA, negative control); CDDP (cisplatin, 75 µM); TMZ (temozolomide 1.5 mM), 4HC (4-hydroperoxy-cyclophosphamide, 75 µM). Data are represented as mean±SEM. *different from untreated cells; #different from untreated and from MMS/alkylating agent-treated cells ($n\geq3$; $p<0.05$, ANOVA).
Figure 3A:
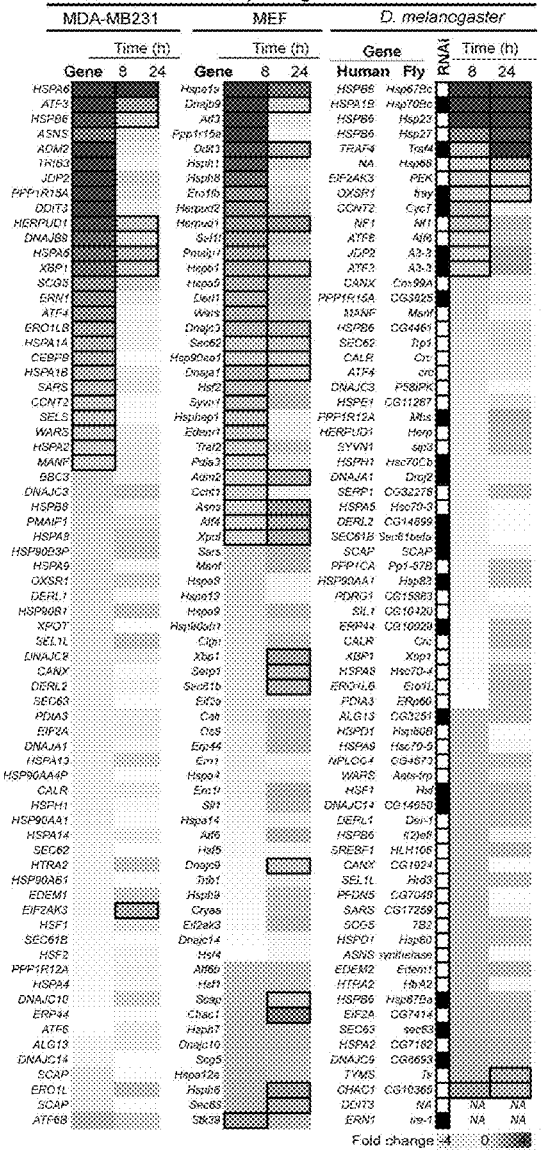
FIG. 3. UPR-ER stress controls cell survival to alkylation insult across species. (A) Heatmap representation of MMS effect on expression of genes associated with UPR/ER stress from microarray/RNAseq experiments. Significantly up/downregulated genes are black squared (t-test, p<0.05). Survival hits with the RNAi screening in Kc167 fly cells are highlighted (full-black boxes). NA: Not accessed gene/absent orthologue. (B) Western blots showing the effect of MMS on ER sensors PERK and IRE1a phosphorylation status, ATF6 cleavage and their downstream CHOP, ATF3 and BiP/GRP78 immunocontent in MEF and breast cancer cell lines (8 h treatment); and time-course effect of MMS on ER stress sensors activation in MDA-MB231 cells; (C) Effect of ER stress sensors and NRF2 knockdown on NRF2, CHOP and GRP78/BiP in MDA-MB231 cells treated for 8 h; (D) Effect of NAC pre-treatment on activation/content of ER stress markers in MDA-MB231 cells (8 h treatment). (E) NRF2 knockdown extended the ER stress marker activation after 24 h MMS treatment; and the rescue effect of 7.5 mM NAC pre-treatment. (F) Western blots showing the effect of TMZ, 4-HC and CDDP on induction of ER stress activation markers in MDA-MB231 cells after 24 h treatment. Effect of ER stress sensors and NRF2 knockdown on: (G) sensitivity of cancer cells to alkylating agents and, (H) effector caspase-3/7 activation. Proteins of interest were knockdown with siRNAs followed by 48 h treatments with alkylating agents. Data are represented as mean±SEM NAC (N-acetyl-cysteine 7.5 mM); ctrl si (scrambled siRNA negative control); CDDP (cisplatin, 75 µM); TMZ (temozolomide 1.5 mM); 4HC (4-hydroperoxycyclophosphamide, 75 µM). Legends: *different from untreated cells; #different from untreated and from MMS/alkylating agent treated cells (n≥3; p<0.05, ANOVA).

Within the NRF2-glutathione pathway, fly cells up-regulated several glutathione S-transferases orthologs (Gst), Gclc and Glul. Though the genes involved in de novo GSH synthesis from glutamine and cysteine (GLUL, GCLC and GCLM) also displayed increased expression in MDA- MB231, the GSTs were not induced instead (FIG. 2A). With the UPR pathway, gene ontology analysis of Kc167 *Drosophila* gene expression revealed several heat-shock proteins (Hsp), while a number of pathway terms involving the UPR-mediated ER stress response (UPR/ER stress), including XBP-1, PPP1R15A, ASNS, ATF4 and HSPA5 were readily detected as up-regulated in mammalian, MEFs and MDA-MB231 (FIGS. 1B and 1D, and FIG. 3A).

Amongst the differentially activated responses ("non-conserved"), the comparative analysis of pathway also revealed a number of pathways terms involved in inflammation, including genes belonging to the extracellular matrix metalloproteinases (MMP10, MMP13, MMP17 in MEFs; MMP1 and MMP3 in MDA-MB231), the cytokine/chemokine family (IL8, CXCL3, IL1A, CCL20, CXCL2 in MDA-MB231) and other inflammatory genes such as PTGS2 (the COX-2 enzyme gene) in both MEF and MDA-MB231, which did not stand out in fly cells (FIG. 1B). A number of signal transduction pathways (MAPKs, AP-1 and NFκB related terms) were also solely enriched in mammalian cells. On the other hand, MMS differentially induced a significant number of metabolic pathways that should modulate amino acids, nucleotides and cofactor metabolism in fly. By comparing metabolomics profiles and Metabolic Pathway Enrichments (FIG. 1C) in MMS-treated MEFs and fly cells, many of the alterations observed by pathway analysis of gene expression data were validated. In fact, GSH, arachidonic/linoleic acids, Cys and Met (sulfur aa) and purine and pyrimidine nucleotide metabolisms were found altered, indicating that the alterations in metabolic pathways detected from gene expression profiling in fact led to changes in the metabolic flow in alkylated cells.

Interestingly, nucleotide pool changes were induced by MMS across species, but when this response in MDA-MB231 and SKBr3 breast cancer cells was examined, it was observed that the types of changes were not consistently the same, presumably because of mutations in the cancer cells that confound this response. Thereafter, the processes that seemed to have the strongest responses—the conserved/common UPR/ER stress, NRF2 pathways, and the non-conserved/differential inflammation were validated and investigated—aiming to shed light on how these pathways affect cell responses to alkylation, their possible crosstalk and whether any of these responses would be useful targets to improve the therapeutic efficacy of alkylating agents in treating cancer.

Glutathione is an Essential Metabolite in Response to Alkylation.

Figure 2B:
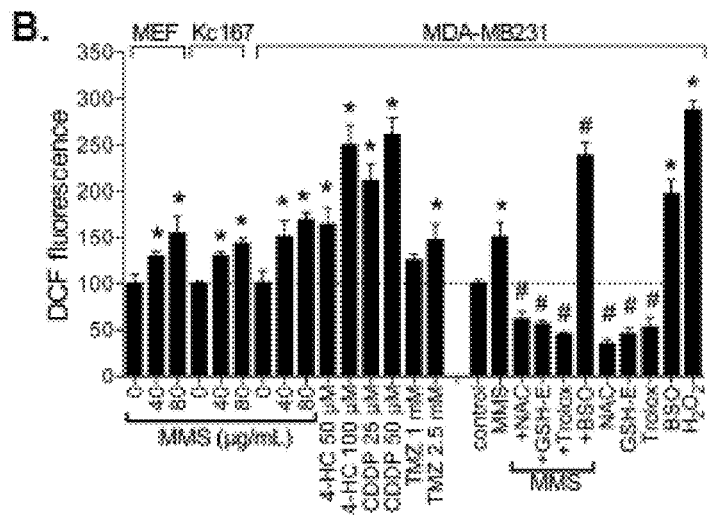

Ravi et al. reported that some genes in the glutathione pathway are important to MMS survival (Ravi et al., 2009, *PLoS Genet* 5, e1000527). Others have described increases in ROS that are associated with MMS exposure in yeast and mammalian cells (Kitanovic et al., 2009, *FEMS Yeast Res* 9, 535-51). ROS production was investigated and a modest (1.5-fold) dose-independent increase in ROS even in response to highly toxic levels of MMS (80 µg/mL; $IC_{90}$ at 24 h) (FIG. 2B) was found. This small increase is consistent with values found in yeast (Rowe et al., 2008, *Free Radic Biol Med* 45, 1167-77). A consistent induction of genes involved in detoxification or production of ROS/RNS such as xanthine oxidase (XOD), nitric oxide synthases (NOS1/2/3), superoxide dismutases (SOD1/2/3) and catalases (CAT) in fly or breast cancer cells was not observed; while MEFs slightly up-regulated CAT (2.7-fold at 24 h) (FIG. 2A). This suggested that the increase in ROS might not be a major component of alkylation-induced death but rather a secondary effect, and perhaps the GSH system, which hugely stood out in gene expression and metabolic pathway analysis across the cell types—is being used for MMS detoxification.

Figure 2C:
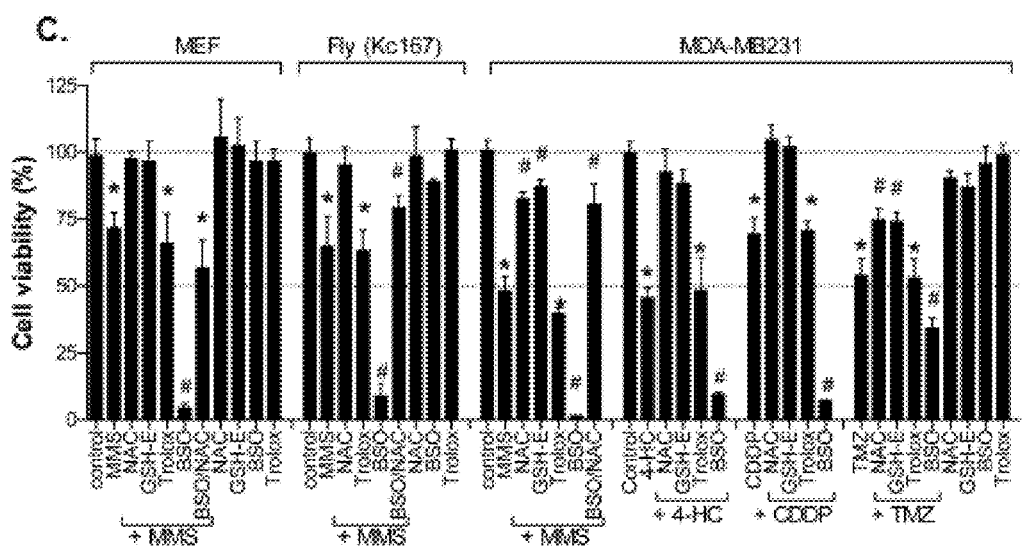
Figure 2D:
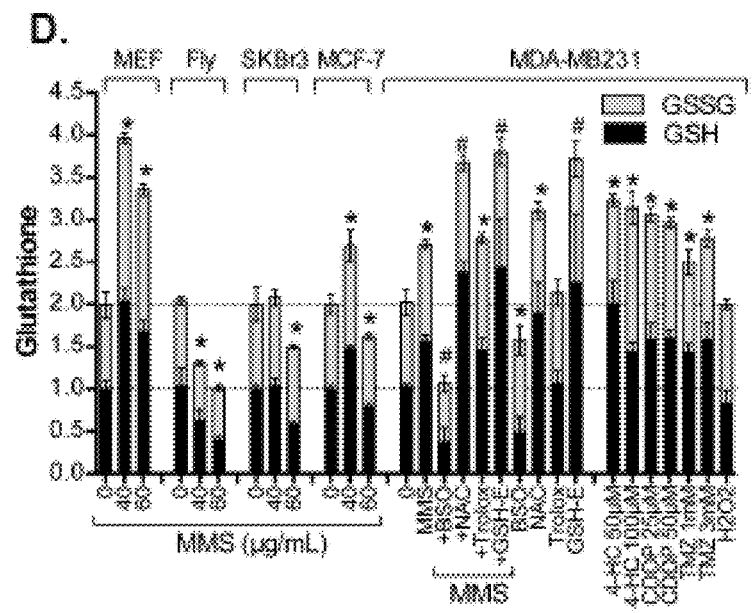

To answer this question, the cells were incubated with two glutathione precursors (NAC and GSH-E), which effectively increased the GSH levels, and a GSH-unrelated antioxidant, Trolox (a vitamin E analogue) (FIG. 2D). All of these agents reduced ROS below levels of the control (FIG. 2B, left side columns), but only the GSH precursors were protective against MMS toxicity in all cell types tested; Trolox had no effect (FIG. 2C). On the other hand, depletion of GSH by BSO—a specific inhibitor of de novo GSH synthesis by gamma-glutamylcysteine synthetase (GCLC/GCLM complex)—caused rapid (from 8 h) and substantial necrotic cell death in MMS-treated Kc167 cells, MEFs, and MDA-MB231 breast cancer cells (FIG. 2C; also observed in SKBr3 and MCF-7—data not shown) with a minor effect on MMS-induced ROS (only 2-fold). In fact, BSO alone, at the dose used (2.5 mM), increased ROS to levels higher than the dose of MMS used (FIG. 2B), but without effect on viability (FIG. 2C). This observation suggests that cells can deal with decreased GSH levels and increased ROS over the short term (up to 48 h), but only in the absence of alkylation exposure. Pretreatment with NAC also rescued the deleterious effects of BSO+MMS combination, strengthening the observation that GSH has a central role in protecting cells against MMS toxicity (FIG. 2C). Similar responses were observed with other alkylators—4-HC, the active metabolite of cyclophosphamide (Malet-Martino et al., 1999, *Curr Pharm Des* 5, 561-86), TMZ and CDDP—; increased ROS (FIG. 2B) and toxicity that was attenuated by NAC and GSH-E, while being potentiated by BSO (FIG. 2C). Therefore, it appears that GSH is key for alkylation survival, but not as an antioxidant.

Figure 2E:
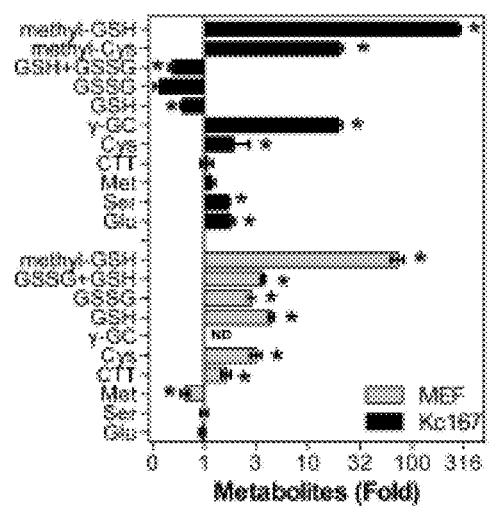
Figure 2F:
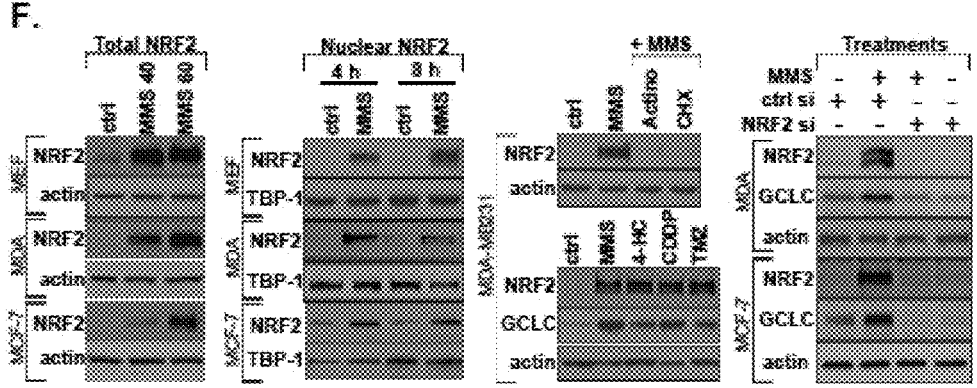
Figure 2G:
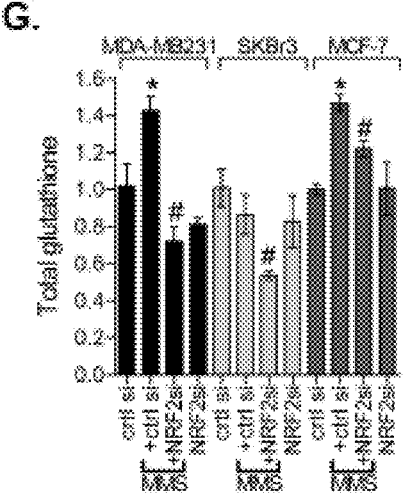
Figure 2H:
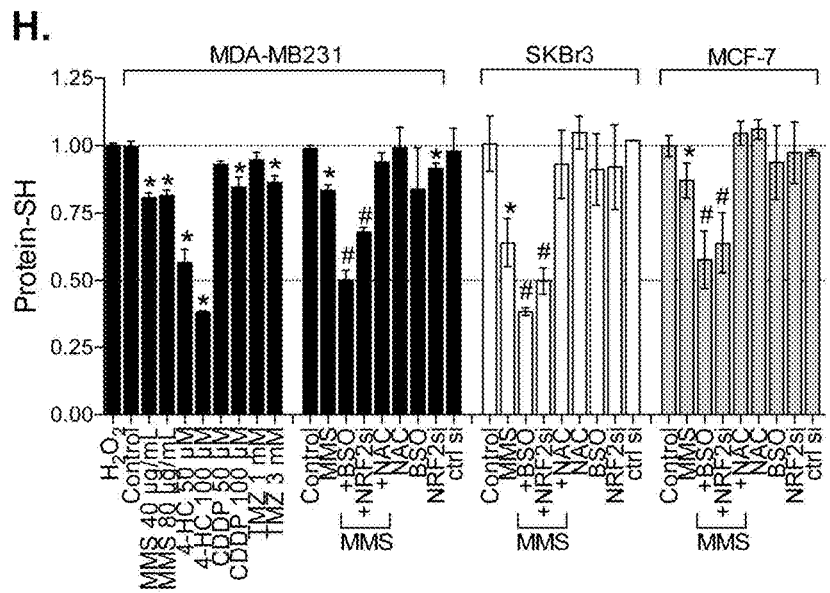

By challenging different cells with different MMS concentrations, it was observed that cells were, in general, able to keep or even increase their total GSH when exposed to lower levels of MMS (40 µg/mL) whereas, higher levels of MMS depleted glutathione metabolites as early as 8 h treatment (FIG. 2D). The other alkylating agents tested also induced GSH synthesis (FIG. 2D). Neither GSSG nor GSSG/GSH ratios were altered, indicating a role for GSH depletion independent on GPx-catalyzed GSH oxidation during peroxide detoxification (data not shown). Since the assay used does not permit the detection of GSH phase-II detoxification conjugates, metabolomics was performed to attempt to identify any other GSH metabolites (FIG. 2E). In both MEF and fly cells MMS resulted in a significant production of methyl-glutathione (methyl-GSH), which is a potential end product of MMS detoxification by transfer of methyl groups from MMS to GSH by GSTs or by direct non-enzymatic alkylation of GSH. In addition, GSH metabolites in fly and mammalian were different. While fly cells apparently have an increased availability of the GSH precursors glutamate (Glu) and Cysteine (Cys), and accumulated levels of gamma-glutamylcysteine (gamma-GC); the absolute levels of glutathione (GSSG and GSH) were depleted, while a high 300-fold increase in methyl-GSH was observed. In MEFs, Glu and Cys precursors did not accumulate but total glutathione (GSH and GSSG) levels were increased. Gamma-GC was not detected and a lower magnitude increase in methyl-GSH (100-fold) was observed (FIG. 2E). Metabolomics also detected an increased level of methyl-cysteine (methyl-Cys) in Kc167 cells. Methyl-Cys is neither an endogenous compound nor a component of any known enzymatic reaction in eukaryotes, but it indicates the reactivity of MMS to form adducts with sulfhydryl groups thus affecting thiol metabolism. In fact, by using Dibromobimane assays, it was observed that MMS and other clinical alkylating agents could react with and deplete protein sulfhydryl residues (FIG. 2H).

NRF2 in the Control of GSH Production and Alkylation Survival.

NRF2 is an important regulator of xenobiotic detoxification and a key regulator of GCLC, the rate-limiting gene in de novo GSH synthesis (Jaramillo, Zhang, 2013, *Genes Dev* 27, 2179-91; Li et al., 2012, *PLoS One* 7, e35122), which is up-regulated by MMS across the three cell types in the study. Pathway analysis (FIG. 1) revealed NRF2 and a number of NRF2 targets involved in protein thiol and GSH homeostasis—including TXNRD1, SRNX1, PRDX6 (thioredoxin, sulfiredoxin and peroxiredoxin family genes, respectively) de novo GSH synthesis (GCLC, GCLM), transporters of GSH precursors (SLC7A11), GSH-S-Transferases (GSTs) and glucoronosyltransferases (UGT family)—as well as other NRF2 classical targets such as NQO1 (NADPH dehydrogenase quinone 1), HMOX1 (heme oxygenase-1), AKR1C1 (aldo-ketoreductase-1), TALDO1 (transaldolase), and FTH1, which were variably up-regulated across species, mostly peaking by 8 hours treatment (FIG. 2A).

Figure 2I:
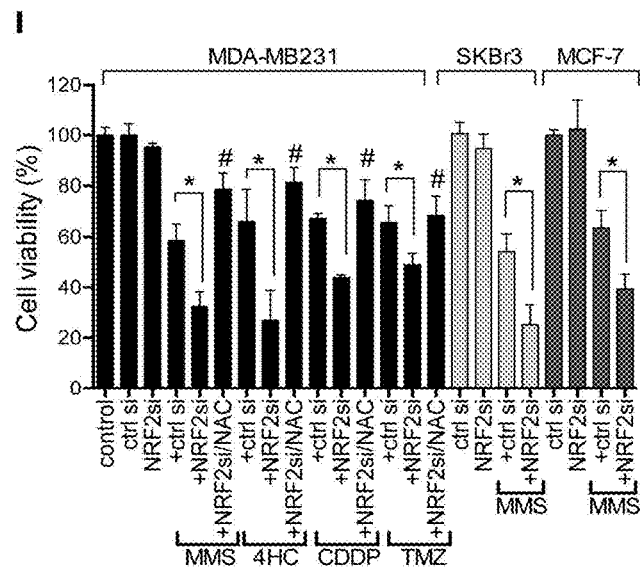

In fact, NRF2 protein levels were barely detectable at unstimulated conditions but rapidly increased in total and nuclear fractions of MMS-treated MEFs, MDA-MB231 and MCF-7 (FIG. 2F) and SkBr3 breast cancer cells (data not shown). Treatment with gene transcription and translation inhibitors (actinomycin D and cycloheximide) blocked NRF2 activation, agreeing with the classical mechanism of NRF2 inhibition by KEAP1-mediated degradation of newly translated NRF2 protein. Silencing of NRF2 blocked MMS-induced GCLC protein accumulation (FIG. 2F) as well as inhibited the increases of GSH by MMS (FIG. 2G). Consequently, silencing of NRF2 mimicked the BSO effect by potentiating MMS-induced cell death in the three cancer cell lines tested (FIG. 2I). TMZ, 4-HC and cisplatin similarly induced NRF2 and GCLC protein (FIG. 2F), while knockdown of this transcription factor also sensitized cells to these chemotherapeutics, suggesting a class effect (FIG. 2I). Silencing of NRF2 while pre-treating cells with NAC rescued alkylation toxicity, suggesting that the deleterious effects of NRF2 knockdown was in fact due to control of the GSH metabolism (FIG. 2H). BSO treatment and NRF2 silencing also potentiated the depletion of protein-SH residues by MMS, suggesting a role for NRF2 and GSH on sulfhydryl groups homeostasis in proteins (FIG. 2H).

Unfolded Protein Survival Responses are Controlled by GSH Pools.

Figure 3B:
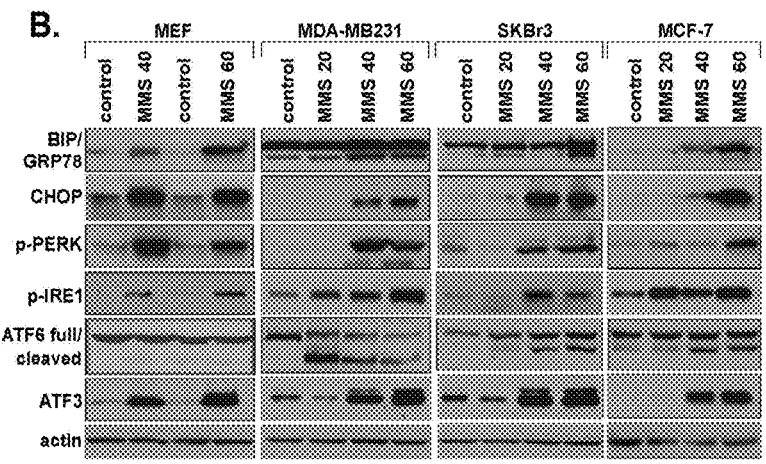

Endoplasmic reticulum (ER) and Heat shock factors (HSFs) are the main sensors for unfolded proteins within a cell. Alterations with the ER luminal homeostasis lead to accumulation of misfolded proteins and UPR-mediated activation of ER-nucleus transduction pathway (Lin et al., 2007, *Science* 318, 944-9; Moore, 1991, *Clin Pharmacokinet* 20, 194-208). The processes activated attempt to restore the balance between protein loading and processing/folding within the ER, but can induce programmed cell death if these attempts fail. The gene expression profiles of MMS-treated fly, MEF and MDA cells revealed a significant enrichment UPR processes (FIGS. 1B and 1D). In mammalian cells there was a clear induction of genes involved in ER-nucleus signaling transduction such as DDIT3, HSPA5, ASNS, PPP1R15A, ATF3, ERO1LB, TRIB3, DNAJ family proteins, XBP-1 and ATF4 amongst others (FIG. 3A). ER stress appears to be an early and transient process in MMS alkylated cells, with most genes being up-regulated within 8 h and returning to basal or even suppressed levels by 24 h (FIG. 3A). The activation status of the three classical ER stress sensors (IRE1a, PERK and ATF6) was observed and the levels of their downstream effectors (GRP78/BIP, CHOP and ATF3) increased by 8 h in MEFs and breast cancer cells; sensors activation decreased to basal levels after 24 h MMS exposure as assessed in MDA-MB231 (FIG. 3B).

Figure 3C:
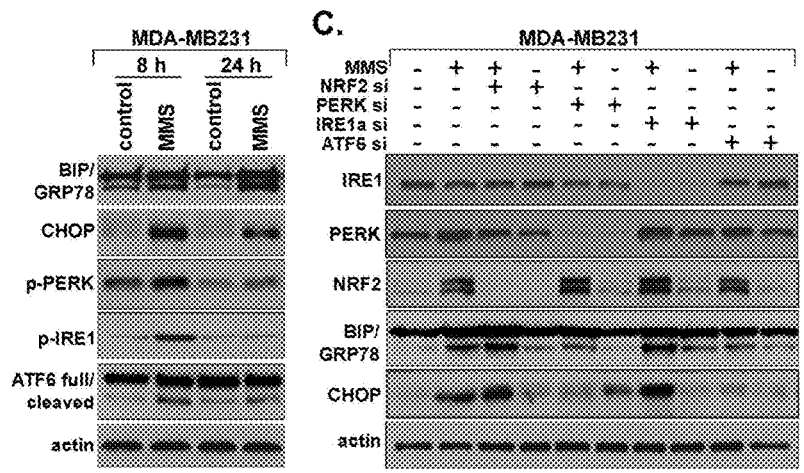
Figure 3D:
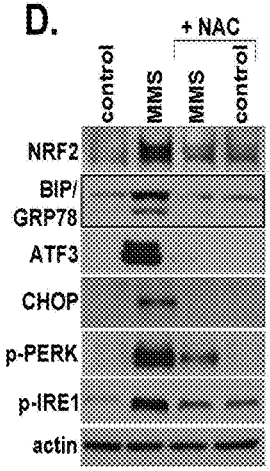
Figure 3E:
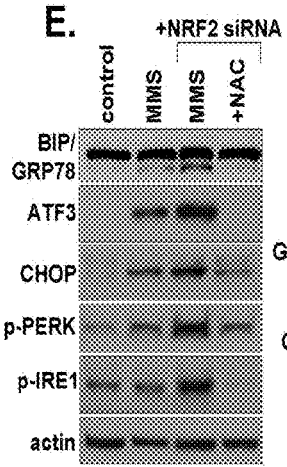
Figure 3F:
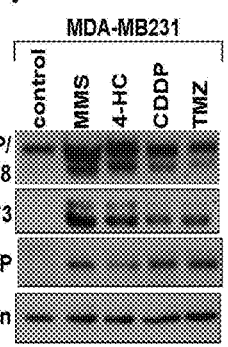

Although there is a myriad of possible ER stress downstream signals and crosstalk, the role of ER stress in NRF2 activation were studied since it has been shown that PERK may promote phosphorylation-mediated NRF2 dissociation from KEAP1, followed by NRF2 nuclear translocation to protect cells from apoptosis (Cullinan et al., 2003, *Mol Cell Biol* 23, 7198-209). Firstly, the three sensors of ER stress (PERK, IRE1a and ATF6) were silenced. Induction of NRF2 by MMS was not altered, in contrast to other classical downstream targets, CHOP and GRP78/BIP (FIG. 3C). This result indicates that activation of NRF2 by MMS is not under the control of ER stress machinery. Increasing the basal levels of GSH with NAC was enough to block both NRF2 activation and ER stress caused by MMS (FIG. 1D). Interestingly, MMS-induced NRF2 activation seems to alter the lasting/magnitude of ER stress, since silencing of NRF2 increased the levels of ER stress markers (CHOP, GRP78, ATF3) and prolonged phosphorylation of PERK and IRE1a compared to MMS alone as assessed after 24 h treatment. Again, the effect of NRF2 silencing on ER stress could be overcome by NAC pre-incubation, suggesting that NRF2-dependent GSH production works as a buffer not only for MMS detoxification but also indirectly controls the timing of ER stress (FIG. 1E). 4-HC, TMZ, and CDDP also increased the immunocontent of ER stress markers in cancer cells, suggesting a commonality of UPR responses to different alkylation compounds (FIG. 1F); an effect also observed for TMZ in glioma cells (unpublished data).

Figure 3G:
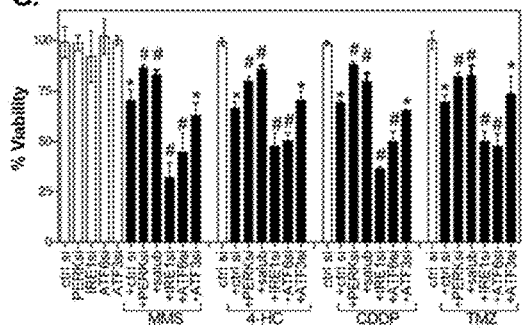
Figure 3H:
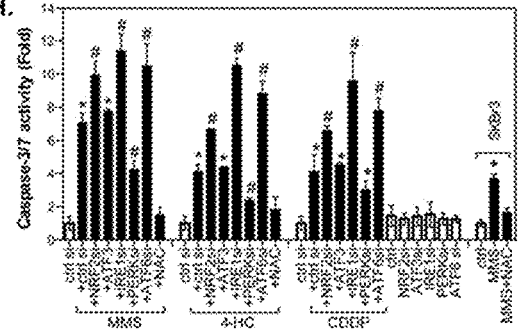

Given that the different ER stress sensors play different roles to determine cell fate during ER stress, therefore how these sensors mediate the balance between life and death during alkylation treatment was investigated. Knockdown of PERK provided protection whereas IRE1a and ATF6 knockdown potentiated alkylation toxicity caused by MMS, 4-HC, TMZ and CDDP in MDA-MB231 cells (FIG. 3G). This pattern was similar in SKBr3 and MCF-7 cell lines (data not shown). Blocking of NRF2, IRE1a and ATF6 responses potentiated caspases-3/7 activation induced by alkylators. In contrast, PERK silencing attenuated caspase-3/7, suggesting a commitment of the PERK sub-pathway with the apoptotic induction by alkylation exposure (FIG. 3H). Notably, caspase-3/7 activation in MCF-7 cells was not detected and, though caspase-3/7 activation by MMS has been detected in SKBr3, these cells presented increased vacuolization following alkylation treatment (data not shown). These observations show that even though ER sensors and NRF2 have a conserved role as determined by overall cell viability assays, the mechanisms of cell death may vary depending on intrinsic cell programs. Overall, it appears that the NRF2-GSH and UPR/ER stress response pathways are essential components of alkylation survival that have been conserved across tumor and non-tumor cell types independent of the species they originated from. The balance of each pathway dictates the outcome of alkylation damage survival, but each pathway appears to be utilized independently.

Essentiality of NRF2-GSH and UPR Pathways for Survival in Fly Cells.

It has been described that activation of NRF2 play a key role in antioxidant and detoxification responses, and increases lifespan in *D. melanogaster* (Sykiotis and Bohmann, 2008, *Dev Cell* 14 (1), 76-85). To study the survival role of NRF2-GSH and UPR pathways in fly cells in the context of alkylation, the microarray/RNAi fusion approach was used, and built into gene/protein interactions networks and landscape analysis in order to have a better coverage of relevant genes besides to identify functional clusters. Gene-by-gene comparison revealed no enrichment at an individual gene basis since only a few fly gene entities (GstE3, GstE5, Gclc and TrxT) were both up-regulated in microarrays and survival hits in the RNAi screen.

Figure 4:
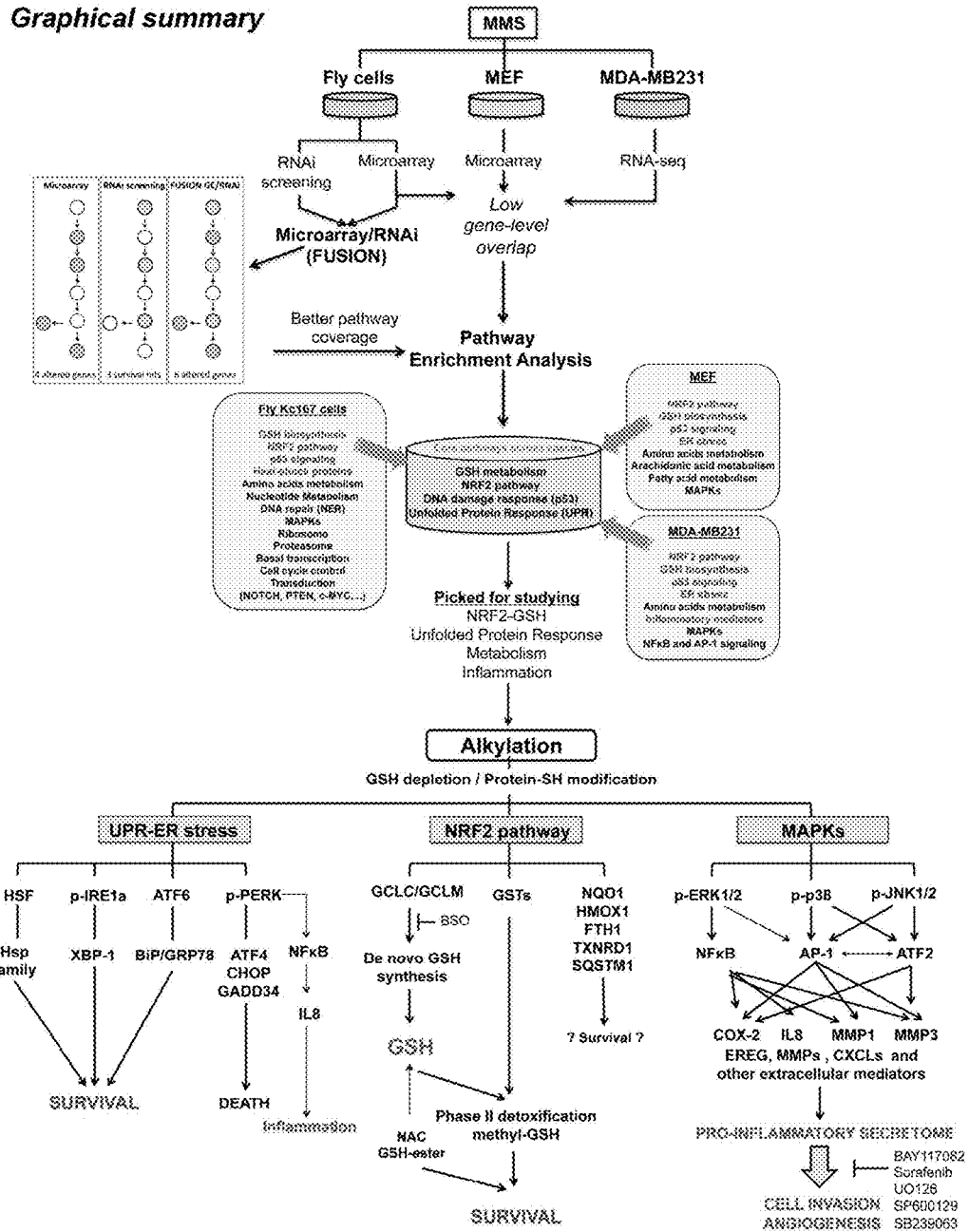
FIG. 4. Gene/Protein interaction networks of NRF2-GSH and UPR pathways in *Drosophila* cells. Fusion of gene expression profiles and RNAi screening hits applied to functional networks shows a landscape of overexpressed and lethal components with the (A) NRF2 and (B) UPR/ER stress response pathway in Kc167 cells treated with MMS for 8 and 24 h. ViaComplex landscapes revealed clusters of pathway activity in response to alkylation.

ViaComplex pinpointed the induction of a highly connected and up-regulated gene cluster comprising several Gst orthologues. While GstE3 and GstE5 were both up-regulated at gene expression and were survival hits in the RNAi screen, other Gst were highly up-regulated in microarrays, though they were not essential for cell survival. Other group of genes such as the *D. melanogaster* NFE2L2/NRF2 orthologue (Deng, 2013, *Fly (Austin)* 8, 2014; 8(1):7-12) (Cap n' Collar (cnc) gene), the NRF2 transcriptional co-activator maf-S, the rate limiting enzyme of GSH synthesis (Gclm and CG32495/human GSS orthologue) and some thioredoxins (Trx-2; CG8993, dhd and CG8517), though not modulated at gene expression level, potentiated MMS toxicity when knock downed in Kc167 cells (FIG. 4). These results altogether point a commitment of NRF2 regulators and GSH-dependent detoxification pathways on cell resistance to alkylation.

Regarding the UPR, while mammalian cells induced classical ER stress transducers, fly cells responded with consistent activation of a heat-shock proteins cluster (Hsp67Bc, Hsp70Bc, Hsp23, Hsp26, Hsp27 among others; FIG. 4B), corroborating with the early identified in GO enrichment analysis (see FIG. 1D). It was observed, many UPR genes—whose expression was not affected by MMS—that could confer lethality to alkylation if knocked down (FIG. 4B). With the heat-shock proteins, fly cells were sensitized to MMS when Hsp83, Hsp70Bc and the upstream regulator heat-shock factor-1 (Hsf, human HSF1 fly orthologue) were knocked down as shown in the protein interaction networks. In the ER stress pathway, silencing of Ire-1 and some Ire-1-regulated DNAJ family of chaperones such as CG14650 and CG6693 potentiated MMS toxicity, agreeing with the role of Ire-1 axis in survival responses to MMS observed in MDA-MB231 cells. The PPP1R15A/Gadd34 fly orthologue CG3825, which is involved in eIF2a dephosphorylation and translation recovery (Ma, Hendershot, 2003, *J Biol Chem* 278, 34864-73; Novoa et al., 2001, *J Cell Biol* 153, 1011-22), and A3-3 (human ATF3 orthologue) also conferred sensitivity to MMS when knocked down. Further, a group of ER proteins involved in ER loading and transport of unfolded/nascent proteins such as Sec61b and Sec63, and the ER resident chaperones CG14512 (ALG13 fly orthologue) and SCAP, were hits in RNAi screen but not modulated at the gene expression level. Interestingly, MDA-MB231 cells expressed high basal levels of HSFs, HSP90 and HSP70s transcripts (by RNA-seq) but did not display further increases in expression of them in response to MMS. Thus, different from mammalian cells, the Hsf-Hsp axis of UPR seems to be a preferential UPR pathway for MMS survival in fly cells compared to ER stress in mammalian.

Inflammatory Pathway is not Conserved Across Species but Favors Cancer Cells Invasion and Angiogenesis.

Figure 5A:
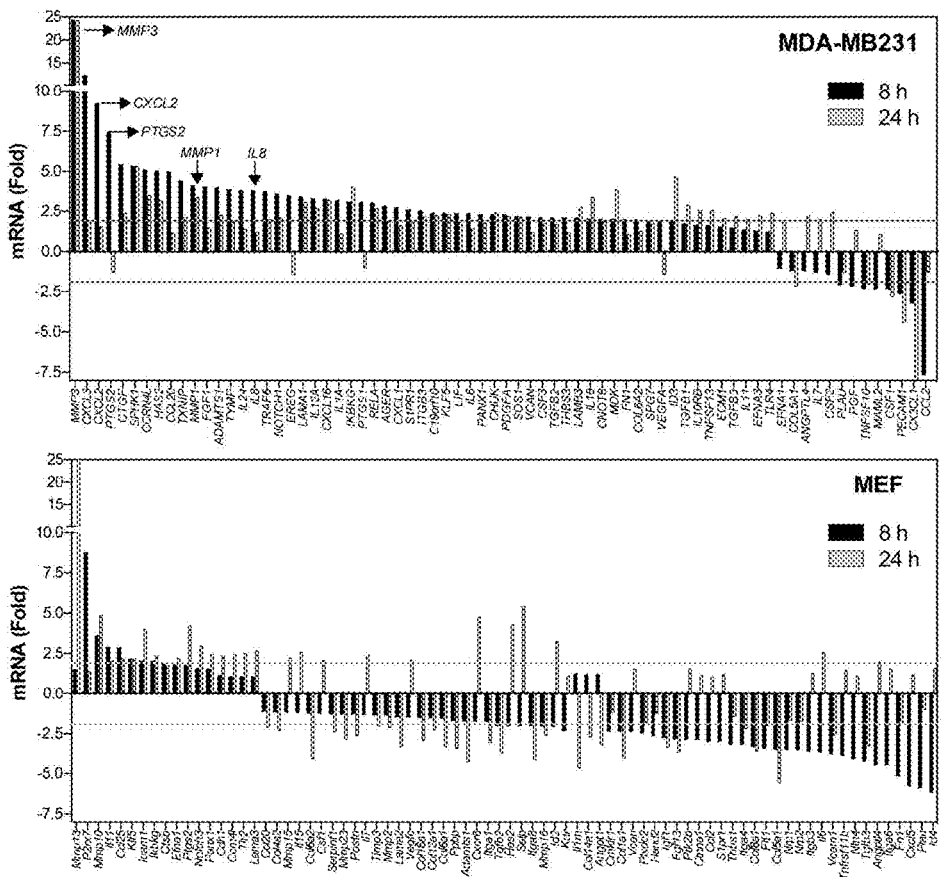
FIG. 5. Validation of the inflammatory response to alkylation. (A) Relative mRNA expression of MMS-induced wound healing/inflammatory genes from MEF and MDA-MB231 cells gene expression profiling arrays. (B) Metabolomics characterization of lipid/fatty acid metabolic clusters in MEF and Kc167 cells. Qualitative heatmaps and quantification of the main metabolites with the prostaglandin synthesis pathway are shown. (C) Validation of the COX-2/prostaglandin pathway in mammalian cells. Western blotting and ELISA assays show that MMS and other alkylating agents increase COX-2 protein and prostaglandin E2 production in MEF and MDA-MB231 cells. (D) Effect of alkylating agents on PGE2 production in different breast cancer cell lines (MDA-MB231, HCC1937, SKBr3, Hs578T and MCF-7). Cells were treated for 12 h and cell lysates and culture medium were collected for western blot and for ELISA assays, respectively. (E) Time-course ELISA experiments showing that MMS enhances the production of MMP1, MMP3 and IL8 in MDA-MB231 cells after 12 h treatment. Data are represented as mean±SEM. *different from untreated cells at the same time-point; #different from untreated and from MMS/alkylating agent-treated cells (n=3; p<0.05, ANOVA).

One of the goals of performing these systematic studies into the mechanisms of damage survival is to identify novel means to potentiate therapies used in the treatment of cancer. Considering the commonality of the NRF2-GSH and UPR/ER stress across species and in both normal and tumor cells, targeting these pathways would likely provide little or no therapeutic advantage in distinguishing normal tissue from cancer cells. Therefore differential responses that appear to be more tumor cell specific were identified. The induction of inflammatory systems was one such MMS-induced response that particularly stood out in the pathway analysis, mainly in cancer cells (FIG. 1B). In mammalian cells, genes such PTGS2 (COX-2 enzyme in MDA-MB231 and MEF), matrix metalloproteinases (MMP1, MMP3, MMP10 in MDA-MB231; MMP12, MMP13, MMP15 and MMP17 in MEFs), interleukins and chemokines (IL8, CXCL2, CXCL3, CCL20, IL1A, IL24 in MDA-MB231; IL6, IL7, IL11, IL15 in MEFs), EGFR/ERBB agonists (EREG/epiregulin in MDA-MB231 and its functional analog AREG/amphiregulin in MEFs) besides other genes involved in inflammatory/wound healing processes were altered in mammalian cells (HAS2, ADAMST, ANGPTL4, NOTCH3/4, P2RX7 among others), but none of them was identified from fly Kc167 cells (FIG. 5A). Four key inflammatory genes (PTGS2/COX-2; MMP1, MMP3 and IL8) were selected to validate and study their mechanisms of induction, and how they impact cell survival during alkylation and if there is anything that distinguishes these responses in tumor cells.

Figure 5B:
Figure 5C:
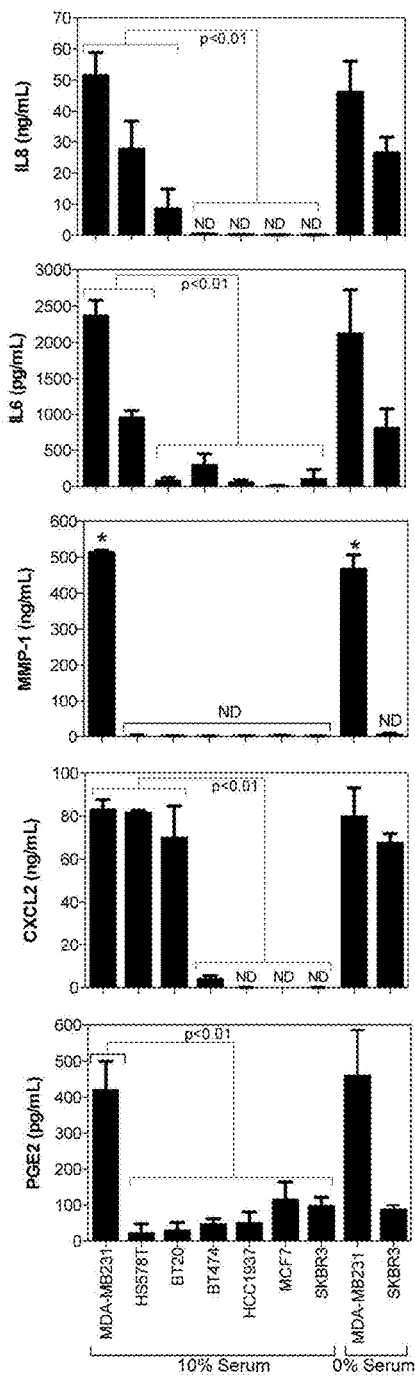
Figure 5D:
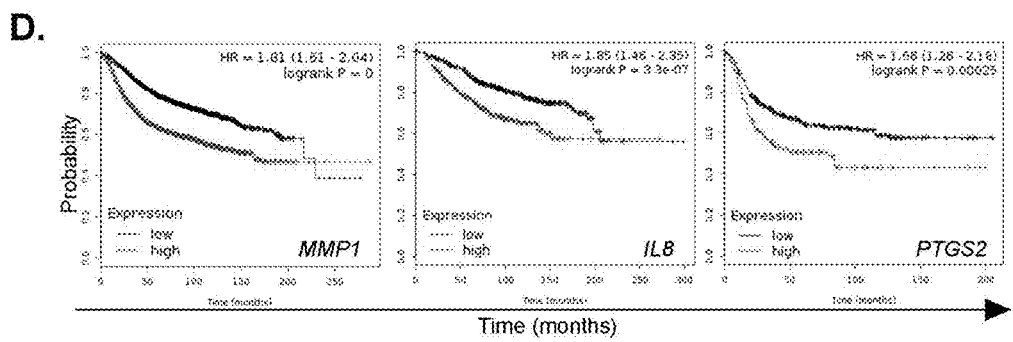
Figure 5E:
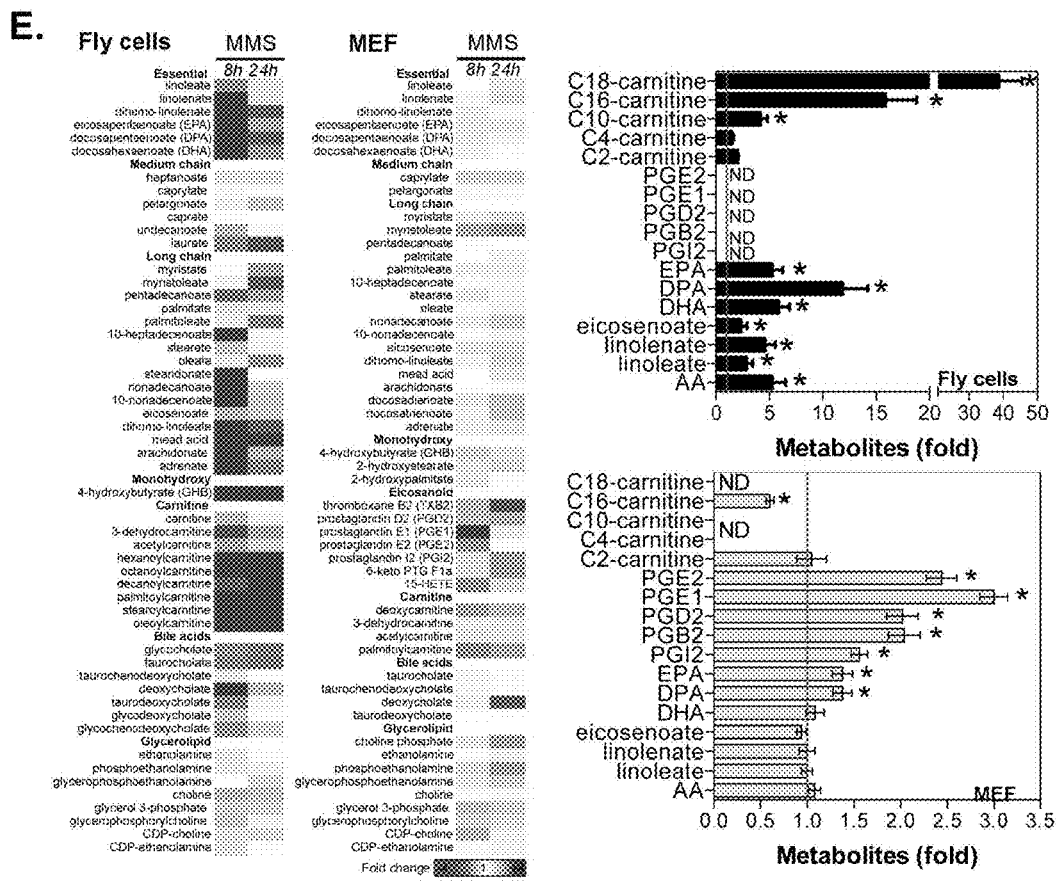
Figure 5I:
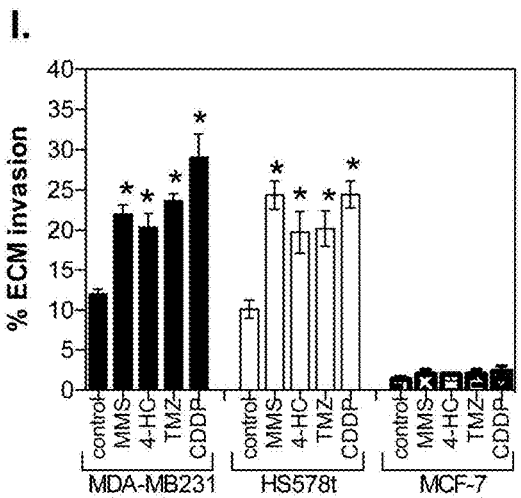
Figure 5J:
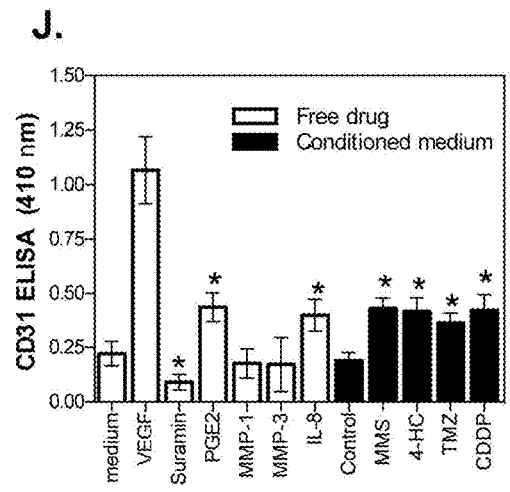

For COX-2, not only pathway enrichment in gene expression analyses in MEFs and MDA-MB231 was observed (FIG. 1B), but also arachidonic/linoleic acid metabolism from metabolomics in MEF but not in fly cells was detected (FIG. 1B). First, taking into account the metabolomics in fly and MEFs, both cell types had an increased mobilization of fatty acids and glycerolipids. Both species displayed a significant increase in the subgroup of unsaturated fatty acid metabolites (linoleic acid, EPA, DHA), typically formed from arachidonic acid (AA) (FIG. 5B). In mammalian, these metabolites are precursors of eicosanoid/prostanoid biosynthesis and, in fact, a concomitant increase in prostaglandin and thromboxane end-products was detected, but only in MEFs (FIG. 5B). In contrast, as *D. melanogaster* genome lacks COX gene (Frolov, Singh, 2012, *PLoS One* 7, e38759; Varvas et al., 2009, *Insect Biochem Mol Biol* 39, 851-60), the fatty acids accumulated appear to be driven to oxidation as indicated from the increased levels of fatty acid-carnitine conjugates, suggestive of mitochondrial transport for oxidation. The alkylation-induced prostaglandin production was also observed in a variety of human cancer cells, with increased levels of prostaglandin E2 (PGE2) detected in culture medium and increased amounts of COX-2 protein in cell lysates following MMS, TMZ, 4-HC and CDDP (FIG. 5C), suggesting a general phenomenon in mammalian cells irrespective of their malignance. The protein levels of IL-8, MMP-1 and MMP-3 were monitored in culture medium from MMS treated MDA-MB231 cells to validate their induction at 8 and 24 h following MMS treatment (FIG. 5D). TMZ, CDDP and 4-HC also increased the production of these molecules.

Figure 6A:
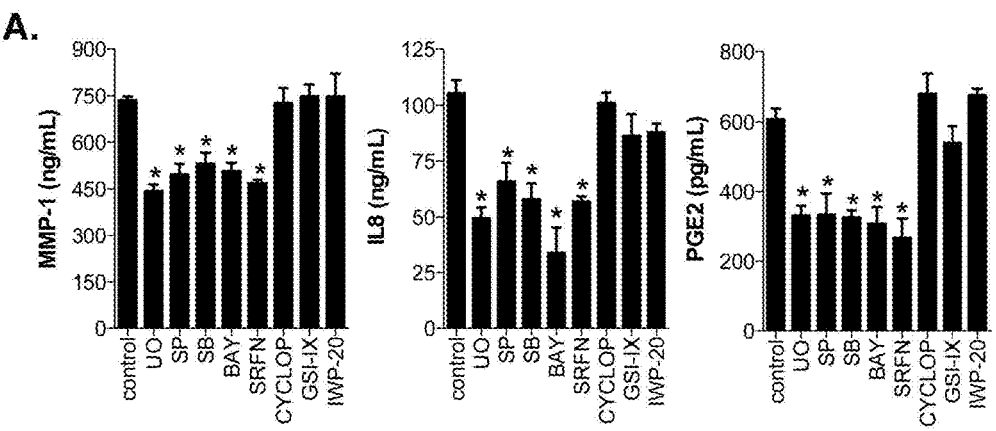
FIG. 6 MAPKs control alkylation-induced inflammatory mediators production in cancer cells. Effect of conditioned media (CM) form alkylating agents-treated MDA-MB231 cells, and effect of MAPKs and IKK/NFκB inhibitors on Boyden chambers invasion (A) and in vitro angiogenesis (B) assays. (C) Putative Transcription Factor Analysis (TFacts) and gene reporter assays (D) showing the effect of alkylating agents on NFκB and AP-1 luciferase promoters in MDA-MB231 cells Effect of pre-incubation with MAPKs inhibitors and siRNA for ER stress and NRF2 on NFκB/AP-1 promoters-driven luciferase activity is also shown. (E) Western blots showing the effect of MMS on phosphorylation of MAPKs (ERK1/2, JNK1/2 and p38) and ATF2 in breast cancer and MEFs after 8 h treatment; right panel: NAC pre-treatment blocked MMS-induced MAPKs and ATF2 phosphorylation and COX-2 induction in MDA-M231 cells. (F) Western blotting assays showing that knockdown of NRF2 and ER stress pathway members did not affect MAPKs activation by MMS in MDA-MB231 cells (8 h treatment) and; MAPK and NFκB inhibitors decreased COX-2 and p-ATF2 protein content without affecting UPR/ER stress and NRF2. (G-J) Effect of MAPKs, IKK/NFκB, ER stress and NRF2 inhibitors/siRNAs on production/release of IL8, MMP1, MMP3 and PGE2 induced by MMS in MDA-MB231. Cells were treated for 12 h and the culture medium was collected for ELISA assays. Data are represented as mean±SEM. *different from untreated cells; #different from untreated and from MMS/alkylating agent treated cells (n=3; p<0.05, ANOVA).
Figures 6B, 6C:
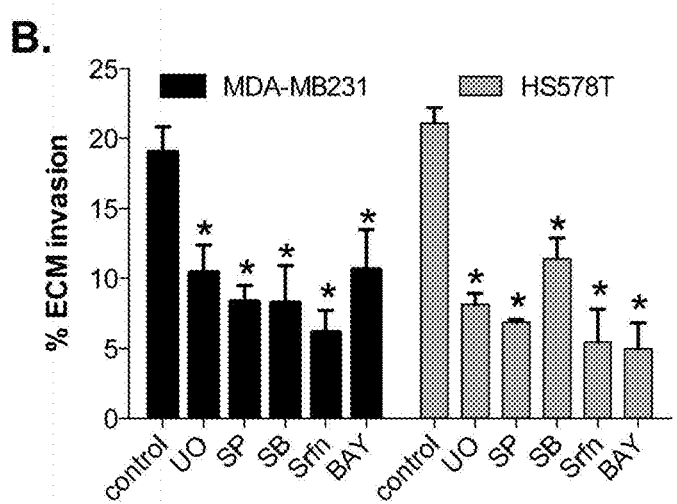

Given that alkylation induced an inflammatory response, the regulation and importance of this pathway in the cell survival or other aspects of tumor biology was explored. First, whether the alkylation-induced inflammatory signals would exacerbate cell invasiveness potential was studied. Conditioned medium (CM) from alkylating agents-treated breast cancer cells stimulated trans-well invasion of MDA-MB231 cells in Boyden Chamber (FIG. 6A, black columns); similar to the effect induced by purified MMP1 and IL8 incubation (FIG. 6A, white columns). Moreover, in an in vitro model of angiogenesis, endothelial cells were stimulated to form CD31-positive vessel-like structures when incubated with CM from alkylated cells (FIG. 6B, black columns) compared to the CM prepared from untreated cells; purified PGE2, IL8 or VEGF also were angiogenic as expected (FIG. 6B, white columns). These results suggest that the inflammatory secretome induced by alkylation may promote phenotypes typical of aggressive cancers.

Figure 6D:
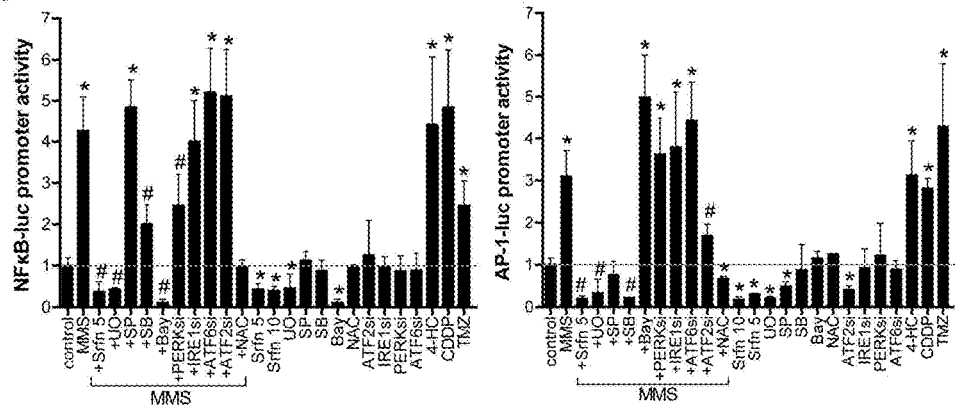

Further, potential transcription factors regulating MMS-induced inflammatory genes and noted NFκB and AP-1 as potentially involved (FIG. 6C) were studied. These transcription factors also stood out in the pathways analysis (FIG. 1B, FIG. 5C). MMS and other alkylating agents activated both NFκB and AP-1 luciferase reporter constructs (FIG. 5D). By testing a small panel of diverse kinase inhibitors, it was observed that the ERK1/2 inhibitor UO126 blocked MMS-induced activation of NFκB and AP-1 reporter constructs while the p38 inhibitor SB203508 only blocked the NFκB reporter. As expected, the JNK1/2-AP-1 inhibitor SP600129 blocked MMS induction of the AP-1 reporter and the IKK inhibitor BAY117082 blocked NFκB promoter activation by MMS. Interestingly, the multikinase inhibitor sorafenib exerted strong inhibitory effects on both promoters (FIG. 6D). On the other hand, silencing of NRF2, and the ER stress sensors IRE1a and ATF6 did not affect activation of either NFκB or AP-1 promoters; PERK silencing caused a minor, though significant, inhibition of MMS-induced NFκB (FIG. 6D). As a control-silencing the AP-1 family member ATF2 (Lopez-Bergami et al., 2010, *Nat Rev Cancer* 10(1), 65-76) decreased AP-1 promoter activation (FIG. 6D).

Figure 6E:
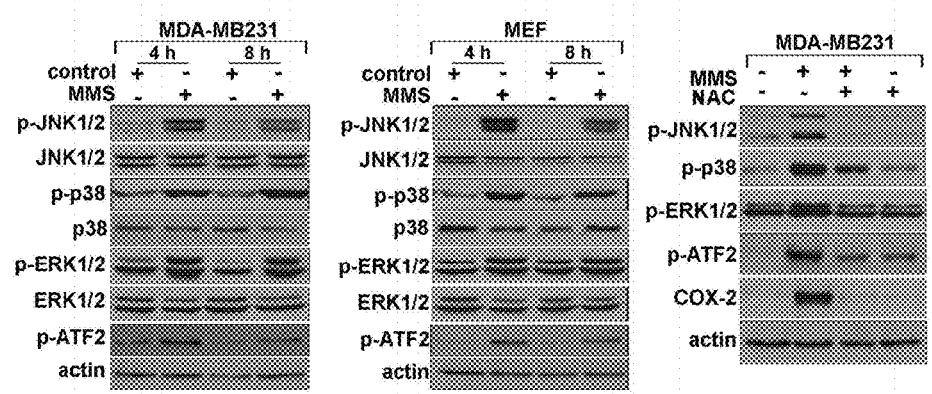
Figure 6F:
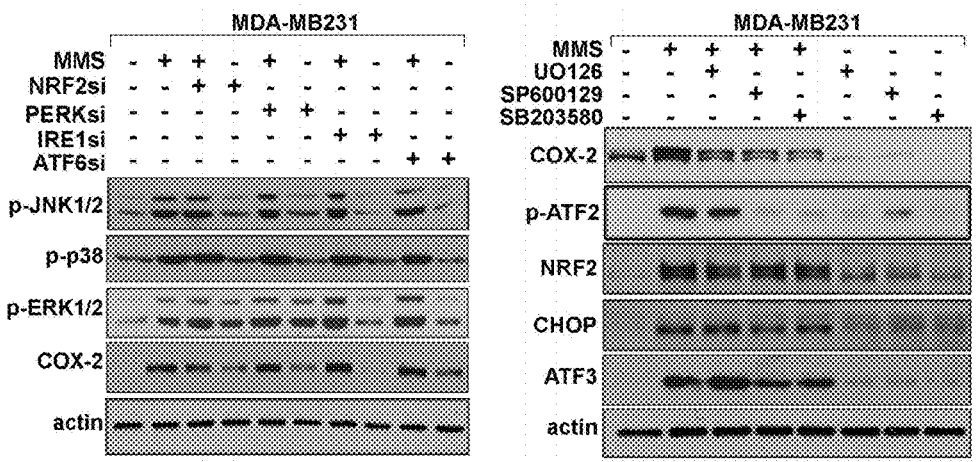
Figure 6G:
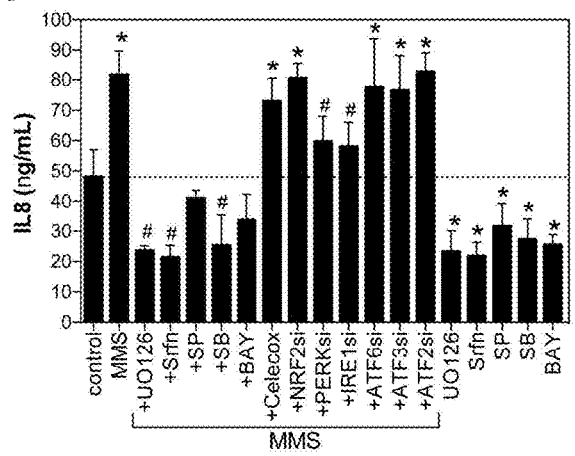
Figure 6H:
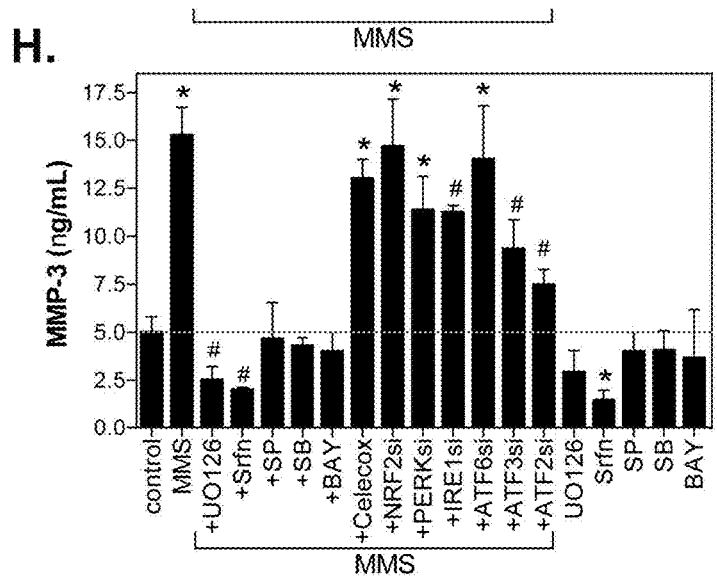
Figure 6I:
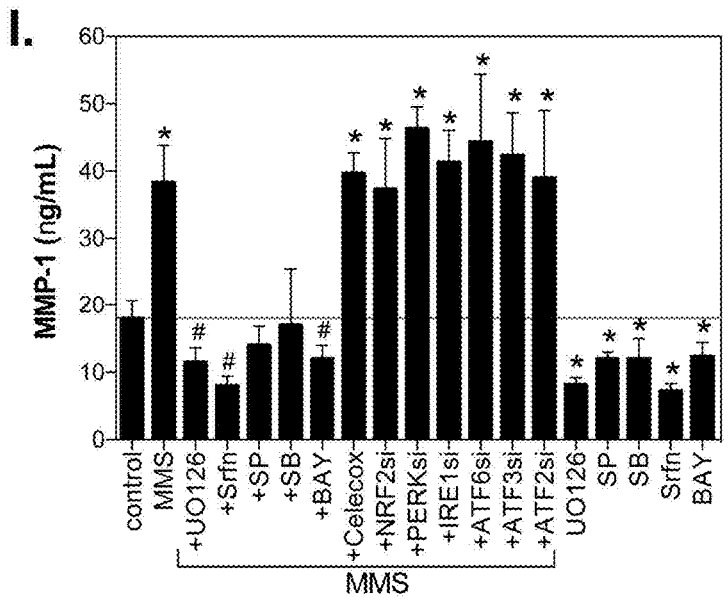
Figure 6J:
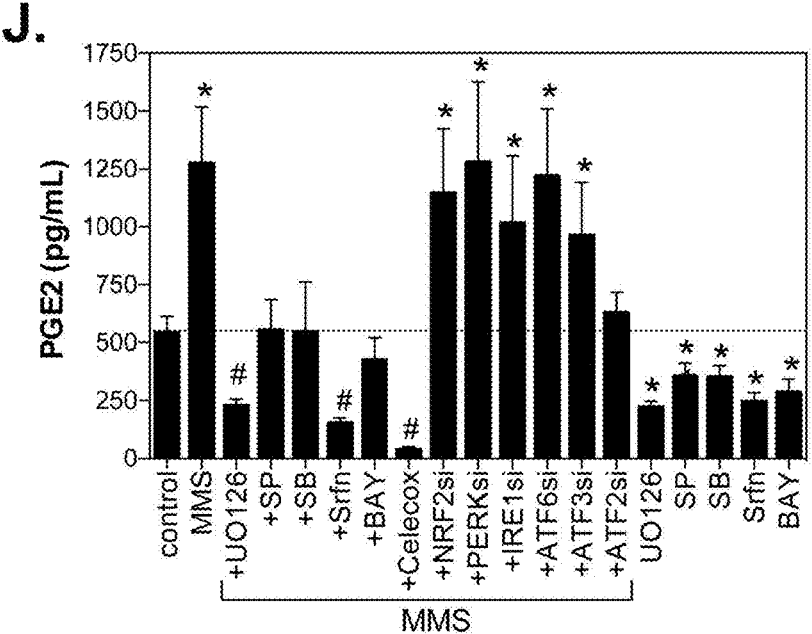

MMS increased phosphorylation of the three MAPK in MDA-MB231 and MEF (FIG. 6E). This response was inhibited by NAC pretreatment, again demonstrating the overarching protective role of GSH-mediated detoxification. However, phosphorylation of MAPKs by MMS did not alter by knockdown of ER stress sensors or NRF2 (FIG. 6F). Vice versa, MAPK inhibitors had no effect on MMS-induced NRF2, CHOP or ATF3, whereas the AP-1 member ATF2 phosphorylation was blocked by p38 and JNK1/2 inhibitors. Thus, the activation of MAPKs activation is not under the control of UPR/ER stress or NRF2 and, vice versa, these survival pathways do not rely on MAPKs, at least at the level of regulation that is being studied.

Next the bioinformatics prediction that the MAPK, NFκB and AP-1/ATF2 signaling pathways were driving alkylation-induced inflammatory signals was confirmed. Both MAPK (JNK1/2, ERK1/2 and p38) and NFκB inhibitors strongly inhibited MMS-induced secretion of IL8, MMP1, MMP3 and PGE2 into the culture medium (FIG. 6G to 6J) and COX-2 protein in cell lysates (FIG. 6F). Further, ATF2 siRNA inhibited MMS-induced prostaglandins and MMP3 secretion. These results confirmed that MAPK/NFκB and MAPK/AP-1 pathways are a component of the upstream regulation of these inflammatory mediators. Interestingly, not only did the MAPKs and NFκB inhibitors decrease alkylation-induced expression of these genes, but they also decreased the basal levels of IL8, PGE2 and MMPs (FIG. 6G to 6J), and in the result there was a concomitant decrease in the invasiveness of MDA-MB231 cells (FIG. 6A). ER stress mediators seem to exert some role in MMS-induced inflammation as observed from the inhibitory effect of PERK and IRE1a siRNAs on secreted IL8 and MMP-3 protein levels, without affecting MMP-1 and PGE2 levels (FIG. 6G to 6J). Further, the MAPK dependent program seems to play a minor role on MMS-induced cytotoxicity, since treating MDA-MB231, MEF and other breast cancer cell lines with MAPK, COX-2 and NFκB inhibitors—or purified prostaglandins—caused neither potentiation of MMS toxicity nor basal effects on viability at the concentrations (5 to 20 μM) and times tested (12 to 24 h), suggesting that these pathways do not play major roles in survival but propitiate invasion and pro-angiogenic phenotypes. Only a small, though significant, 30% decrease in cell numbers due to anti-proliferative (not cytotoxic) effect of the ERK1/2 inhibitor UO126 was observed following 72 h treatment since ERK1/2 is constitutively activate in MDA-MB231 due to constitutive RAS/RAF activation (Hoeflich et al., 2009, *Clin Cancer Res* 15, 4649-64). It is also important to note that quantifications in CM experiments were performed after 8 to 12 h treatments, when cell numbers and viability were similar among treatments.

Inhibition of the Inflammatory Pathway Affects Tumor Malignance Parameters In Vivo.

Figure 7A:
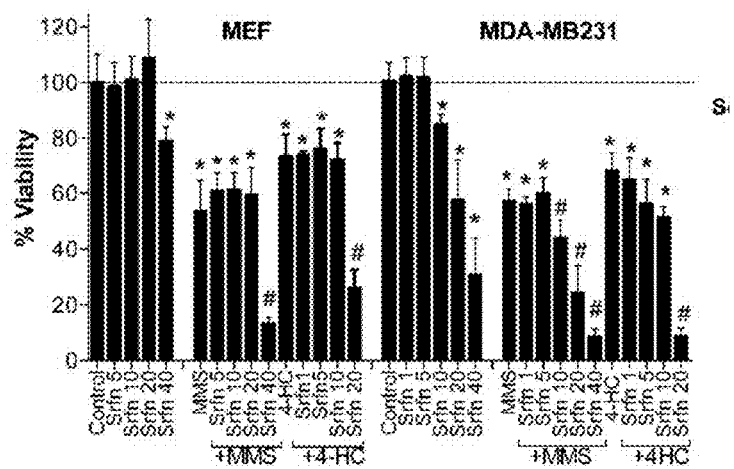
FIG. 7. Targeting the inflammatory pathway with sorafenib selectively blocks MAPKs-induced invasion and angiogenesis signals in cancer cells. (A) Low concentrations of the multi-kinase inhibitor sorafenib did not affect MMS/4-HC-induced losses in cell viability whereas higher levels caused non-selective detriment to both cancer cells and MEFs. (B) Sorafenib blocks inflammatory gene subsets without affecting NRF2 and UPR-dependent gene-expression responses in MDA-MB231 cells. Results from RNA sequencing in MMS-treated MDA-MB231 cells in the presence or absence of 5 µM sorafenib are represented as fold-induction compared to untreated. (C) Western blots showing the effect of sorafenib on MAPKs, NRF2 and UPR/ER stress pathway markers. Cell lysates were prepared after 8 h treatment. (D) Boyden Chamber experiments showing the effect of conditioned media from sorafenib alone or alkylator-treated plus sorafenib on trans-well cell invasion. (E-F) CD31 quantification (ELISA) and representative microphotographs showing the effect of sorafenib (plus/minus VEGFA in free drug systems) or/and conditioned medium from alkylator-treated (plus/minus sorafenib) on new vessel formation in vitro. Data are represented as mean±SEM. *different its respective control; #different from untreated and from MMS/alkylating agent treated cells (n=3; p<0.05, ANOVA).
Figure 7B:
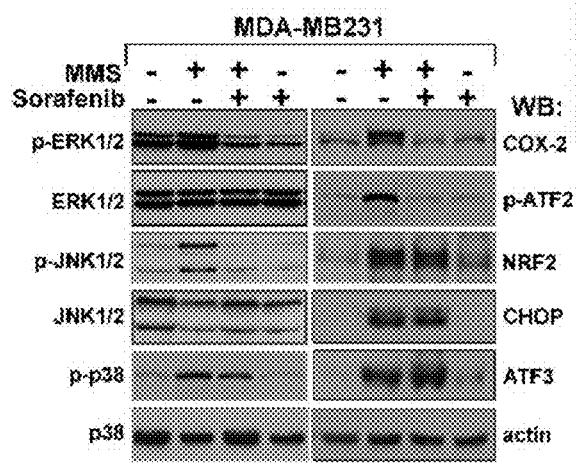

Considering that the inflammatory response induced by alkylation is not necessary for survival, its modulation is unlikely to result in general toxicity but may provide some benefit to cancer treatment due to the invasive and angiogenic component it modulated in vitro. Among the compounds tested, the multikinase inhibitor sorafenib exerted the strongest effect in blocking alkylation-induced IL8, COX-2/PGE2, MMP1 and 3, and it is proven to be clinically safe. Sorafenib blocked both MMS-induced phosphorylation of ERK1/2 and JNK1/2 as well as basal ERK1/2 in MDA-MB231 cells (FIG. 7B). Consequently, sorafenib blocked NFκB and AP-1 promoter activation, which are downstream ERK1/2 and JNK1/2 (FIG. 6C). Importantly, at the doses used for these experiments (1 to 5 μM), sorafenib did not affect viability of primary MEFs or breast cancer cells in the presence or absence of alkylating agents (FIG. 6A). However, at higher concentrations (from 20 μM) a non-selective cytotoxicity to both breast cell lines and MEFs was observed—characterized GSH depletion, aberrant ROS production (data not shown)—suggesting that there are additional off-target effects that impact its toxicity at high levels (FIG. 7A).

Gene expression profiling (RNAseq) in 5 μM sorafenib-treated MDA-MB231 cells in the presence/absence of MMS was used to validate the effects of low dose sorafenib.

Figure 7C:
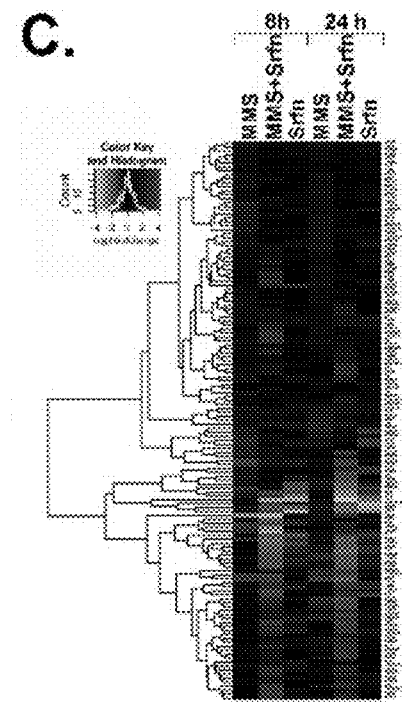
Figure 7D:
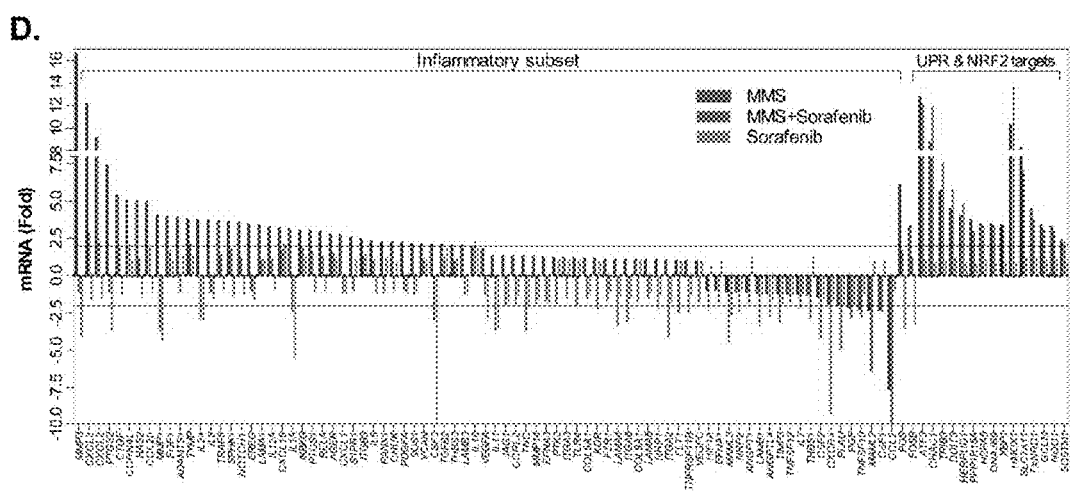
Figure 7E:
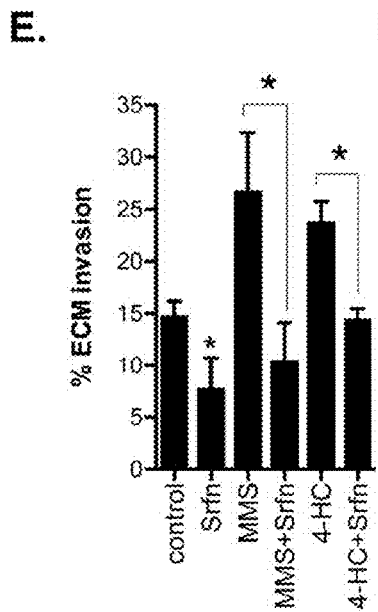
Figure 7F:
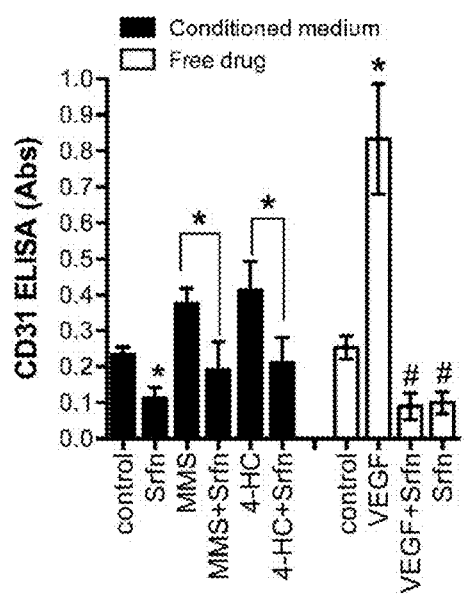
Figure 7G:
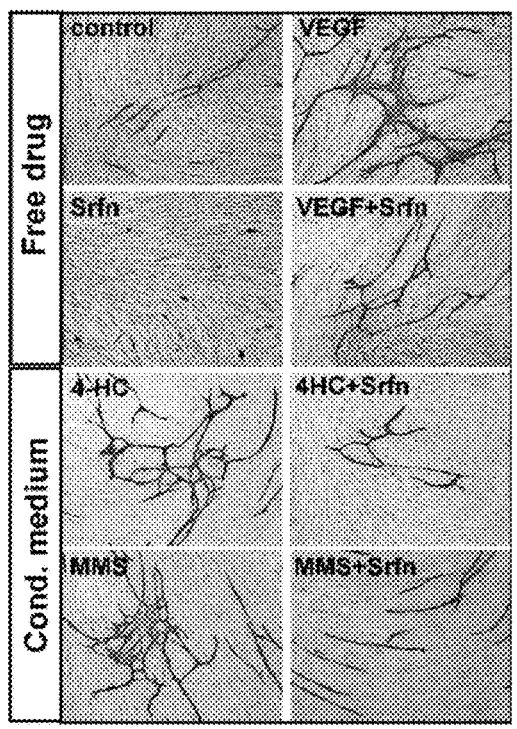

In fact, sorafenib blocked several of the aforementioned MMS-induced inflammatory/invasive genes, namely IL8, MMP1, MMP3, MMP10, PTGS2, EREG, HAS2, IL1B, CXCL2, CXCL3 and ADAMTS6. Sorafenib also decreased basal expression of several genes that have been implicated in the progression of breast cancer, such as VEGFA, NOTCH targets (HES1 and MAML3), PLAT, ADAMST1 and many others associated with extracellular compartment signaling (FIG. 7C). Pathway Enrichment Analysis of the gene expressions inhibited by sorafenib pointed out terms associated with several inflammatory processes, NFκB, Jun/AP-1 and MAPK signaling, while a lack of effect of sorafenib on NRF2 and UPR genes, confirming the selectivity of functional independence of MAPKs regarding to NRF2 and UPR (FIGS. 6E and 6F). When treating MDA-MB231 cells with CM obtained from sorafenib or sorafenib plus MMS/4-treated cells, these cells were unable to invade Boyden Chambers compared to CM from MMS or 4-HC alone (FIG. 7D). The same phenomenon was also observed on the inhibition of angiogenesis by CM from sorafenib treatments (FIG. 7E-F).

Figure 8A:
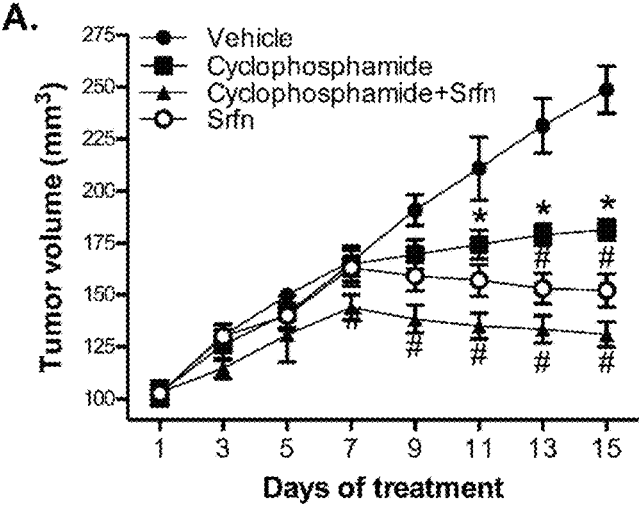
FIG. 8. (A) Effect of sorafenib and/or cyclophosphamide treatments on kinetics of MDA-MB231 cells growth in xenografts. (B) Representative microphotographs (200×; bar: 10 µm) showing the effect of sorafenib treatment on tumor vessels formation (CD31 staining), collagen and keratin deposition (Massom's staining) in the presence or absence of cyclophosphamide co-therapy. (C) Histopathological analysis of MDA-MB231 implants treated with cyclophosphamide plus/minus sorafenib. *different from untreated; #different from untreated and from cyclophosphamide alone treatments (p<0.05, ANOVA).
Figures 8B, 8C:
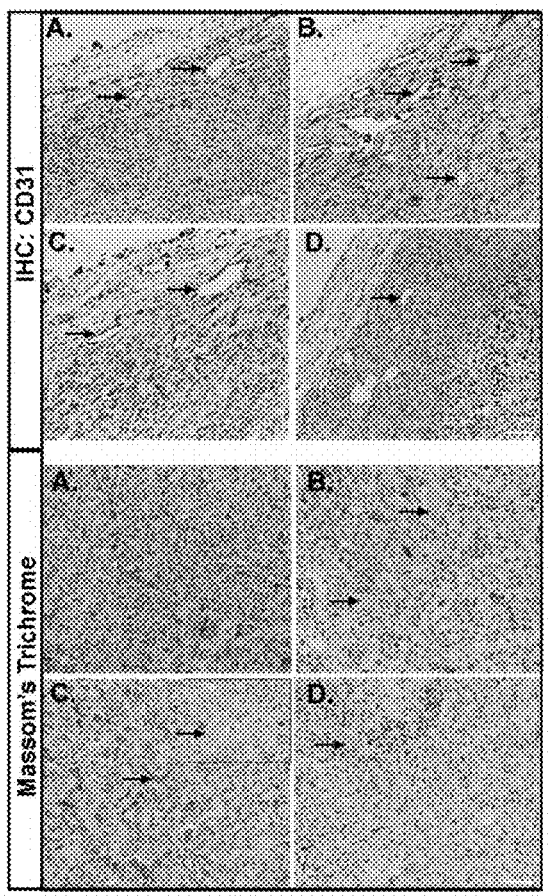
Figure 9A:
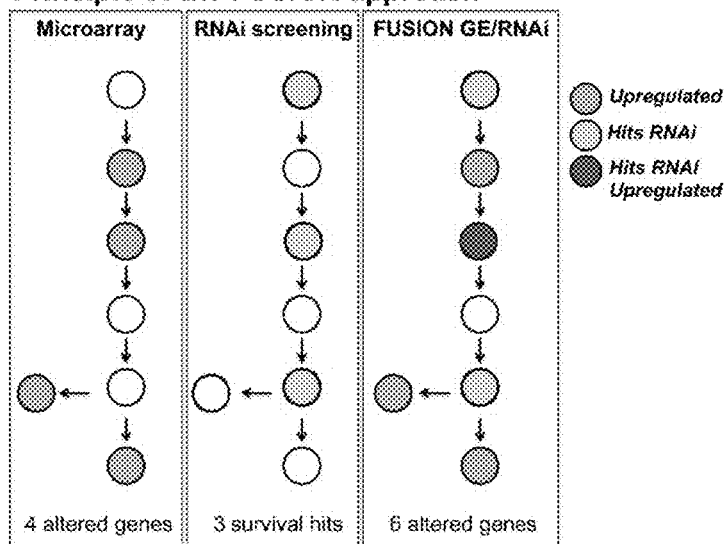
FIG. 9. Experimental design used in this study. (A) Different cell types (MDA-MB231, MEF and Kc167) were treated with MMS for 8 and 24 h. MMS-induced and down-regulated genes (fold>2 and <2, respectively) were separated and analyzed at gene level overlap, followed by Pathway Enrichment Analysis. Some of the most relevant MMS-induced pathways were validated using protein and cell functional assays. (B) Absolute numbers and percentage of MMS-induced/repressed gene expression (8 and 24 h treatment) alterations across fly, mouse (microarray) and human MDA-MB231 cells (RNA sequencing) platforms. Specie-specific gene numbers are shown.
Figure 9B:
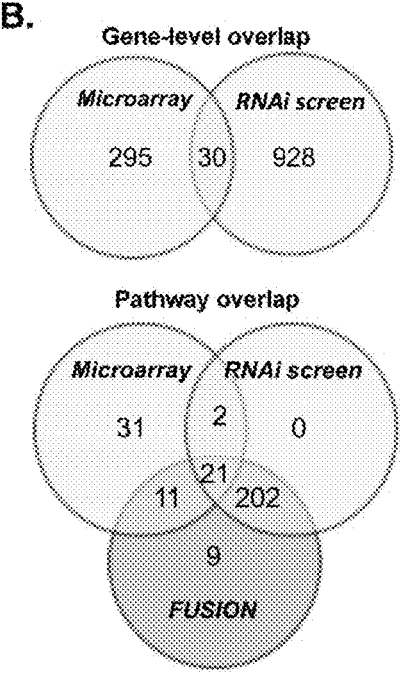
Figure 10A:
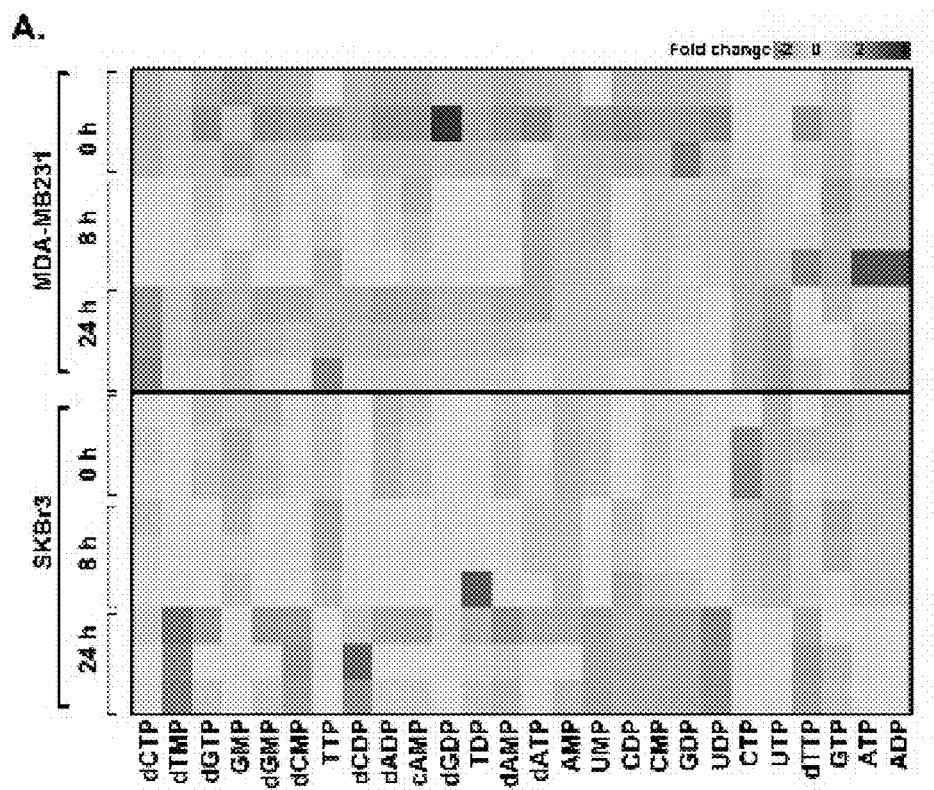
FIG. 10. Fusion of DEG in microarray and RNAi screening hits in fly cells under MMS exposure. (A) Overlap between MMS-induced genes and RNAi screening hits in fly using Venn Diagrams; list of genes that overlapped across microarray and RNAi platforms. (B) Schematic representation of the benefit of the FUSION approach. Genes that are induced do not necessarily overlap with genes whose knockdown causes lethality. The Fusion of hits from RNAi screenings and genes differentially expressed in microarrays could provide a better coverage by gathering altered and lethal genes within a given pathway. (C) Representative Pathway Enrichment Analysis (DAVID) of MMS-induced genes and hits from RNAi screening in fly Kc167 cells in i) microarray lists; ii) RNAi screening hits; iii) FUSION (microarray+ RNAi gene lists). Top panel: genes were converted and input as human orthologues; Bottom panel: fly genes symbols were used as input. The FUSION facilitated the detection of pathways not otherwise detected by microarrays lists, genes not regulated at the transcriptional level but lethal, as well as improved the p-values compared to RNAi and microarray independently.
Figure 10B:
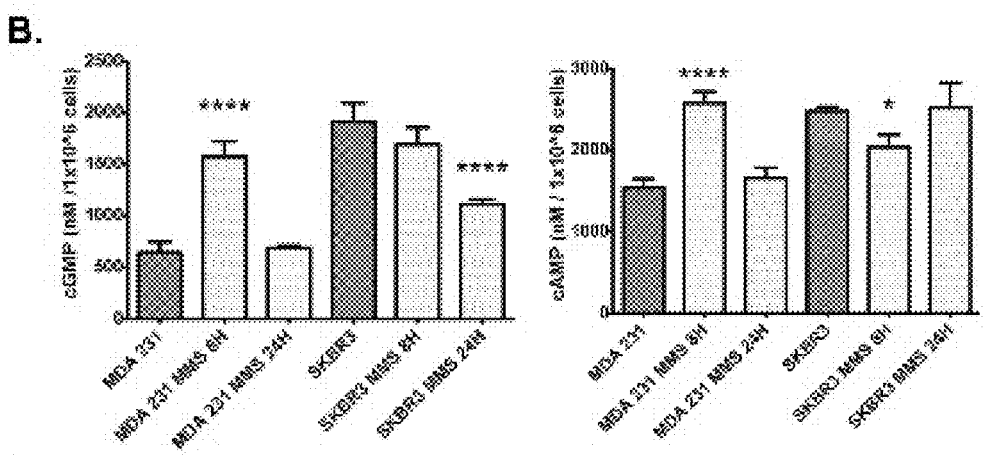
Figure 10C:
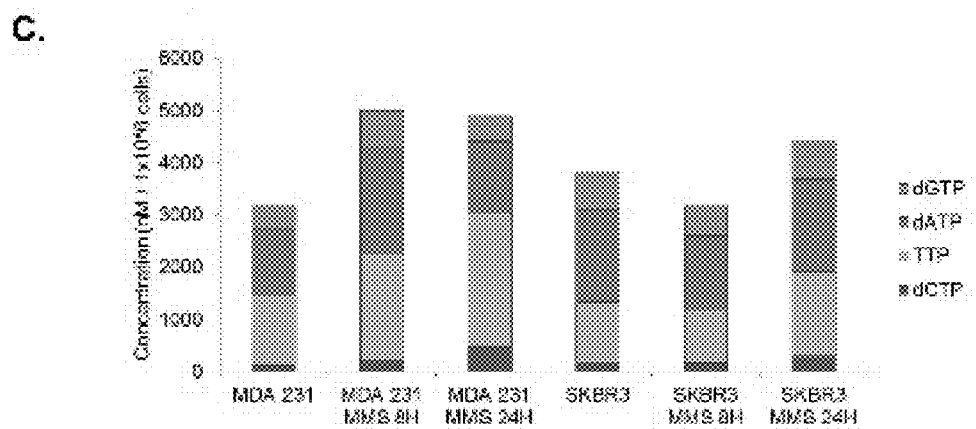
Figure 11A:
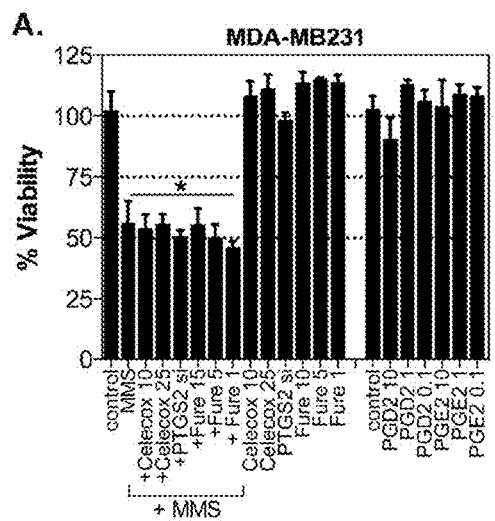
FIG. 11. MMS induces changes in nucleotide pools (Functional validation of Pathway Analysis). Nucleotide pool distribution of MDA-MB231 and SKBR3 cells without treatment, and treated with MMS for 8 and 24 h. (A) Basal distribution of nucleotide pool MDA-MB231 and SKBR3 differ between them, and drastic changes in the distribution of nucleotide pool are detected at 8 hours of treatment. (B) Changes in secondary messenger nucleotide cGMP and cAMP mainly on MDA-MB231 cells at 8 hours and moderate changes are detected on SKBR3 at 24 hours. (C) In general levels of DNA synthesis building blocks did not change with respect of total amounts of nucleotide pools. No statistical change was found after treatment on the content of deoxyribononucleotides. Concentration was logarithmic transformed and three independent replicates are presented as heatmaps. Different from its respective controls at: *$p<0.05$; *** $p<0.001$.
Figure 11B:
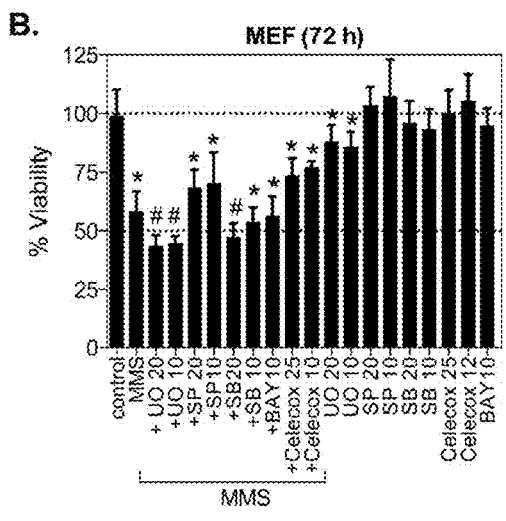
Figure 12:
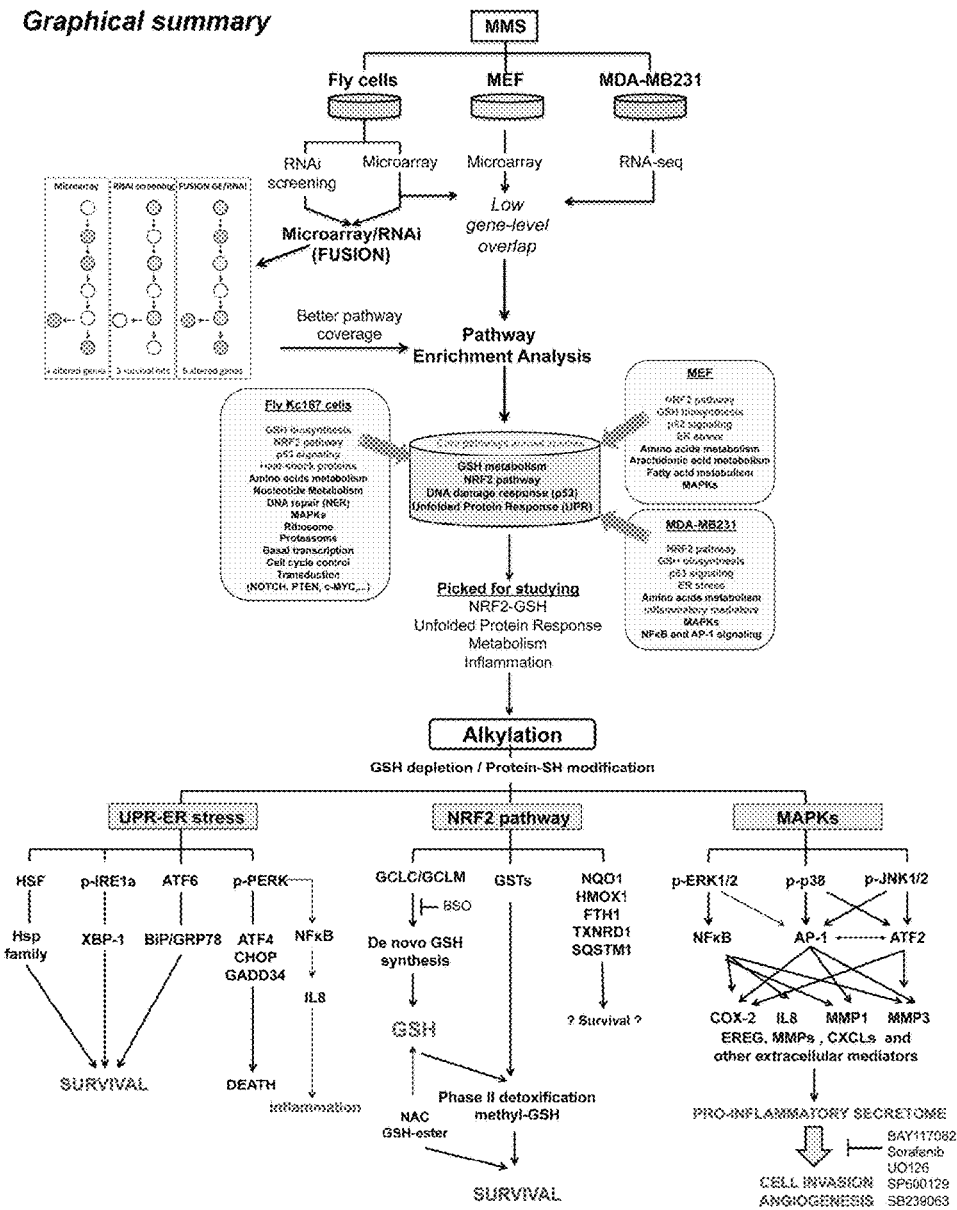
FIG. 12. Representative chart shows the Fusion of gene expression and RNAi screening data for up-regulated and lethal components with the NRF2-GSH and ER stress/UPR pathways in Kc167 cells treated with MMS. Genes with altered expression, hits and metabolites are differentially represented.

Last, MDA-MB231 xenograft implants were used to evaluate the impact of targeting the inflammatory/invasive phenotype of MDA-MB231 cells in vivo. In this study, tumors were allowed to grow up to 100 mm$^3$, and then animals were treated with cyclophosphamide, an alkylating agent used clinically to treat breast cancers, in the presence or absence of sorafenib (FIG. 8). Treatment with sorafenib alone was able to significantly decrease tumor growth compared to untreated tumors, and it was also able to synergize with cyclophosphamide (FIG. 8A). Tumor growth kinetics showed that sorafenib itself did not affect tumor growth with up to 7-days of treatment (~150 mm$^3$), but further tumor growth was stabilized up to the end of the experiment. Interestingly, the histological analysis of cyclophosphamide-treated tumors showed an increased number of niches of microvessels compared to untreated. Besides the angiogenic effect, cyclophosphamide promoted a wound healing phenotype characterized by spreading areas of collagen deposition along the tumor tissues (FIG. 8B, arrows). When combined with sorafenib, there was a significant inhibition of cyclophosphamide-induced angiogenic response, and tumors were well encapsulate with pushing borders (FIG. 8C). In addition, a marked tumor fibrosis and deposition of both collagen and keratin. These observations, taken together with the decreased tumor sizes, indicate that sorafenib promoted a more controlled tumor shrinking by blocking inflammatory/angiogenic responses caused by the alkylation, yielding "healed tumors".

Parallel to the development of targeted therapies to act as single agents, there is a growing effort to use these chemicals to potentiate the efficacy of classical chemotherapeutics by either re-sensitizing a chemoresistant cancer or improving the therapeutic window of the chemotherapy. Targeted therapies promise specific cancer cell targeting and reduced toxicity to normal tissues. However, realization of this promise has been impeded by low efficacy, side-effects and resistance in clinical trials. Understanding normal versus cancer cell responses and that using comparative biology strategies may help parse out which targets are more or less likely to succumb to the desired chemotherapeutic potentiation without the adverse effects to normal tissues.

Herein, the knowledge provided by mouse, fly and human cross species comparisons was used to understand the basic common and differential responses to propose a strategy to treat cancers in an alkylation damage context. The first conclusion was that comparison of alkylation-induced responses at a gene-by-gene level seems to be a fruitless strategy, especially across species, irrespective of their evolutionary distance; low levels of overlap were observed even when comparing mammalian cells. The misleading differences in gene profiles were solved using system biology, by examining pathways instead of restricting analysis only to top-regulated genes. This demonstrated that different cells, even from different species, share similar pathways/processes to respond to alkylation damage, though modulating different gene sets to achieve this effect. Further, the fusion of RNAi screening data and gene expression profiles in fly cells demonstrated that the regulation of pathway activity by the dynamic expression of a gene does not indicate that these same genes are essential to that process. Alternatively, by the nature of their dynamic gene expression, these genes may be more refractory to RNAi knockdown. Conversely, the proteins that are sensitive to RNAi knockdown and modulate the activity of a pathway may not be dynamically expressed genes. This is exemplified by Hsf and cnc—two master regulators of the UPR and NRF2-GSH responses known to be mostly regulated at the posttranslational level (Jaramillo, Zhang, 2013, *Genes Dev* 27, 2179-91; Li et al., 2012, *PLoS One* 7, e35122; Wu, 1995, *Annu Rev Cell Dev Biol* 11, 441-69)—whose knockdown caused lethality, but expressions were not altered by MMS. Thus, fusing gene expression changes with RNAi screening hits provides an interesting strategy for pathway identification.

These results demonstrate that NRF2 is pivotal to control alkylation toxicity due to maintenance of GSH pools. Electrophilic compounds, such as alkylating agents, may react with cysteine groups in KEAP1, thus blocking KEAP1-mediated NRF2 degradation. NRF2 can then translocate to the nucleus and regulate expression of genes such as GCLC, CAT, GSTs, HMOX1, UGTs and NQO1, which are important for antioxidant activity and phase II xenobiotic detoxification (Li et al., 2012, *PLoS One* 7, e35122; Wu, 1995, *Annu Rev Cell Dev Biol* 11, 441-69). In the context of alkylation, NRF2 activation was required to induce GSH production through transcriptional regulation of GCLC to counteract the depletion of GSH used to form methylglutathione during MMS detoxification. Not only does NRF2 instigate a cellular reprograming to induce the key enzymes for de novo GSH synthesis (GCLC, GCLM, GSS) and the pentose phosphate pathway genes (UGTs, TALDO1), which are necessary to provide both precursors of GSH synthesis and NADPH for GSH recycling from GSSG by GSH reductases (Mitsuishi et al., 2012, *Cancer Cell* 22, 66-79). Some studies have suggested the use of GSH depletion, for example by BSO, to potentiate 4-HC, TMZ, melphalan, cisplatin and doxorubicin toxicity to different cancer cells, while conversely up-regulation of NRF2 or GSH system could confer chemoresistance (Lee et al., 2008, *Mol Cell Biochem* 318, 23-31; Fujimori et al., 2004, *Int J Oncol* 25, 413-8; Anderson et al., 1997, *Eur J Cancer* 33, 2016-9; Sugimoto et al., 1996, *Anticancer Res* 16, 675-80; Friedman et al., 1992, *Cancer Res* 52, 5373-8). Here NRF2 and GSH were connected in the context of alkylating drugs response, and also showed that this is a well-conserved process across normal and cancer cells types, and from evolutionary distant organisms. Based on these findings, GSH depletion could potentiate alkylation toxicity in tumor cells while also increasing damage to healthy cells. On the other hand, GSH precursors as NAC have been used to block nephrotoxicity cause by alkylators (Abdelrahman et al., 2010, *J Appl Toxicol* 30, 15-21; Chen et al., 2008, *Br J Pharmacol* 153, 1364-72), though data presented here would predict NAC also to cause a non-desired protection of cancer cells. However, NAC has been shown to ameliorate ifosfamide nephrotoxicity in children without reducing antitumor efficacy due to its preferential accumulation in urinary tract (Chen et al., 2007, *Can J Clin Pharmacol* 14, e246-50). NAC also protected bladder and renal cells from cyclo/ifosfamide toxicity (Chen et al., 2008, *Br J Pharmacol* 153, 1364-72; Chen et al., 2007, *Can J Clin Pharmacol* 14, e246-50; Hanly et al., 2012, *Anticancer Res* 32, 3791-8; Wu et al., 2005, *J Pharmacol Exp Ther* 312, 424-31), presumably due to a similar bioavailability advantage. Although the protective effects of NAC are frequently attributed to an antioxidant potential, data presented here suggest that NAC, and GSH-ester, protected cells by increasing the GSH pool necessary for alkylating agent detoxification. In fact results point out that ROS are not a major component of alkylation-induced cytotoxicity, but are likely a secondary phenotype resulting possibly from GSH pool depletion. It should also be noted that GSH can facilitate chemoresistance by serving as a cofactor for multidrug resistance protein-2 mediated drug efflux (Chen, Kuo, 2010 *Met Based Drugs*) or as a target of GSTs to detoxify reactive agents such as alkylators (Goto et al., 1999, *Free Radic Res* 31, 549-58). The conservation of NRF2-GSH responses raise concerns about the growing interest of using NRF2 inhibitors in combination therapies in cancer due to a possible toxicity to normal tissues (Wang et al., 2008, *Carcinogenesis* 29, 1235-43).

Given such commonality of the NRF2-GSH and UPR/ER stress in mitigating alkylation cytotoxicity across evolutionary distant species, it was presumed that modulating this response would have a non-selective deleterious effect on both cancerous and normal tissues. Therefore a differential mechanism was looked for, and alkylators activated inflammatory pathways leading to production of cytokines, MMPs and prostaglandins, which did not affect cell survival to alkylation, but did affect invasiveness and angiogenesis, two phenotypes associated with aggressive cancers were indentified. In fact, this response to alkylating agents, and potentially other DNA damaging chemotherapies, would be detrimental for cancer treatment, but global systems analysis offered the opportunity to identify the mechanisms driving this response and hopefully an intervention to limit the effect. In the model discussed here, alkylation-induced inflammatory genes were under control of the MAPK signaling. MAPK pathway activated NFκB (via ERK1/2 and p38) and AP-1 (via JNK and ERK) transcription factors, two well-known regulators of inflammation and cancer progression and potential for targets for drug development (Ling, Kumar, 2012, *Cancer Lett* 322, 119-26; Baud, Karin, 2009, *Nat Rev Drug Discov* 8, 33-40). Although results show that MMS-induced NRF2 and MAPK-driven inflammation pathways seem to be independent at the level of regulation studied, ER stress, mainly PERK, seems to contribute to NFκB activation and IL8 and MMP3 induction by MMS. In fact, there is growing evidence that UPR/ER stress sensors could modulate NFκB activity and inflammation. For example, PERK-mediated attenuation of translation resulted in release of NFκB from IκB to increase IL1 and TNF-alpha (Hotamisligil, 2010, *Cell* 140, 900-17). In addition, XBP1s and ATF4 activation can induce production of IL-8, IL-6 and CCL2 by human endothelial cells (Hotamisligil, 2010, *Cell* 140, 900-17). Thus, there are many levels whereby UPR may contribute to inflammation, but it seems to play a minor role compared to MAPKs.

A number of studies have substantiated the up-regulation of the herein identified inflammatory mediators with aggressive phenotypes in cancer and, worse, results show that alkylating chemotherapies are capable of enhancing inflammation even more. Evidence of chemotherapy promoting malignance is reinforced from studies that showed that doxorubicin promoted metastasis of breast cancer in mice through TGF-beta activation (Bandyopadhyay et al., 2010, *PLoS One* 5, e10365). In support of this novel concept, it has been shown that combining the COX-2 specific inhibitor celecoxib with TMZ improved the therapy efficacy in preclinical gliomas by blocking angiogenesis (Kang et al., 2006, *Oncol Rep* 15, 7-13). In addition, TMZ also induced IL8 and CCL2 production in HCT116/3-6 and M10 cells through NFκB activation (Caporali et al., 2012, *J Transl Med* 10, 252). Not restricted to alkylating agents, paclitaxel and docetaxel increased COX-2 expression in RAW264.7 macrophages and peripheral blood mononuclear cells (Cassidy et al., 2002, *Clin Cancer Res* 8, 846-55). Taken together, these data support the premise that induction of inflammatory responses might be a general side-effect to be tested with different DNA damaging drugs. Of key relevance, most of the MMS/alkylation-induced inflammatory genes correlate with aggressive phenotypes in cancers. For instance, MMP-1 is highly correlated with poor prognosis and worse (Bostrom et al., 2011, *BMC Cancer* 11, 348). Overall Survival in breast cancer, and its over-expression promotes brain metastasis of breast cell lines (Cheng et al., 2008, *J Surg Res* 146, 104-9; Liu et al., 2012, *BMC Cancer* 12, 583). With the prostaglandin pathway, overexpression of COX-2 in the mammary glands of mice increased levels of PGE2, leading to tumorigenesis and angiogenesis; and blocking of PGE2 production with indomethacin or celecoxib rescued tumors to lower grades of malignance (Chang et al., 2004, *Proc Natl Acad Sci USA* 101, 591-6). An ERK1/2-COX-2 signature was found in aggressive basal breast cancer cell lines (Heiser et al., 2012, *Proc Natl Acad Sci USA* 109, 2724-9). COX-2 derived PGE2 also promoted invasiveness of MDA-MB231 cells through EP4-EGFR-ERK1/2 activation (Subbaramaiah et al., 2008, *J Biol Chem* 283, 33955-68). Regarding IL8, which is barely detectable in healthy tissues, it has optimal gene induction generated from transcriptional activation by NFκB and JNK/c-Jun (AP-1), and stabilization of the mRNA by p38, agreeing with herein determined mechanism of alkylation-induced IL8 via MAPK-NFκB signaling (Hoffmann et al., 2002, *J Leukoc Biol* 72, 847-55). Although most of the studies focused on investigating an inflammatory factor at once, it has been reported that COX-2, MMP1, EREG and CXCL1 cooperate to promote breast cancer metastasis to the lung (Minn et al., 2005, *Nature* 436, 518-24).

Tumors are known to suppress wound healing in order to favor progression (Gatenby, Taylor, 1990, *Cancer Res* 50, 7997-8001). In vivo, using a MDA-231 xenograft model, it was noted that cyclophosphamide not only reduced tumor size, but also induced an unexpected angiogenic rebound and deposition of collagen; typical hallmarks of wound healing phenotypes. As predicted by in vitro studies, sorafenib blocked cyclophosphamide-induced vessels formation yielding well-encapsulated, shrunken and healed tumors, which displayed extensive collagen deposition and keratinization. This demonstrates that by inhibiting the inflammatory response to the chemotherapy improved tumor-killing efficacy by causing a more controlled tumor arrest/healing can be obtained. Thus, the alkylation-mediated induction of inflammatory genes emulates the process of other inflammatory/wound healing processes; a repertoire of cytokines, prostaglandins, MMPs and other extracellular signaling factors cooperate to modulate angiogenesis, infiltration and reprograming of immune cells. Alkylation-induced inflammatory signals appear to be induced in both cancer and normal damaged cells (herein showed in MDA-MB231 and MEFs). This inflammatory activity is also likely to recruit the immune system and may facilitate their reprogramming and tumor escape (Kerkar, Restifo, 2012, *Cancer Res* 72, 3125-30). Compounding the potential impact of this phenomenon is that the damage-induced inflammation (e.g. PGE2 and IL6) promoted an immunotolerant microenvironment by inducing differentiation of monocytes into M2 macrophages (Heusinkveld et al., 2011, *J Immunol* 187, 1157-65); an effect that is blocked by sorafenib thus maintaining the immunosuppression of the tumor. Since this phenomenon is unlikely to be limited to alkylating agents, there may be a need to evaluate this response with a range of cytotoxic chemotherapeutics and determine whether there are differences in the inflammatory response profile (e.g. different genes activated by different antitumoral drugs), how different cancer cells respond and whether the MAPK pathway is instrumental in controlling this response.

In summary, it is demonstrated here that it is possible to not only fuse RNAi screen and gene expression data within species, but also to compare across species, by using biological pathways. This was because the genes that were dynamically regulated in response to a stimulus within a pathway were not necessarily the same as the proteins that were essential for that pathway's function and sensitivity to RNAi knockdown. In fact, this strategy could be useful for many other studies that use this kind of technology. Secondly, GSH is pivotal for alkylation detoxification, and its production is controlled by the conserved xenobiotic detoxification pathway, NRF2. In addition, the ability of a cell to respond by inducing changes in NRF2/GSH levels during alkylation insult plays a role in the control of UPR/ER stress durationand magnitude, which is also important for survival across species. Finally, a non-conserved alkylation-induced MAPK-dependent inflammatory signaling that mediates a pro-invasive, angiogenic response in a tumor was detected, this could be pharmacologically targeted in vitro and in vivo toward the goal of achieving a more controlled tumor killing and healing. Together these results indicate that the cellular response to cytotoxic chemotherapy is multifaceted and not restricted to classical DDR pathways, and by elucidating these responses new avenues to improve chemotherapeutic cancer treatment can be revealed.

Methods

Cell Culture and Treatments.

The *D. melanogaster* embryonic cell line Kc167 was grown in Schneider medium (Invitrogen, Carlsbad, Calif.) supplemented with 10% heat-inactivated (56° C./30 min) fetal bovine serum (FBS), penicillin and streptomycin at 22° C. in a humidified incubator. Primary MEFs were obtained by harvesting 14.5-day C57BL/6J embryos as previously described (Ravi et al., 2009, *PLoS Genet* 5, e1000527). Briefly, fetal liver and head were removed and the remainder of the embryo was mechanically disaggregated in plating medium. A suspension of single-cells was plated in DMEM (plus 10% FBS, 100 U/mL penicillin and 100 μg/mL streptomycin). MEFs were grown for two passages before freezing aliquots. Aliquots were taken and expanded as needed for each experiment. MDA-MB231, SkBr3 and MCF-7 breast cancer cells lines were obtained from ATCC and grown in DMEM supplemented with 10% inactivated FBS plus antibiotics in a 37° C. humidified incubator at 5% $O_2$ and 95% $CO_2$ atmosphere. Cells were kept and treated in the exponential phase of growing (60-70% confluence). Pharmaceuticals Sorafenib (Santa Cruz Biotechnology), UO126, SP600125, SB239063, celecoxib, buthionine sulfoximine (BSO), cycloheximide (CHX), actinomycin D and BAY117082 (BAY), or antioxidants as N-Acetyl-Cysteine (NAC), glutathione ethyl-ester (GSH-E) and Trolox (all from Sigma-Aldrich, USA) were pre-incubated with cells for 6 to 8 h before treatments with MMS, temozolomide, CDDP (from Sigma-Aldrich, USA) or 4-hydroperoxycyclophosphamide (4-HC; from US Biological). DMSO concentrations were kept to a maximum of 0.1% for all experiments.

Gene Expression Profiling by Microarray and RNA-Seq Protocol.

For microarray, $7.5 \times 10^6$ Kc167 *Drosophila* cells or $5 \times 10^6$ wild-type MEFs were seeded in T-75 cell culture flask in complete growth medium one day before treatments. On the following day, the medium was replenished with fresh growth medium or medium consisting of MMS at 40 μg/mL. Cells were harvested and pelleted at different times post treatment (0, 1, 8, 24 and 72 h), washed using ice cold phosphate buffered saline (PBS) and the RNA was extracted using the RNeasy kit protocol (Qiagen). RNA integrity was assessed by denaturing formaldehyde agarose gel electrophoresis or by microanalysis (Agilent Bioanalyzer, Santa Clara, Calif.). Microarray service was provided by Expression Analysis Inc., Durham, N.C. Affymetrix GeneChip *Drosophila* Genome 2.0 Array was used for the experiment performed using Kc167 cells, and Affymetrix GeneChip Mouse Genome 430A 2.0 Array was used for experiment performed using MEFs. The microarray service provided by Expression Analysis Inc., included group comparison between experimental control and MMS treatment and time course analysis based on permutation analysis of differential expression (PADE). For statistical comparison, each experiment was performed in quadruplicate.

Human cancer cell-lines treated with different pharmaceutical compounds were profiled by RNA-seq protocol using Illumina HiSeq 2000 system (Illumina, San Diego, Calif.). RNA was harvested 0, 8 and 24 hours post treatment using the RNeasy protocol (Qiagen) and the purity of prepared RNA was determined using Agilent 2100 BioAnalyzer. Total RNA samples about 1-2 g were used for sequencing library preparation according to Illumina TruSeq Total RNA Sample Preparation Guide (Illumina Cat. #: RS-122-2201). Each library was bar-coded and then pooled for cluster generation and sequencing run with 100 bp paired-end (PE) sequencing protocol. Short read sequences from RNAseq were first aligned to UCSC hg19 genome build using TopHat2 algorithm (PMID:19289445) and then quantified for gene expression by HTSeq [Anders, 2014]. Genes with lower read counts (determined by examining read counts in non-exonic regions) were removed. Differential expression more than 2 fold was selected as differentially expressed genes (DEGs).

Pathway Enrichment Analyses.

For those genes for which expression was higher than noise/background, significant change in expression compared to unexposed (0 h) control, ±2-fold change, was used as cut-off for induction/repression. The lists of genes with altered expression were analyzed using Ingenuity Systems (IPA, Ingenuity Pathway Analyzer, Qiagen), DAVID (PMID:19131956; PMID: 19033363), and Rock Breast Cancer Functional Genomic Database (PMID:20563840) analytical software (p<0.05; FDR<10%) to ensure a good coverage of both metabolic and transduction pathways (due to differences in pathways libraries with the databases). Only pathways related to biological processes/signaling were considered relevant, and the terms were grouped by similarity of the biological for presentation; disease related pathways were discarded. Transcription factor enrichment analysis was performed using the TFactS software (PMID: 20215436), which uses an algorithm to compare potential transcription factors involved in the regulation of genes with the input lists. FDR<10% and p-value<0.05 were the setup parameters preferentially used.

Gene/Protein-Interaction Network and Landscape Analysis of Gene Expression.

Fly gene/protein interaction networks were constructed by associating genes belonging to the classical NRF2 and UPR-ER stress pathways identified in microarrays and RNAi screenings (FIGS. 2A and 3A). (i) NRF2-GSH pathway: components of the transcription factor core signaling, NRF2 transcriptional targets, genes involved in GSH synthesis and GSH-mediated detoxification; (ii) ER stress/UPR: chaperones and heat shock factors, ER sensors, and ER-to-Nucleus signaling transducers and input as fly orthologs. Briefly, the network is generated using STRING database with input options 'databases', 'experiments', 'textmining' and 0.700 confidence level. The selected gene list is applied in the STRING database and the links (interaction strength) between two different genes were handled in the Medusa software (Hooper, Bork, 2005, *Bioinformatics* 21(24), 4432-3). After being constructed, the networks were analyzed by the ViaComplex software, which was previously developed and validated (Castro et al., 2009, *Bioinformatics* 25(11), 1468-9). ViaComplex plots the gene expression activity over the Medusa network topology. In this intent, ViaComplex overlaps functional information (gene expression) with interaction information (Network connectivity) and distributes the microarray signal according to the coordinates of the network objects (i.e. nodes and links) thus constructing Z-axis/3D landscape modules. For each gene, means of each gene expression in MMS treated samples was plotted over the expression of the same gene in controls, and landscapes were constructed.

Metabolomics and Metabolic Pathway Enrichment Analysis.

The $2.4 \times 10^6$ Kc167 or $2 \times 10^6$ MEFs were seeded using complete growth medium on Day 0 in a T-175 cell culture flask and were allowed to grow for three days. After treatments with MMS (40 µg/mL), cells were harvested and centrifuged at 8 and 24 hours, and washed using ice-cold PBS. The cell numbers were adjusted to $90 \times 10^6$ (Kc167) or $24 \times 10^6$ (MEF) and provided as 100 µL of packed cell pellet for metabolic profiling. Metabolomic profiling and data analysis was provided through mView service performed by Metabolon Inc., Durham, N.C. Five biological replicates of each group were used for analysis at each time point. In addition, detailed changes in nucleotide pools were measured in a separate set of experiments. Nucleotide quantification and Metabolomics Pathway Enrichment Analyses were performed through MetaboAnalyst 2.0 (Xia et al., 2012, *Nucleic Acids Res* 40(Web Server issue), W127-33; Xia et al., 2009, *Nucleic Acids Res* 37(Web Server issue), W652-60).

Cell Viability and Caspase Activity.

Cell viability was assessed using CellTiter-Glo Luminescent Viability assay (Promega) in 384 or 96-well plates white-border clear-bottom plated cells. For caspase-3/7 activity, Caspase-Glo 3/7 Assay kits were used (Promega). For caspase assays, the cells were seeded in 96-well plates and assayed directly after treatments. Caspase-3/7 inhibitor (Z-DEVD-fmk) was used to ensure assay specificity. LDH release into culture medium was quantified by Cytotox-96 Non-Radioactive assay kit in agreement with instructions (Promega).

Real-Time ROS Production.

Intracellular ROS production was detected using DCFH-DA probe (Sigma) (Zanotto-Filho et al., 2010, *Cancer Lett* 288, 192-203). This reagent enters the cells and reacts predominantly with highly oxidizing species of ROS, such as hydroxyl radicals, hydroperoxides, and peroxynitrite, thus producing the fluorophore DCF. Briefly, cells were seeded in black-edge clear bottom 96-well plates. After reaching 70% confluence, medium was changed and cells were incubated with 20 µM DCFH-DA dissolved in medium containing 0.5% FBS. After 1 h pre-incubation to allow DCFH-DA uptake, treatments were added to its respective final concentrations and DCF fluorescence was monitored at 0.5, 1, 3, 8, 12, 16 and 24 h in a fluorescence reader (Ex/Em=485/532 nm). Hydrogen peroxide was used as a positive control and N-acetylcysteine (NAC), GSH-ethyl-ester (GSH-E) and Trolox were used as antioxidant standards. As a control, at the end of 24 h, cell viability was assessed and compared to wells in the absence of DCFH-DA.

siRNA Experiments.

Small-interference RNA (siRNA) protein knockdowns were performed through reverse transfection using the Lipofectamine RNAiMAX Reagent (Invitrogen) following manufacturer instructions. siRNAs duplexes against human NRF2 (sc-37030A, sc-37030B batches), ATF3 (sc-29757A and sc-29757B batches), IRE1a (sc-40705), GADD153/CHOP (sc-35437), PERK (sc-36213), COX-2 (sc-29279) and control siRNA-A were purchased from Santa Cruz Biotechnology. ATF6 (ID22926 trilencer-27) was from Origene. Cells were transfected from 10 to 50 nM siRNA for 12 h (NRF2, CHOP and ATF3) or 36 h (PERK, IRE, ATF6 and COX-2) depending on the constitutive level of each target to permit adequate knockdown, which was confirmed by western blot. Lipofectamine complexes were not removed during treatment as they did not affect cell viability.

Gene Reporter Assays.

Prior to transfection, cells were plated in 96-well plates to 80-90% confluence (100 µL antibiotic free-medium) after 24 h. When used, siRNA were incubated by reverse transfection during cells seeding. After 24 h, the cells were transfected in quadruplicate with a mixture of 40:1 (100/2.5 ng) of AP1 or NFκB-responsive firefly luciferase constructs (AP-1-luc and NFκB-luc, Stratagene) and constitutive CMV-*Renilla* luciferase construct (Qiagen) for 24 h. A mixture of non-inducible firefly luciferase construct and constitutively expressing *Renilla* luciferase construct (40:1) were used as negative controls. Approximately 24 h post-transfection, the medium was changed and the cells were treated for 12 h with alkylating agents (with/out 6 h pre-treatments). At the end of this period, medium was changed to drug-free fresh medium (to minimize the effect of alkylating toxicity on promoters activity) and cells were kept for an additional 12 h. Medium was discarded and cells were lysed in 150 µL passive lysis buffer (Promega), and 50 µL of the cell lysates were assayed to detect *Renilla* and Firefly luciferases using the Dual-Luciferase® Reporter Assay System according to the manufacturer's instructions (Promega) with a M5-microplate reader (luminescence, 1000 ms integration).

Western blot. Protein lysates were prepared using RIPA buffer containing 5% sodium deoxycholate, 0.1% SDS, 0.1% Igepal in PBS with a cocktail of protease and phosphatase inhibitors (1 mM PMSF, 1 mM sodium orthovanadate, 1 mM NaF, and 30 µL/mL aprotinin (Sigma-Aldrich, USA)) and clarified by centrifugation. Protein concentration was determined using Bradford Protein Assay Reagent (Biorad, Hercules, Calif.). Equal amounts of protein were resolved using 8-12% SDS polyacrylamide gel, transferred onto nitrocellulose membranes (Hybond-ECL, GE Healthcare Lifesciences, Piscataway, N.J.) and detected using Lumiglo system (Cell Signaling Technology, Calif.) and x-ray films. Primary antibodies included COX-2 (#4842), NRF2 (D1C9), p-JNK1/2 (Thr183/Tyr185, #4671), p-p38 (Thr180/Tyr182, #9216), p-ERK1/2 (Thr202/Tyr204, #9101), BiP/GRP78 (C50B12), IRE1a (14C10), CHOP (L63F7) and PERK (D11A8) from Cell Signaling Technology; p-IRE1a (Ser724; NB100-2323) from Novus Biologicals; GCLC (Ab41463), beta-actin (ab8227) and ATF6 (Ab37149) from Abcam; p-PERK (Thr 981, sc-32577) and ATF3 (C19) were purchased from Santa Cruz. All primary antibodies were used at 1:1000 dilutions and secondary antibodies were 1:3000 in TBS-T with 5% BSA.

Glutathione Assays.

Intracellular glutathione levels were measured using the Glutathione (GSH/GSSG/Total) Fluorometric Assay Kit (BioVision Incorporated, Calif.), following manufacturer protocol. Briefly, $1 \times 10^6$ cells were scraped in PBS and centrifuged. Pellets were resuspended in 100 µL Glutathione assay buffer. 60 µL of this homogenate was mixed with PCA (perchloric acid) and centrifuged. Supernatant containing small molecules including GSH were neutralized with KOH and 3 fractions were collected and separated to analyze reduced (GSH), oxidized (GSSG) and total glutathione forms (GSH+GSSG) by reaction with OPA probe (o-phthalaldehyde) in the presence or absence of GSH quencher or reducing agents depending on the compound to be determined. Fluorescence was monitored at Ex/Em=340/420 nm for 40 min. Glutathione forms were calculated and normalized by protein (Bradford's assay).

Protein Sulfhydryl Groups Determination (Dibromobimane Assays).

Protein reduced thiol groups (Protein-SH) were measured by dibromobimane assays with minor modifications (PMID: 20463849). The 6-well plated cells (500,000 cells) were scraped in 0.6 mL PBS and 200 µL Perchloric acid (6 N) was added to precipitate proteins. The samples were incubated for 5 min in ice, centrifuged (14,000×g) Supernatants containing small peptides and glutathione were discarded and pellets were resuspended in 100 µL NaOH 0.1N, neutralized with 100 µL ice cold Perchloric acid (0.1 N), and 0.1 N PBS was added to keep pH constant. A stock solution of 4 mM dibromobimane in DMSO was added to a final concentration 40 µM, and incubated for 30 30 min at 37° C. Dibromobimane-protein fluorescence was measured at Ex=393 and, Em=477 nm.

ELISA Assays and Conditioned Media Preparation.

Quantification of MMP1 and MMP3 content in culture medium was assessed using RayBio-MMP3 and RayBio-MMP1 Elisa Kit (RayBiotech, Inc); IL8 was analyzed by Human IL-8 Elisa kit (Pierce Biotechnology). The levels of prostaglandin E2 (PGE2) were determined using the Prostaglandin E2 EIA Kit Monoclonal (Cayman Chemical Company). Culture media were diluted to fit within the standard curves. For conditioned media (CM) preparation for invasion and in vitro angiogenesis experiments, 12-well plated cells were treated with MMS (or MMS plus inhibitors) for 8 h in the presence of 10% FBS, twice washed with HBSS, and incubated with 700 µL drug/serum-free fresh medium for additional 12 h. Thereafter, the conditioned fresh medium was collected and directly used for migration and invasion experiments in order to reduce freezing associated loss of activity.

Extracellular Matrix Invasion Assay (Boyden Chamber Systems).

The invasion potential of breast cancer cells was estimated using the QCM™ 24-Well Cell Invasion Assay Fluorimetric (Millipore). Serum starved cells were trypsinized, trypsin-inhibited, centrifuged, resuspended to 5000 cells/µL, and 50 µL of this suspension (250,000 cells) was seeded on 8 µm pore size inserts coated with extracellular matrix in serum-free conditions. Afterwards, 200 µL conditioned (CM) or fresh medium without serum was added to top chambers. The bottom chamber consisted of 500 µL of DMEM supplemented with 10% FBS as chemoattractant. Cells were allowed to migrate for 24 h at 37° C. under 5% $CO_2$. Invaded cells were detached from the bottom side of the insert, lysed and incubated with CyQuant GR fluorescent Dye for 15 min. Fluorescence was read at Ex/Em=480/520 nm. Percentage of invading cells was compared to cell number standard curves.

In Vitro Angiogenesis Experiments.

The Angiophase kit (MBL Inc.) was used to assess the angiogenic potential of conditioned media (CM) from breast cancer cells or the direct effect of pharmaceutical inhibitors (free-drug system) on vessel-like structures formation in vitro. With this kit, human endothelial cells are co-cultured in a specially designed medium to form threadlike tubule structures. These gradually join up to form a network of anastomosing tubules, which resemble the capillary bed found in the CAM assay. Kit-provided cryopreserved co-culture of human endothelial cells were plated and kept for 96 h (proliferative phase) without treatments. Afterwards, the cells were maintained in the presence of conditioned medium from alkylating agent treated cells or control medium for a total of 14 days (angiogenic/vasculogenic phase). Medium was changed each 2 days. At the end of treatments, the cells were fixed and immune-stained for CD31 (PECAM-1), following by incubation with secondary antibody conjugate. ELISA was developed using the soluble substrate p-nitrophenyl-phosphate (p-NPP) whose product was colorimetrically read at 405 nm. After ELISA assays, the wells were washed with $dH_2O$ and tubule staining was performed by incubating CD31-stained tubules with the substrate BCIP/NBT, which form insoluble precipitates. Tubules were counted and photographed for qualitative monitoring.

Animal Studies in Xenografts.

The study was approved by the University of Texas Health Science Center at San Antonio Institutional Animal Care and Use Committee (IACUC) policy as outlined in protocol number 11024. The facility is operated in compliance with the Public Law 89-544 (Animal Welfare Act) and its amendments, Public Health Services Policy on Humane Care and Use of Laboratory Animals (PHS Policy) using the Guide for the Care and Use of Laboratory Animals (Guide) as the basis of operation. Selection of cyclophosphamide and sorafenib doses was based on previously published reports (Sun et al., 2010, *J Int Med Res* 38, 967-76; Wilhelm et al., 2004 *Cancer Res* 64, 7099-109). MDA-MB-231 cells were harvested by trypsinization, washed and re-suspended in serum-free medium. Thereafter, cells were mixed with matrigel (1:1), and approximately $5 \times 10^6$ cells were subcutaneously injected in the right flank of each mouse. When the average tumor volume reached about 100 $mm^3$, mice were randomized into groups of 8 animals each, and the following treatment protocol was implemented: Group 1 (control): 100 µL of saline (i.p.); Group 2: sorafenib (1 mg/kg; i.p.) for 9 days; Group 3: cyclophosphamide 0.1 g/kg on days 2, 4, 6 and 8; Group 4: Sorafenib+cyclophosphamide (combination of same above described regimens). All animals were sacrificed 5 days after the end of treatments (15th day of the treatment protocol). Body weight of mice was recorded weekly, and tumor size was measured thrice a week in two dimensions using a digital caliper. The tumor volume was calculated by the formula $0.5236 \, L1(L2)^2$, where L1 is the long axis, and L2 is the short axis of the tumor. At the termination of the study, mice were euthanized; tumors were excised and a part was fixed in 10% phosphate-buffered formalin for H&E, Masson's staining and immunohistochemistry (IHC) analyses.

The invention claimed is:

1. A method of attenuating chemotherapy induced inflammation comprising administering a sub-cytotoxic dose of 0.001 to 1 mg/kg sorafenib in conjunction with a therapeutic dose of a chemotherapeutic alkylating agent.

2. The method of claim 1, wherein the chemotherapy is administered to a patient having breast cancer or glioblastoma.

3. The method of claim 2, wherein the breast cancer is a triple negative breast cancer.

4. A method of inhibiting growth of cancer cells comprising contacting the cancer cells with a low dose of 0.001 to 1 mg/kg sorafenib and an effective dose of a chemotherapeutic alkylating agent to which the cancer cells are sensitive.

5. The method of claim 4, wherein the alkylating agent is cisplatin.

6. The method of claim 4, wherein the low dose sorafenib is administered prior to the chemotherapeutic drug.

7. The method of claim 4, wherein the low dose sorafenib is administered after administration of the chemotherapeutic drug.

8. The method of claim 4, wherein the low dose sorafenib is administered within 15 minutes the chemotherapeutic drug.

* * * * *